(12) United States Patent
Platzek et al.

(10) Patent No.: US 6,180,113 B1
(45) Date of Patent: Jan. 30, 2001

(54) PHARMACEUTICAL AGENTS THAT CONTAIN PERFLUOROALKYL-CONTAINING METAL COMPLEXES

(75) Inventors: Johannes Platzek; Ulrich Niedballa; Bernd Radüchel; Wolfgang Schlecker; Hanns-Joachim Weinmann; Thomas Frenzel, all of Berlin (DE)

(73) Assignee: Schering AG (DE)

( * ) Notice: Under 35 U.S.C. 154(b), the term of this patent shall be extended for 0 days.

(21) Appl. No.: 08/801,983

(22) Filed: Feb. 19, 1997

Related U.S. Application Data

(60) Provisional application No. 60/012,506, filed on Feb. 29, 1996.

(30) Foreign Application Priority Data

Feb. 23, 1996 (DE) .................................... 196 08 278

(51) Int. Cl.[7] .............................. A61K 49/00; A61K 9/00
(52) U.S. Cl. .................. 424/400; 424/9.3; 424/9.363; 424/9.323; 424/9.52; 540/450; 540/451; 540/452
(58) Field of Search .................. 424/9.3, 9.363, 424/9.323, 9.52, 400; 540/450, 451, 452; 562/565; 544/358

(56) References Cited

U.S. PATENT DOCUMENTS

| 5,399,338 | * | 3/1995 | Born et al. ........................ 424/1.49 |
| 5,690,909 | * | 11/1997 | Platzek et al. .................... 424/9.363 |

FOREIGN PATENT DOCUMENTS

| 2803869 | 8/1979 | (DE) . |
| 0673655 | 9/1995 | (EP) . |
| 9307123 | 4/1993 | (WO) . |
| 9422368 | 10/1994 | (WO) . |

OTHER PUBLICATIONS

Patent Abstracts of Japan, vol. 014, No. 068; JP 01 290633 A (Feb. 8, 1990).
Patent Abstracts of Japan, vol. 008, No. 251; JP 59 130812 A (Nov. 16, 1984).
Patent Abstracts of Japan, vol. 008, No. 251; JP 59 130813 A (Nov. 16, 1984).

* cited by examiner

Primary Examiner—Thurman K. Page
Assistant Examiner—Lakshmi Channavajjala
(74) Attorney, Agent, or Firm—Millen, White, Zelano & Branigan, P.C.

(57) ABSTRACT

Pharmaceutical agents that contain perfluoroalkyl-containing metal complexes are useful in tumor therapy and interventional radiology.

25 Claims, 2 Drawing Sheets

PHARMACEUTICAL AGENTS THAT CONTAIN PERFLUOROALKYL-CONTAINING METAL COMPLEXES

This application claims priority over the provisional application Ser. No. 60/012,506, filed Feb. 29, 1996.

The invention relates to the objects characterized in the claims, i.e., pharmaceutical agents that contain monomeric, perfluoroalkyl-substituted metal complexes and complex salts in tumor therapy and interventional radiology.

The use of foreign materials—brought by injection into the blood circulation to induce an embolism there—was proposed as early as at the beginning of this century [Dawbarn, Journal of the American Medical Association 43:792, (1904)].

This idea was taken up seriously again only about 30 years ago (Young, British Medicinal Journal 283, 1144, 1981). Embolization was used for diagnostic and therapeutic purposes, especially for the treatment of tumors. Embolization of the vascular trunk, which supplies a tumor area with blood, is a technique that is used to bring about either a permanent vascular block and in so doing to promote tumor necrosis or a temporary embolization to increase the therapeutic effect of a simultaneously co-administered chemotherapy agent. The last-mentioned technique is referred to as chemoembolization. The advantage of such a treatment is its local limit. A condition is the presence of a sufficiently large vessel (i.e., a vessel that makes possible a catheterization) that supplies the tumor with blood.

In humans, tumors in the liver are especially accessible for embolization therapy. Liver tumors are supplied with blood via the hepatic artery 80–100%. The normal liver parenchyma, however, is supplied mainly (about 75%) by the portal vein. Consequently, a selective treatment of primary and metastatic liver cancer can be achieved by embolization of the hepatic arteries.

Hepatocellular carcinoma (HCC) is an event that occurs rather rarely in Europe and the USA, but it is regarded in Asia (Japan, South Korea) and Africa as the most common malignant tumor disease, which in a large number of cases accompanies cirrhosis of the liver, caused by Hepatitis B and C [Therapie Konzepte Onkologie [Therapy Concept Oncology, see Seber, J. Schütte (Editors) Springer, 536–545, (1995)]. Despite extensive efforts, to date no major improvement in the very poor prognosis has been achieved in the case of this disease. Both untreated and after systemic treatment with cytostatic agents (mainly 5-fluorouracil, mitomycin C, cisplatin, doxorubicin), the average survival time is 1–9 months after a diagnosis is established [K. Okuda et al. Natural History of HCC and Prognosis in Relation to Treatment. Study of 850 Patients. Cancer 56, 918–928, (1985)]. Solely by the surgical removal of the tumor, which is possible only in about 20% of the patients, however, can a considerable prolongation of life be achieved, but only in a very few cases can an actual cure be achieved.

A worthy goal of new therapy principles is mainly an improvement in the quality of life for the patients, since a complete cure is very difficult to achieve owing to the basic primary disease Hepatitis B according to present understanding. The surgical removal of the tumor represents high stress just as does systemic chemotherapy.

In recent years, chemoembolization has emerged as the method of choice. It is defined as the simultaneous administration of a cytostatic agent mixed with an embolization agent for the purpose of forming a local, temporary embolus, from which the pharmaceutical substance is released slowly and basically over a long period of time (optimum 5–8 days). Because of the limitation of blood flow, it results in an increased pharmaceutical substance exposure of the tumor tissue [P. H. Madoule et al. Chemoembolization: Principles and Perspectives, J. Microencapsulation 1, 21–25, (1984)]. The locally developing ischemia supports the control of the tumor.

In the methods of chemoembolization that are used most often in Japan and South Korea, an emulsion consisting of Lipiodol® (ethyl ester of iodinated poppyseed oil) and aqueous cytostatic agent solutions are used as a peripheral embolizate and as a depot. Since, there are no corresponding ready-to-use preparations on the market, the emulsions are produced in clinics on the spot using "home-made" remedies. This causes the quality of the preparations to vary greatly from clinic to clinic, and no precise and reproducible data on the most parameters such as particle size, retention time in the tumor and extractability exist. The emulsion is introduced via a percutaneous catheter selectively/superselectively in the tumor-carrying branch of the hepatic artery. Generally, the arterial supply is then stopped in addition by Gelfoam® particles, to prevent too quick flushing of the lipiodol emulsion. Lipiodol® accumulates to a certain extent in HCC (T. Konno et al. Selective Targeting of Anticancer Drug and Simultaneous Image Enhancement in Solid Tumors by Arterial Administered Lipid Contrast Medium. Cancer 54, 2367–2374, 1984) and is found only in a small part in healthy liver parenchyma. A problem in this process is that a nonquantifiable portion passes through the capillary bed and then accumulates in the lung or spleen. The embolism is present over a lengthy period (1–4 weeks) and, in addition to the lengthy retention time of the cytostatic-agent in the tumor, serves to place an ischemic stress on the tumor. Owing to deficient biodegradability, Lipiodol® is virtually not excreted and remains in the necrotized tumor tissue, which can thus be resorbed only inadequately. Generally, this treatment is regularly repeated at an interval of several weeks. With this method, survival rates are somewhat below those of surgical removal of the tumor, but significantly above those of chemotherapy alone (T. Kanematsu, A 5-Year Experience of Lipiodolization: Selective Regional Chemotherapy for 200 Patients with HCC, Hepatology, 10, 98–102, 1989. D. Vetter et al. Transcatheter Oily Chemoembolization in the Management of Advahced HCC in Cirrhosis; Results of a Western Comparative Study in 60 Patients, Hepatology, 13, 427–433, 1991).

Despite the problems described, the Lipiodol® process in comparison with other embolization techniques with more or less biodegradable particle suspensions (see Table 1) has gained more acceptance than the as yet most common therapy concept in Asia.

TABLE 1

| | Chemoembolization Agents | | |
|---|---|---|---|
| | Lipiodol | Gelfoam | Spherex |
| Manufacturer | Byk Gulden Guerbet | Upjohn | Kabi Pharmacia |
| Composition | iodinated poppyseed oil | gelatin powder (sponge) that can absorb | degradable starch microspheres, amilomer 25–45 µm |
| Use | RKM for direct lymphography. (No approval for | HCC chemoembolization, often used also with | adjuvant in i.a. liver tumor therapy with |

TABLE 1-continued

Chemoembolization Agents

|  | embolization) | lipiodol trauma | cytostatic agents |
|---|---|---|---|
|  | Ethibloc | Contour Emboli | Angiostat |
| Manufacturer | Ethicon | Rehaforum, Interventional Ther. Corp. USA | Regional Therapeutic Inc., CA |
| Composition | zein, poppy-seed oil, amidotrizoate, emulsion | nondegradable polyvinyl alcohol, foam Ivalon 45–1180 $\mu$m | collagen fibers (5 × 75 $\mu$m) |
| Use | vascular embolization in tumors of the kidney, pancreas, hemangioma | presurgical embolization of hypervascular tumors and AVM | embolization of tumors and abnormal vascular sections |

Additional bibliographic references in the Table:
Concerning Spherex: T. Taguchi, Chemo-Occlusion for the Treatment of Liver Cancer. A New Technique Using Degradable Starch Microspheres, Clin. Pharmacokinet. 26, 275–291, 1994.
Concerning Avitene, Angiostat, Gelfoam: D. Struk et al. Stability Studies on Chemoembolization Mixtures. Dialysis Studies of Doxorubicin and Lipiodol with Avitene, Gelfoam and Angiostat. Invest. Radiol. 28, 1024–1027, 1993.

The perfluoroalkyl-containing metal complexes according to the invention show physicochemical properties that are unusual in aqueous solution. They are thixotropic to a surprisingly high extent, so that these compounds are very suitable as embolizates. These solutions have gel-like consistency in the resting position, but they can flow under the effect of shearing forces (can be conveyed by pumps and by long catheters).

The high viscosity of the compounds that are suitable for use according to the invention results, in the case of small shearing forces, such as those that prevail in the capillary bed of tissues, in a reliable, temporary sealing of these vessels. At the same time, these compounds have flow properties that are adequate under pressure, as are necessary for administration via a long catheter.

The compounds according to the invention offer the possibility of formulating highly effective cytostatic agents (e.g., 5-fluorouracil, mitomycin C, cisplatin, doxorubicin). In this way, the active ingredient is introduced only locally in high concentration in the body. As a result, the systemic stress with the known side effects is small.

The embolus that is formed is not permanent, but can slowly dissolve. The components are removed with the blood and eliminated via the kidney. This is advantageous, since the cytostatic agent that is provided in the formulation is released in this way as from a depot over a prolonged time in direct proximity with the tumor and because after the embolus dissolves, additional administrations are possible.

If the compounds according to the invention contain paramagnetic or x-ray-opaque ions, the embolization process and the success of the therapy can be monitored diagnostically by NMR diagnosis or diagnostic radiology (CT) (interventional radiology).

It is also possible, however, to use combinations of the compounds according to the invention with other contrast media, as are commonly used in NMR diagnosis and diagnostic radiology (e.g., Magnevist$^{(R)}$, Isovist$^{(R)}$, Iopamidol$^{(R)}$, Ultravist$^{(R)}$, etc.).

With the agents according to the invention, the side effects that are described in the case of the previously-known agents, such as mainly microembolisms (e.g., in the lung), are avoided.

The perfluoroalkyl-containing compounds that are suitable for use according to the invention are described by general formula I $$R^F\text{-L-A} \qquad\qquad \text{I}$$

in which
$R^F$ is a perfluorinated, straight-chain or branched carbon chain with formula —$C_nF_{2n}X$, in which
X represents a terminal fluorine, chlorine, bromine, iodine or hydrogen atom, and n stands for numbers 4–30,
L means a direct bond, a methylene group, an —NHCO group, a group $$-\!\!\left[(CH_2)_u\!-\!\!NHCOCH_2\!-\!(CH_2)_p\right]_q\!\!-\!\!\underset{\underset{R^1}{|}}{N}\!-\!SO_2\!-$$

whereby p means numbers 0 to 10, q and u, independently of one another, mean numbers 0 or 1 and
$R^1$ is a hydrogen atom, a methyl group, a —$CH_2$—OH group, a —$CH_2CO_2H$ group or a $C_2$–$C_{15}$ chain, which optionally is interrupted by 1 to 3 oxygen atoms, 1 to 2 CO groups or an optionally substituted aryl group and/or is substituted with 1 to 4 hydroxyl groups, 1 to 2 $C_1$–$C_4$ alkoxy groups, 1 to 2 carboxy groups, a group —$SO_3H$,
or L is a straight-chain, branched, saturated or unsaturated $C_2$–$C_{30}$ carbon chain, which optionally contains 1 to 10 oxygen atoms, 1 to 3 —$NR^1$ groups, 1 to 2 sulfur atoms, a piperazine, a —$CONR^1$ group, a —$NR^1CO$— group, an —$SO_2$ group, an —$NR^1$—$CO_2$ group, 1 to 2 —CO groups, a group
—CO—N-T—N($R^1$)—$SO_2$—$R^F$ or 1 to 2 optionally substituted aryls and/or is interrupted by these groups and/or is optionally substituted with 1 to 3 —$OR^1$ groups, 1 to 2 oxo groups, 1 to 2 —NH—$COR^1$ groups, 1 to 2 —$CONHR^1$ groups, 1 to 2 —$(CH_2)_p$—$CO_2H$ groups, 1 to 2 groups of —$(CH_2)_p$—$(O)_q$—$CH_2CH_2$—$R^F$,
whereby
$R^1$, $R^F$ and p and q have the above-identified meanings, and
T means a $C_2$–$C_{10}$ chain, which optionally is interrupted by 1 to 2 oxygen atoms or 1 to 2 —NHCO— groups,
A stands for a metal complex or its salts of organic an/or inorganic bases or amino acids or amino acid amides, specifically for a complex of general formula II (II)

[chemical structure showing a macrocyclic complex with O=C, OZ$^1$, N atoms, CO$_2$Z$^1$ groups, CO—N with R$^3$ and CH$_2$CH$_2$— substituent, and COY group]

in which $R^3$, $Z^1$ and Y are independent of one another, and
$R^3$ has the meaning of $R^1$ or means —$(CH_2)_m$-L-$R^F$, whereby m is 0, 1 or 2 and L and $R^F$ have the above-mentioned meaning, $Z^1$ means a metal ion equivalent of atomic numbers 12, 20–30, 39, 42, 44 or 57–83, Y means $-OZ^1$ or

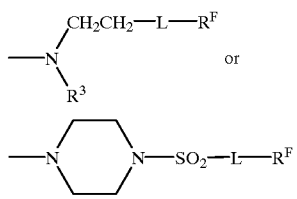

whereby $Z^1$, L, $R^F$ and $R^3$ have the above-mentioned meanings, or

A stands for a complex of general formula III

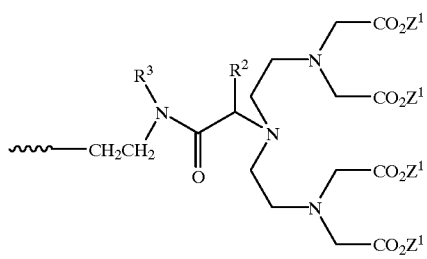

(III)

in which $R^3$ and $Z^1$ have the above-mentioned meanings and $R^2$ has the meaning of $R^1$, or A stands for a complex of general formula IV

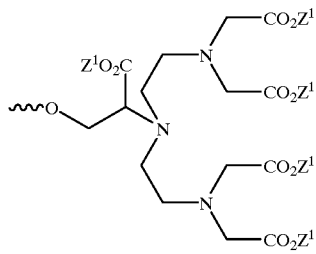

(IV)

in which $Z^1$ has the above-mentioned meaning, or

A stands for a complex of general formula V

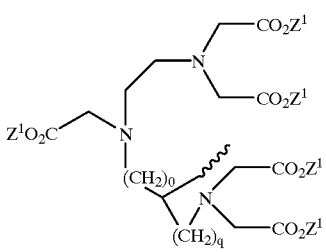

(V)

in which $Z^1$ has the above-mentioned meaning, and 0 and q stand for numbers 0 or 1 and the sum o+q=1 results, or A stands for a complex of general formula VI

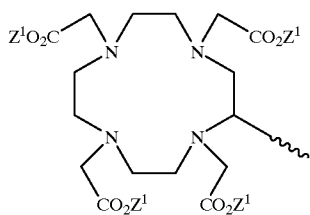

(VI)

in which $Z^1$ has the above-mentioned meaning or

A stands for a complex of general formula VII

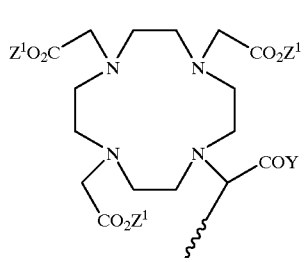

(VII)

in which $Z^1$ and Y have the above-mentioned meanings or

A stands for a complex of general formula VIII

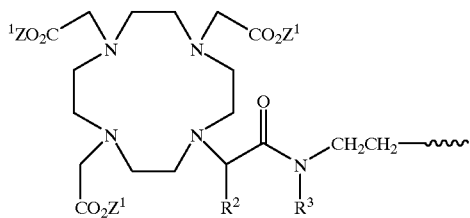

(VIII)

in which $R^3$ and $Z^1$ have the above-mentioned meanings, and $R^2$ has the above-mentioned meaning of $R^1$, or A stands for a complex of general formula IX

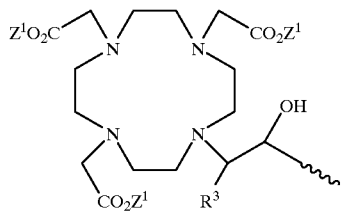

(IX)

in which $R^3$ and $Z^1$ have the above-mentioned meanings, or

A stands for a complexing agent or complex of general formula X

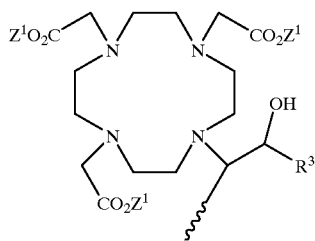
(X)

in which $R^3$ and $Z^1$ have the above-mentioned meanings, or

A stands for a complexing agent or complex of general formula XI

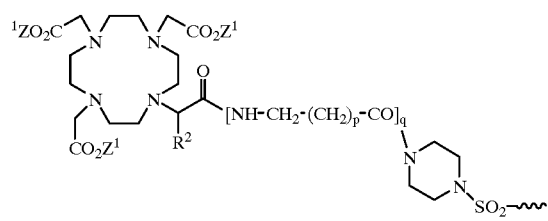
(XI)

in which $Z^1$, p and q have the above-mentioned meanings and $R^2$ has the meaning of $R^1$, or A stands for a complex of general formula XII

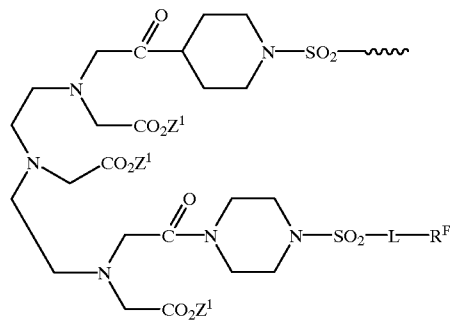
(XII)

in which L, $R^F$ and $Z^1$ have the above-mentioned meanings,

A stands for a complex of general formula XIII

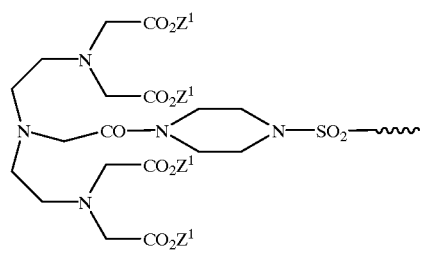
(XIII)

in which $Z^1$ has the above-mentioned meaning, optionally with additives that are commonly used in galenicals, for tumor therapy.

The compounds of general formula I contain the following as preferred radicals L:

—$CH_2$—
—$CH_2CH_2$—
—$(CH_2)_s$— s=3–15
—$CH_2$—O—$CH_2CH_2$—
—$CH_2$—(O—$CH_2$—$CH_2$—)$_t$ t=2–6
—$CH_2$—NH—CO—
—$CH_2$—NH—CO—$CH_2$—N($CH_2COOH$)—$SO_2$—
—$CH_2$—NH—CO—$CH_2$—N($CH_5$)—$SO_2$—
—$CH_2$—NH—CO—$CH_2$—N($C_{10}H_2$)—$SO_2$—
—$CH_2$—NH—CO—$CH_2$—N($C_6H_{13}$)—$SO_2$—
—$CH_2$—NH—CO—$(CH_2)_{10}$—N($C_2H_5$)—$SO_2$—
—$CH_2$—NH—CO—$CH_2$—N(—$CH_2$—$C_6H_5$)—$SO_2$—
—$CH_2$—NH—CO—$CH_2$—N(—$CH_2$—$CH_2$—OH)$SO_2$—
—$CH_2$—NHCO—$(CH_2)_{10}$—S—$CH_2CH_2$—
—$CH_2NHCOCH_2$—O—$CH_2CH_2$—
—$CH_2NHCO(CH_2)_{10}$—O—$CH_2CH_2$—
—$CH_2$—$C_6H_4$—O—$CH_2CH_2$—
—$CH_2$—O—$CH_2$—C($CH_2$—$OCH_2CH_2$—$C_6F_{13}$)$_2$—$CH_2$—$OCH_2$—$CH_2$—

—$CH_2$—$NHCOCH_2CH_2CON$—$CH_2CH_2NHCOCH_2N(C_2H_5)SO_2C_8F_{17}$
                               |
                          $CH_2$—$CH_2NHCOCH_2N(C_2H_5)$–$SO_2$—

—$CH_2$—O—$CH_2$—CH(O$C_{10}H_{21}$)—$CH_2$—O—$CH_2CH_2$—
—($CH_2NHCO$)$_4$—$CH_2$—O—$CH_2CH_2$—
—($CH_2NHCO$)$_3$—$CH_2$—O—$CH_2CH_2$—
—$CH_2$—$OCH_2C(CH_2OH)_2$—$CH_2$—O—$CH_2CH_2$—

—$CH_2$—O—⟨C_6H_3(COOH)⟩—$CH_2$—O—$CH_2$—$CH_2$—

—$CH_2NHCOCH_2N(C_6H_5)$—$SO_2$—
—NHCO—$CH_2$—$CH_2$—
—NHCO—$CH_2$—O—$CH_2CH_2$—
—NH—CO—
—NH—CO—$CH_2$—N($CH_2COOH$)—$SO_2$—
—NH—CO—$CH_2$—N($C_2H_5$)—$SO_2$—
—NH—CO—$CH_2$—N($C_{10}H_{21}$)—$SO_2$—
—NH—CO—$CH_2$—N($C_6H_{13}$)—$SO_2$—
—NH—CO—$(CH_{2)10}$—N($C_2H_5$)—$SO_2$—
—NH—CO—$CH_2$—N(—$CH_2$—$C_6H_5$)—$SO_2$—
—NH—CO—$CH_2$—N(—$CH_2$—$CH_2$—OH)$SO_2$—
—NH—CO—$CH_2$—
—$CH_2$—O—$C_6H_4$—O—$CH_2$—$CH_2$—
—$CH_2$—$C_6H_4$—O—$CH_2$—$CH_2$—
—N($C_2H_5$)—$SO_2$—
—N($C_6H_5$)—$SO_2$—
—N($C_{10}H_{21}$)—$SO_2$—
—N($C_6H_{13}$)—$SO_2$—
—N($C_2H_4OH$)—$SO_2$—
—N($CH_2COOH$)—$SO_2$—
—N($CH_2$—$C_6H_5$)—$SO_2$—

—N[CH(CH$_2$OH)$_2$]—SO$_2$—
—N[CH(CH$_2$OH)—CH(CH$_2$OH)]—SO$_2$—

According to the invention, radicals L of the compounds that are mentioned in the examples of this description of the invention are quite especially preferred.

Other preferred compounds are those in which X of formula —C$_n$F$_{2n}$X means fluorine, and n stands for numbers 4 to 15.

Compounds of general formula I with A in the meaning of general formula IX, whereby L contains at least one —NHCO group, can be obtained from compounds of general formula 14

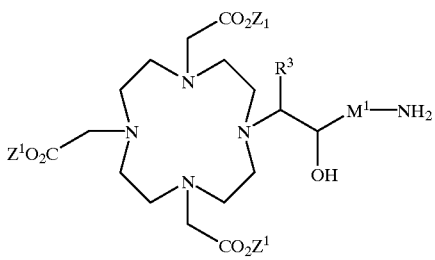

(14)

in which

R$^3$ is in the above-mentioned meaning, Z$^1$ is in the meaning of a metal ion equivalent of atomic numbers 12, 20–30, 39, 42, 44 or 57–83, and M$^1$ is in the meaning of L, by reaction with compounds of general formula 15

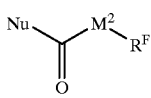

(15)

in which

R$^F$ has the above-mentioned meaning,

M$^2$ is in the meaning of L and

Nu is in the meaning of a nucleofuge.

Advantageously used as nucleofuges are the radicals: Cl, F, - - OTs, - - OMs,

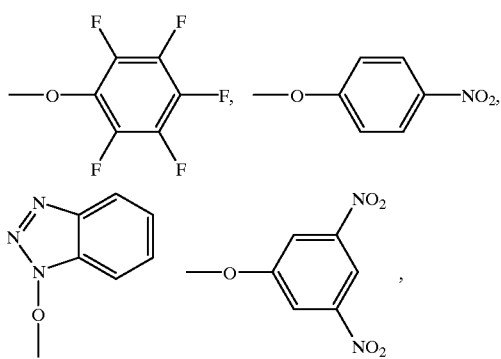

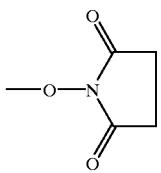

-continued

The reaction is carried out in a mixture of water and organic solvents such as: isopropanol, ethanol, methanol, butanol, dioxane, tetrahydrofuran, dimethylformamide, dimethylacetamide, formamide or dichloromethane. Preferred are ternary mixtures consisting of water, isopropanol and dichloromethane.

The reaction is carried out at a temperature interval between −10° C.–100° C., preferably between 0° C.–30° C.

As acid traps, inorganic and organic bases such as triethylamine, pyridine, N-methylmorpholine, diisopropylethylamine, dimethylaminopyridine, alkali and alkaline-earth hydroxides, their carbonates or bicarbonates such as lithium hydroxide, sodium hydroxide, potassium hydroxide, sodium carbonate, sodium-bicarbonate, potassium bicarbonate are used.

The compounds of general formula 15 are obtained from compounds of general formula 16

HO$_2$C-M$^2$-R$^F$ (16)

in which

R$^F$, M$^2$ have the above-mentioned meaning, according to the processes of acid activation that are generally known to one skilled in the art, such as by reaction of the acid with dicyclohexylcarbodiimide, N-hydroxysuccinimide/dicyclohexylcarbodiimide, carbonyldiimidazole, 2-ethoxy-1-ethoxycarbonyl-1,2-dihydroquinoline, oxalic acid dichloride or isobutyl chloroformate according to the processes described in the literature:

♦ Aktivierung von Carbonsauren [Activation of Carboxylic Acids]. Übersicht in Houben-Weyl, Methoden der Organischen Chemie [Survey in Houben-Weyl, Methods of Organic Chemistry], Volume XV/2, Georg Thieme Verlag Stuttgart, 19.

♦ Aktivierung mit Carbodiimiden [Activation with Carbodiimides]. R. Schwyzer and H. Kappeler, Helv. 46: 1550 (1963).

♦ E. Wünsch et al., Volume 100: 173 (1967).

♦ Aktivierung mit Carbodiimiden/Hydroxysuccinimid [Activation with Carbodiimides/Hydroxysuccinimide]: J. Am. Chem. Soc. 86: 1839 (1964) as well as J. Org. Chem. 53: 3583 (1988). Synthesis 453 (1972).

♦ Anhydridmethode, 2-Ethoxy-1-ethoxycarbonyl-1,2-dihydrochinolin [Anhydride Method, 2-Ethoxy-1-ethoxycarbonyl-1,2-dihydroquinoline]: B. Belleau et al., J. Am. Chem. Soc., 90: 1651 (1986), H. Kunz et al., Int. J. Pept. Prot. Res., 26: 493 (1985) and J. R. Voughn, Am. Soc. 73: 3547 (1951).

♦ Imidazolid-Methode [Imidazolide Method]: B. F. Gisin, R. B. Menifield, D. C. Tosteon, Am. Soc. 91: 2691 (1969).

♦ Säurechlorid-Methoden, Thionylchlorid [Acid Chloride Methods, Thionyl Chloride]: Helv., 42: 1653 (1959).

♦ Oxalylchlorid[Oxalyl Chloride]: J. Org. Chem., 29: 843 (1964).

The compounds of general formula 16 are commercially available products (Fluorochem, ABCR) or are obtained from compounds of general formula 17

$$\text{H-Q-M}^3\text{-R}^F \tag{17}$$

with

M³ in the meaning of L and

Q in the meaning of oxygen, sulfur, a > CO group, > N-R³, R³—N—SO₂ with a bonding of a nitrogen atom to a hydrogen atom, by reaction with compounds of general formula 18

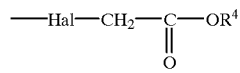
(18)

with

Hal meaning Cl, Br, I and

R⁴ meaning H, methyl, ethyl, t-butyl, benzyl, isopropyl, represented, for example, according to C. F. Ward, Soc. 121, 1161 (1922), according to the methods known to one skilled in the art, such as alkylation of alcohols with alkyl halides [Houben-Weyl, Methoden der organischen Chemie, Sauerstoffverbindungen [Oxygen Compounds] I, Part 3, Methoden zur Herstellung und Umwandlung von Ethern (Methods for the Production and Conversion of Ethers], Georg Thieme Verlag, Stuttgart 1965, [Alkylation of-Alcohols with Alkyl Halides), p. 24, Alkylierung von Alkoholen mit Alkylsulfaten [Alkylation of Alcohols with Alkyl Sulfates] p. 33] or N-Alkylierung eines Sulfonamids mit Alkylsulfonaten [N-Alkylation of a Sulfonamide with Alkylsulfonates] [Houben-Weyl, Methoden der organischen Chemie, XI/2 Stickstoffverbindungen [XI/2 Nitrogen Compounds], Georg Thieme Verlag Stuttgart, 1957, p. 680; J. E. Rickman and T. Atkins, Am. Chem. Soc., 96: 2268, 1974, 96: 2268; F. Chavez and A. D. Sherry, J. Org. Chem. 1989, 54: 29903.

If Q means a > CO group, the reaction is performed with a Wittig reagent of the structure

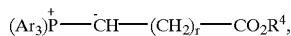

whereby r means numbers 0–16.

The —CH=CH double bond that is produced in this case can remain as a component of the structure or be converted to a —CH₂—CH₂ group by catalytic hydrogenation (Pd 5%/C).

The compounds of general formula 18 are commercially available products (Fluorochem, ABCR).

As an alternative, compounds of general formula I with A in the meaning of general formula IX can be obtained from compounds of general formula 19

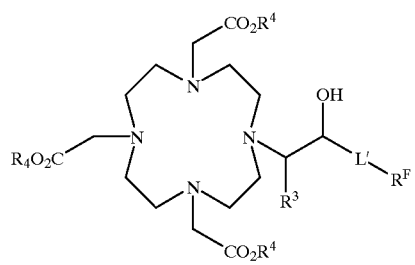
(19)

with

R^F, R³ and R⁴ in the above-mentioned meaning and

L' in the meaning of L, optionally with protected hydroxyl or carboxyl functions, by, if necessary, protective groups that are present being cleaved and the thus obtained complexing agents being reacted with metal oxides or metal salts at room temperature or elevated temperature with the methods known according to one skilled in the art (EP 250358, EP 255471), and then—if desired—acid hydrogen atoms that are present being substituted by cations of inorganic and/or organic bases, amino acids or amino acid amides.

The compounds of general formula 19 are obtained from compounds of general formula 20 (DO3A or the esters)

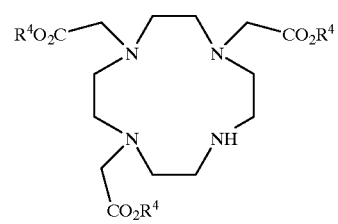
(20)

with

R⁴ in the above-mentioned meaning by reaction with compounds of general formula 21

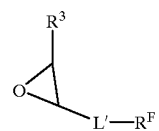
(21)

in which

R³ has the meaning of R¹, optionally in protected form, or —(CH²)$_m$-L'-R^F, whereby m is 0, 1 or 2, and L' and R^F have the above-mentioned meaning. The reaction is carried out in alcohols such as methanol, ethanol, isopropanol, butanol, ethers such as dioxane, tetrahydrofuran, dimethoxy ethers or in water or in mixtures of water and one of the mentioned organic solvents, as well as also acetonitrile, acetone, dimethylformamide, dimethylacetamide or dimethyl sulfoxide, dichloromethane, dichloroethane, chloroform at temperatures between −10° C. and 180° C., preferably at 20°–100° C. The addition of organic or inorganic bases, such as triethylamine, pyridine, dimethylaminopyridine, N-methylmorpholine, diisopropylamine, alkali or alkaline-earth hydroxides or their carbonates or bicarbonates such as lithium hydroxide, sodium hydroxide, potassium hydroxide, sodium carbonate, potassium carbonate, sodium bicarbonate, potassium bicarbonate has proven advantageous. In the case of low-boiling epoxides, the reaction is carried out in an autoclave.

The compounds of general formula 21 are commercially available products (Fluorochem, ABCR) or can be obtained from compounds of general formula 22

$$\text{R}^3\text{—CH=CH-L'-R}^F \tag{22}$$

by epoxidation according to the methods known to one skilled in the art, for example, the wolframate-catalyzed oxidation with H₂O₂ according to Payne, the cyclization of halohydrins or the alkaline H₂O₂ oxidation in the presence of nitriles.

Especially suitable for this reaction is 3-chloroperbenzoic acid in dichloromethane at room temperature. Houben-Weyl, Methoden der Organischen Chemie, Sauerstoffverbindungen I, Part 3, Methoden zur Herstellung und Umwandlung dreigliedriger cyclische Ether (1,2-Epoxide) [Methods for the Production and Conversion of Three-Membered Cyclic Ethers-(1,2Epoxides)], Georg Thieme Verlag, Stuttgart, 1965; G. B. Payne and P. H. Williams, J. Org. Chem., 159, 24: 54; Y. Ogata and Y. Samaki, Tetrahedron 1964, 20: 2065; K. B. Sharpless et al., Pure Appl. Chem. 55, 589 (1983).

Compounds of general formula 22 are preferably obtained by Wittig reaction, or by the variants according to Horner, Schlosser or Bestmann, Houben-Weyl, Methoden der Organischen Chemie XII/1, Organische Phosphorverbindungen Teil 1 [Organic Phosphorus Compounds Part 1], Georg Thieme Verlag, Stuttgart, 1963, Phosphoniumsalze (Phosphonium Salts] p. 79, Phosphoniumylide [Phosphonium Ylides] p. 112, Wittig Reaction p. 121; A. W. Johnson, Ylides and Imines of Phosphorus, John Wiley & Sons, Inc., New York, Chichester, Brisbane, Toronto, Singapore, 1993, Wittig Reaction p. 221; Schlosser-Modifikation der Wittig-Reaktion [Schlosser Modification of the Wittig Reaction] p. 240; Wadsworth-Emmons-Reaktion (Wadsworth-Emmons Reaction] p. 313; Horner Reaktion [Horner Reaction] p. 362, by reaction of a triarylphosphonium ylide

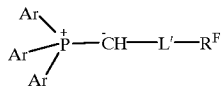 (23)

with L' and $R^F$ in the above-mentioned meaning and Ar meaning aryl, especially phenyl, with commercially available methods (Merck, Fluka) or according to the methods known to one skilled in the art, for example, oxidation of primary alcohols with chromium trioxide/pyridine, Houben-Weyl, Methodender Organischen Chemie, Sauerstoffverbindungen II, Part 1, Aldehyde [Aldehydes], Georg Thieme Verlag, Stuttgart, 1954, aldehydes of general formula 20 that can be produced

 (24)

whereby $R^3$ can also be H.

Triarylphosphonium ylides 23 are produced from the corresponding halides of general formula 25

 (25)

with Hal, L' and $R^F$ in the above-mentioned meaning according to the methods known to one skilled in the art, for example by heating the triarylphosphine with the alkylhalide, Houben-Weyl, Methoden der Organischen Chemie XII/1, Organische Phosphorverbindungen Teil 1, Georg Thieme Verlag, Stuttgart, 1963 or A. W. Johnson, Ylides and Imines of Phosphorus, John Wiley & Sons, Inc., New York, Chichester, Brisbane, Toronto, Singapore, 1993. The compounds of general formula 25 are commercially available products (Fluorochem, ABCR, 3M).

The compounds of general formula 21 with $R^3$=H are preferably obtained from compounds of general formula 17a

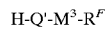 (17a)

in which

Q' is in the meaning of Q, but cannot mean any > CO group, $M^3$ has the meaning of L with the exception of the direct bond and $R^F$ has the above-mentioned meaning, sulfonamidealkylation with epihalohydrins that is known to one skilled in the art: (Houben-Weyl, Methoden der Organischen Chemie, Sauerstoffverbindungen I, Part 3, Methoden zur Herstellung und Umwandlung von Ethern, Georg Thieme Verlag, Stuttgart, 1965, Alkylierung von Alkoholen [Alkylation of Alcohols], p. 24, 33; Houben-Weyl, Methoden der Organischen-Chemie, XI/2 Stickstoffverbindungen, Georg Thieme Verlag, Stuttgart, 1957, p. 680; J. E. Rickman and T. J. J. Atkins, Am. Chem. Soc. 1974, 96: 2268; F. Chavez and A. D. Sherry, 1989, 54: 2990) of general formula 26

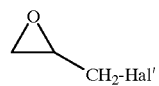 (26)

with

Hal' in the meaning of Hal, F, -OTs, OMs.

In the case of low-boiling epoxides, the reaction is carried out in an autoclave.

Compounds of general formula I with A in the meaning of general formula VIII are obtained from compounds of general formula 27

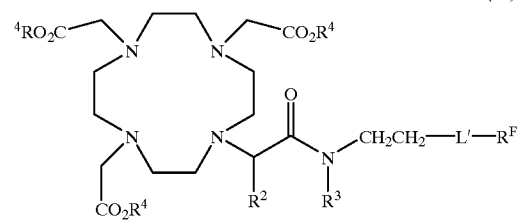 (27)

with $R^2$, $R^3$, $R^4$, L' and $R^F$ in the above-mentioned meaning, by cleavage of optionally present protective groups and complexing in the way known to one skilled in the art.

Compounds of general formula 27 are obtained by alkylation of the compounds of general formula 20 with compounds of general formula 28

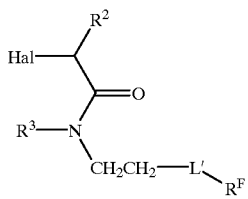 (28)

in which Hal, $R^2$, $R^3$, L' and $R^F$ have the above-mentioned meaning, in a way known in the art, for example as described under EP 0 232 751 B1 (Squibb).

Compounds of general formula 28 are produced from compounds of general formula 29

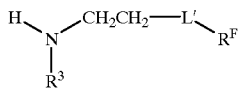
(29)

with L', R³ and R^F in the above-mentioned meaning and an activated halocarboxylic acid of general formula 30

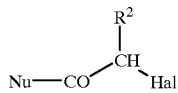
(30)

with Nu, R² and Hal in the above-mentioned meaning according to the methods of amide formation with activated carboxylic acids that are known to one skilled in the art [cf. Lit. p. 11].

Compounds of general formula 30 can be obtained from the acids according to C. Hell, Vol. 14: 891 (1881); J. Volhard, A 242, 141 (1887); N. Zelinsky, Vol. 20: 2026, (1887) or from the haloacids according to the activation methods as they are described in general formula 15.

The compounds of general formula 29 can be easily produced according to the methods of amine synthesis that are known to one skilled in the art [Houben-Weyl, Methoden der Organischen Chemie, Stickstoffverbindungen II, Amino, 1st Run, Georg Thieme Verlag, Stuttgart, 1957] from the commercially available compounds (Fluorochem, ABCR) of general formula 31

(31)

or 32

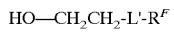
(32)

for example, by alkylation of a compound 31 with an amine PhCH₂NHR³ and subsequent deprotection of the amino group by catalytic hydrogenation or by Mitsunobu reaction [H. Loibner and E. Zbiral, Helv. 59, 2100 (1976), A. K. Bose and B. Lal, Tetrahedron Lett. 3973 (1973)) of a compound 32 with potassium phthalimide and deprotection with hydrazine hydrates.

Compounds of general formula I with A in the meaning of general formula VII are obtained from compounds of general formula 33

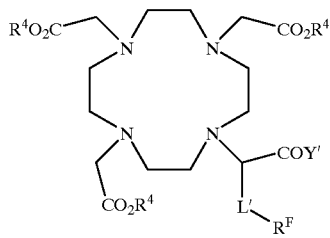
(33)

with
L', R^F and R⁴ in the above-mentioned meaning and
Y' in the meaning of Y, optionally with protective groups, by cleavage of optionally present protective groups and completing according to the methods that are known to one skilled in the art (Protective Groups in organic Synthesis, 2nd Edition, T. W. Greene and P. G. M. Wuts, John Wiley & Sons, Inc., New York, 1991; EP 0 130 934, EP 0 250 358).

Compounds of general formula 33 are obtained from compounds of general formula 20 and compounds of general formula 34

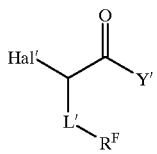
(34)

in which

Hal', L', R^F have the above-mentioned meaning and Y' stands for the radical

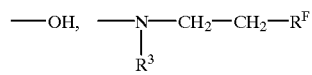

in a way known in the art, for example as described in EP 0 232 751 B1, EP 0 292 689 A2 (both Squibb) or EP 0 255 471 A1 (Schering).

The production of compounds of general formula 34 is carried out according to known methods, for example, according to Hell-Volhard-Zelinsky from commercially available precursors (ABCR).

Compounds of general formula I with A in the meaning of general formula VI are obtained from compounds of general formula 35

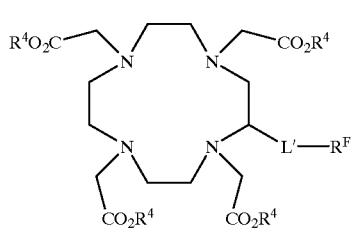
(35)

in which L', R⁴ and R^F have the above-mentioned meaning, by, if appropriate, cleavage of protective groups and complexing in a way known in the art [Protective Groups in Organic Synthesis, 2nd edition, T. W. Greene and P. G. M. Wuts, John Wiley & Sons, Inc., New York, 1991 (EP 0 130 934, EP 0 250 358)].

Compounds of general formula 35 are obtained by reacting α-halocarboxylic acid esters or α-halocarboxylic acids of general formula 18 with compounds of general formula 36

(36)

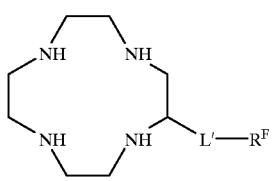

with L' and $R^F$ in the above-mentioned meaning, according to the methods that are known to one skilled in the art, as described, for example, in EP 0 255 471 or U.S. Pat. No. 4,885,363.

Compounds of general formula 36 can be obtained by cleavage of optionally present protective groups and subsequent reduction with diborane according to the known processes from compounds of general formula 37

(37)

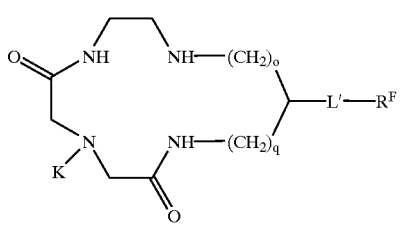

in which

L', $R^F$, o, q, have the above-mentioned meaning and

K has the meaning of a protective group.

The compounds of general formula 37 are available by a condensation reaction from an activated, N-protected iminodiacetic acid 38 and amine 39:

(38)

(39)

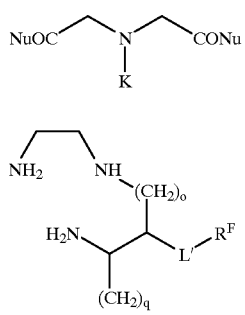

in which

L', $R^F$, o, q, Nu and K have the above-mentioned meaning. As nucleofuge, preferably the N-hydroxysuccinimide is used; as protective group, the benzyloxycarbonyl, trifluoroacetyl or t-butyloxycarbonyl group is used.

Compounds of general formula 38 can be obtained according to the processes of protecting the amino group and of activating carboxylic acid that are known to one skilled in the art [Protective Groups, Aktivierung von Carboxylgruppen [Activation of Carboxyl Groups], p. 11] with protected iminodiacetic acid 40

(40)

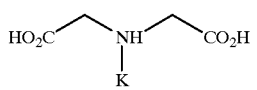

in which

K has the meaning of a protective group, from iminodiacetic acid 41

(41)

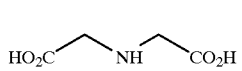

As an alternative, compounds of general formula 36 are available by, if appropriate, cleavage of protective groups and reduction with diborane according to the process described in 37 from compounds of general formula 42

(42)

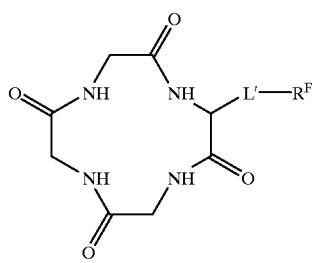

Compounds of general formula 42 can be obtained by closing the rings of Secco compounds 43

(43)

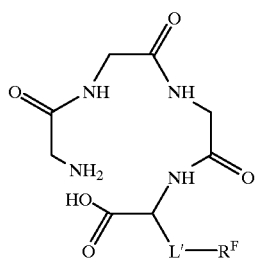

in which

L' and $R^F$ have the above-mentioned meaning, according to standard processes; for example, by reaction with the Mukaiyama reagent 2-fluoro-1-methylpyridinium-tosylate

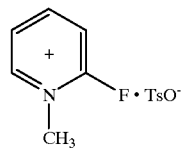

[J. Org. Chem. 1994, 59, 415; Synthetic Communications 1995, 25, 1401] or with the phosphoric acid diphenylester-azide

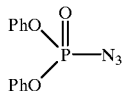

[J. Am. Chem. Soc. 1993, 115, 3420; WO 94/15925].

Compounds of general formula 43 are available according to the described processes by condensation of activated acid 44

(44)

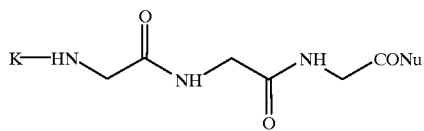

with Nu and K in the above-mentioned meaning, with a compound of general formula 45

(45)

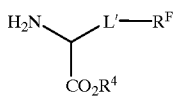

in which

L', $R^4$ and $R^F$ have the above-mentioned meaning.

Compounds of general formula 44 are available from commercially available triglycine (Bachem, Fluka) 46

(46)

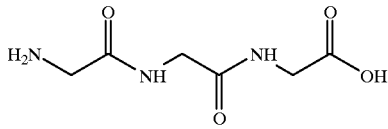

by protection of the amino group with subsequent activation of the acid function according to the processes for amine protection and carboxylic acid reactivation that are known to one skilled in the art (Lit. p. according to formula 16).

The compounds of general formula 45 can be easily obtained from compounds of general formula 62 by introducing protective group $R^4$ according to the methods known to one skilled in the art—for example, re-esterification of a sulfite ester.

Compounds of general formula I with A in the meaning of general formula II are obtained from compounds of general formula 47

(47)

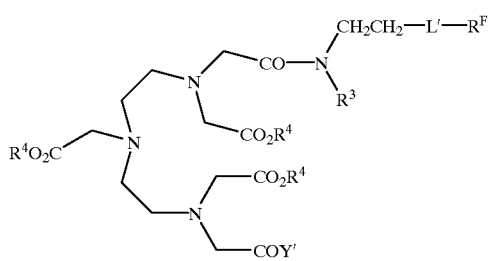

with L', $R^3$, $R^4$, $R^F$ and Y' in the above-mentioned meaning, by, if appropriate, cleavage of protective groups and domplexing in 4a way that is well-known to one skilled in the art (Protective Groups, EP 0 250 358, EP 0 130 934).

If Y' in general formula 47 means an OH group, the compounds are obtained by reacting a compound 48

(48)

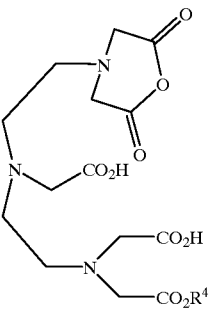

with $R^4$ in the above-mentioned meaning, produced according to DE 3 633 243, with an amine of general formula 29 under the conditions already described and subsequent cleavage of the protective groups.

If Y' in formula 47, however, is the group

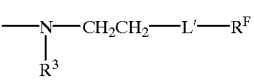

then the reaction is performed under analogous conditions with DTPA-bisanhydride (commercially available product, Merck) 49

(49)

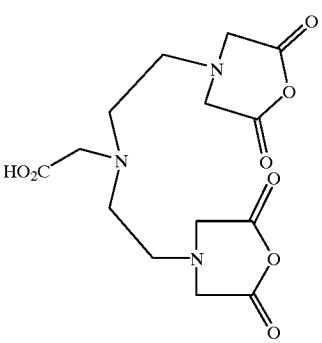

Compounds of general formula I, with A in the meaning of general formula III, are obtained from compounds of general formula 50

(50)

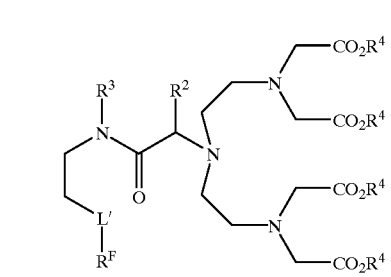

in which

L', $R^2$, $R^3$, $R^4$ and $R^F$ have the above-mentioned meaning, by, if appropriate, cleavage of protective groups and completing in a way that is well-known to one skilled in the art [Protective Groups, EP 0 071564, EP 0 130 934, DE-OS 3 401 052].

Compounds of general formula 50 are obtained according to the process described in J. Org. Chem. 1993, 58: 1151 from compounds of general formula 51

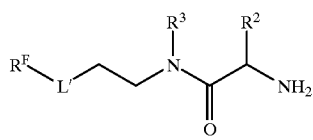
(51)

and halocarboxylic acid derivatives of formula 52

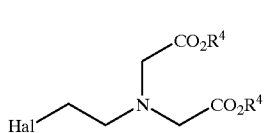
(52)

in which $R^4$ and Hal have the already described meaning. The compounds of general formula 51 are produced by acylation of an amine of general formula 29 with an activated N-protected amino acid of general formula 53

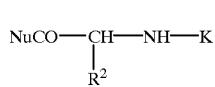
(53)

in which Nu has the above-mentioned meaning and K is in the meaning of a protective group such as Z, -BOC, FMOC, —$COCF_3$, and subsequent cleavage of the protective group.

Compounds of general formula I with A in the meaning of general formula IV are obtained from compounds of general formula 54

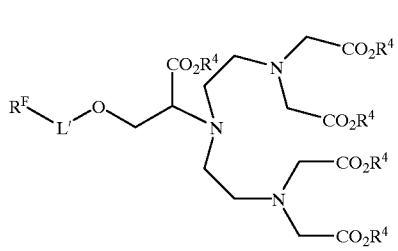
(54)

in which

L', $R^F$ and $R^4$ have the above-mentioned meaning, by, if appropriate, cleavage of the protective groups and complexing according to a method that is known to one skilled in the art, as already described [Protective Groups, EP 0 071 564, EP 0 130 934, DE-OS 3 401 052].

Compounds of general formula 54 can be obtained in a known way from the halogen compounds of general formula 55

Hal-L'-$R^F$ (55)

that can be obtained as commercially available products (Fluorochem, ABCR) by reaction with hydroxy acids 56

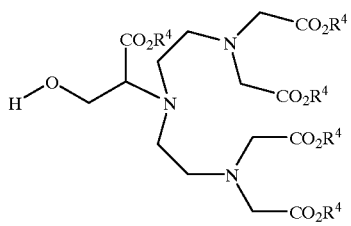
(56)

in which $R^4$ has the above-mentioned meaning. The compounds of formula 56 can be obtained in a way known in the art according to J. Org. Chem. 58, 1151 (1993) from commercially available serine ester 57 (Bachem, Fluka)

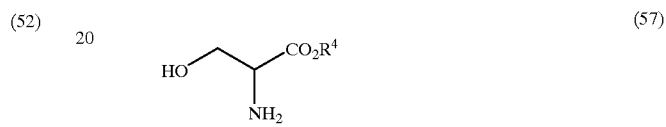
(57)

with $R^4$ in the above-mentioned meaning and halocarboxylic acid esters 58

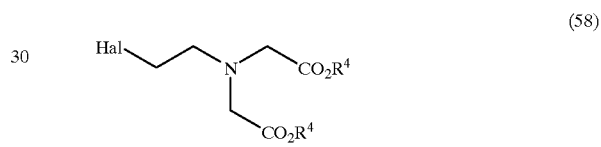
(58)

Compounds of general formula I with A in the meaning of general formula V are obtained from compounds of general formula 59

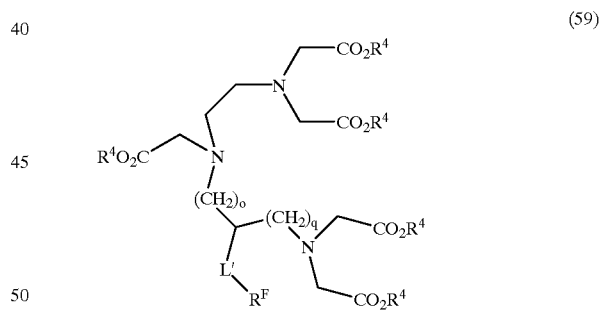
(59)

in which

L', o, q, $R^4$ and $R^F$ have the above-mentioned meaning, by, if appropriate, cleavage of protective groups and complexing according to a method that is known to one skilled in the art. [Protective Groups, EP 0 071 564, EP 0 130 934, DE-OS 3 401 052].

Compounds of general formula 59 can be produced in a known way, for example, according to J. Org. Chem., 58, 1151 (1993), by reaction of halocarboxylic acid esters 18

Hal-$CH_2CO_2R^4$ (18)

with Hal and $R^4$ in the above-mentioned meaning, and a compound of general formula 39

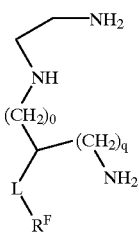

(39)

in which

L', o, q, and $R^F$ have the above-mentioned meaning.

The compounds of general formula 39 are obtained for the case q=0 from the compounds of general formula 60

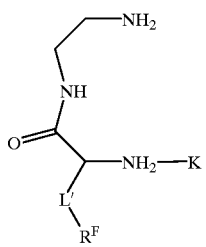

(60)

with

L', $R^F$ and K in the above-mentioned meaning, in a way known in the art [Helv. Chim. Acta, 77: 23 (1994)] by reduction with diborane and cleavage of the-protective groups. The compounds of general formula 60 are obtained with ethylenediamine by aminolysis of the activated compounds of general formula 61

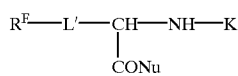

(61)

in which

L', Nu, $R^F$ and K have the above-mentioned meaning.

The compounds of general formula 61 are produced according to the known methods of protective group chemistry [Protective Groups] from the unprotected acid of general formula 62

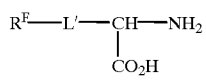

(62)

specifically the amino group is protected in a first step, followed by the activation of the acid group in the second step.

The compounds of general formula 62 can be produced according to the methods of amino acid synthesis [Houben-Weyl, Methoden der organischen Chemie, XI/2 Stickstoffverbindungen II and III, II Aminosäuren [II Amino Acids]; Georg Thieme Verlag Stuttgart, 1958, Strecker-Reaktion [Strecker Reaction], p. 305; Erlenmeyer-Reaktion [Erlenmeyer Reaction], p. 306; Aminolyse von α-Halogencarbonsäuren [Aminolysis of α-Halocarboxylic Acids], p. 309] from the commercially available aldehydes of general formula 63

HOC-L'-$R^F$ (63)

for example, according to Strecker, via the azlactone or via the cyanohydrin.

The compounds of general formula 39 are obtained for the case o=0, from-the compounds of general formula 64

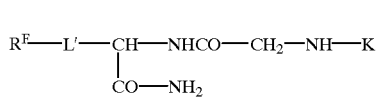

(64)

with $R^F$, L' and K in the mentioned meanings, in a way known in the art by cleavage of the protective groups and reduction with diborane.

Compounds of general formula 64 are available by aminolysis of N-protected activated glycines 53 with compounds of general formula 65

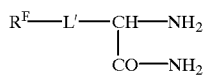

(65)

in which $R^F$ and L' have the mentioned meanings.

The compounds of general formula 65 can be obtained in a simple way from compounds of general formula 61 by amide formation with ammonia and subsequent cleavage of the protective group.

Compounds of general formula XIII can be produced analogously to the compounds of general formula III, by halocarboxylic acid derivatives of general formula 52 being reacted with a compound of general formula 66

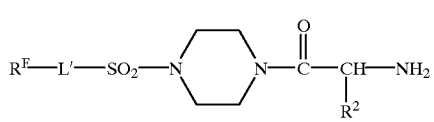

(66)

in which $R^F$, L' and $R^2$ have the above-mentioned meanings.

The compounds of general formula 66 are produced by reaction of a compound of general formula 67

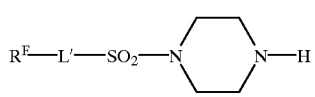

(67)

with the activated, N-protected amino acid of general formula 53 analogously to the reaction of amine 29 with compound 53.

The compounds of general formula 67 can be obtained by reaction of piperazine—freely or optionally partially protected—with perfluoroalkylsulfonic acid fluorides or -chlorides. (The sulfonamide formation from amine and sulfofluoride is described in DOS 2 118 190, DOS 2 153 270, both Bayer AG).

Compounds of general formula XI with q meaning the numbers 0 or 1 are produced analogously to compounds of general formula VIII, by compounds of general formula 20 being reacted with compounds of general formula 68

(68)

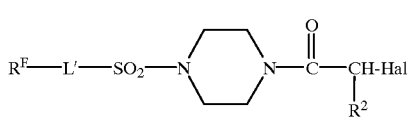

in which R^F, L', R^2 and Hal have the above-mentioned meaning or being reacted with compounds of general formula 68a (68a)

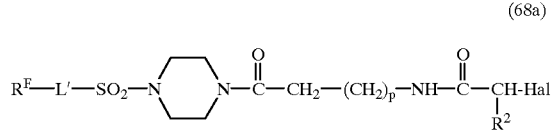

in which R^F, L', R^2, p and Hal have the above-mentioned meanings.

Compounds of general formula 68 can be obtained from compounds of general formula 30 and piperazine derivatives of general formula 67 in a way known in the art.

Compounds of general formula XII are produced analogously to compounds of general formula II, e.g., by reaction of compounds of formula 49 with piperazine derivatives of general formula 67.

Compounds of general formula 68a are produced from compounds of general formula 67 by amide-coupling with compounds of general formula 68b (68b)

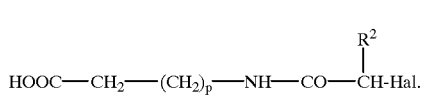

Compounds of general formula I with A in the meaning of general formula X are obtained from compounds of general formula 69

(69)

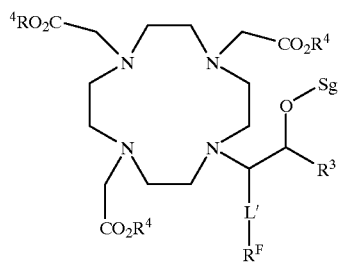

in which

L', R^3, R^4 and RF have the above-described meaning and Sg is in the meaning of a protective group, by, if appropriate, cleavage of protective groups and complexing in a way known in the art [Protective Groups in Organic Synthesis, 2nd Edition, T. W. Greene and P. G. M. Wuts, John Wiley & Sons, Inc., New York, 1991 (EP 0 130 934, EP 0 250 358)].

Compounds of general formula 69 are obtained by reaction of α-halocarboxylic acid esters or a-halocarboxylic acids of general formula 18 with compounds of general formula 70

(70)

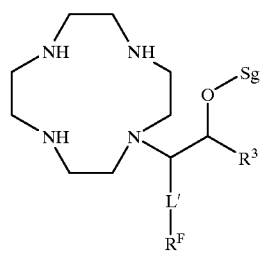

with L', R^F, R^3 and Sg in the above-mentioned meaning according to the methods that are known to one skilled in the art, as described, for example, in EP 0 255 471 or. U.S. Pat. No. 4,885,363.

Compounds of general formula 70 can be obtained by cleavage of optionally present protective groups and subsequent reduction with diborane according to the known processes from compounds of general formula 71

(71)

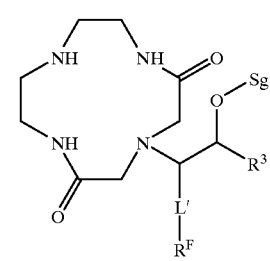

in which

L', R^F, R^3 and Sg have the above-mentioned meaning.

The compounds of general formula 71 can be obtained by a condensation reaction from an activated iminodiacetic acid derivative of general formula 72 and the diethylenetriamine of formula 73

(72)

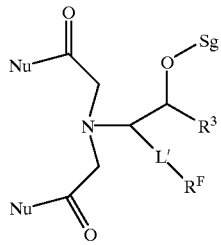

(73)

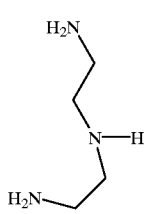

in which

L', R^F, R_3, Sg and Nu have the above-mentioned meaning.

N-Hydroxysuccinimide is preferably used as nucleofuge Nu.

Compounds of general formula 72 can be obtained from compounds of general formula 74

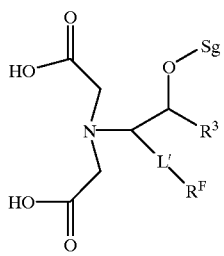
(74)

in which
L', $R^F$ and Sg have the above-mentioned meaning, by activation of carboxylic acids, as described on page 11.

Compounds of general formula 74 are obtained by reaction of α-halocarboxylic acid esters or a-halocarboxylic acids of general formula 18 with compounds of general formula 75

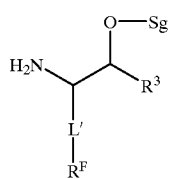
(75)

in which
L', $R^F$, $R^3$ and Sg have the above-mentioned meaning, whereby optionally present ester groups are saponified.

Compounds of general formula 75 are obtained from compounds of general formula 76

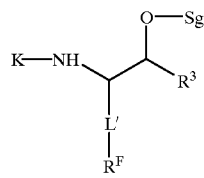
(76)

in which
L', $R^F$, $R^3$, Sg and K have the above-mentioned meaning, by cleavage of protective group K according to the known processes.

Compounds of general formula 76 are obtained from compounds of general formula 77

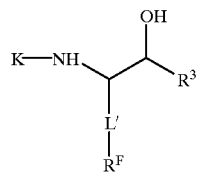
(77)

in which
L', $R^F$, $R^3$ and K have the above-mentioned meaning, by introduction of a protective group Sg in the way known to one skilled in the art.

Compounds of general formula 77 are obtained from the compounds of general formula 78

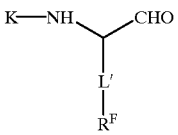
(78)

in which
L', $R^F$ and K have the above-mentioned meaning, according to the methods that are well-known to one skilled in the art (Houben-Weyl, Methoden der Organischen Chemie, XIII 2a, Metallorganische Verbindungen [Organometallic Compounds], Georg Thieme Verlag Stuttgart, 1973, p. 285 ff, Umsetzung magnesiumorganischer Verbindungen mit Aldehyden [Reaction of Magnesium-organic Compounds with Aldehydes]; p. 809 ff, Umsetzung von zinkorganischen Verbindungen mit Aldehyden [Reaction of Zinc-organic Compounds with Aldehydes]; Houben-Weyl, Methoden der Organischen Chemie XIII/1, Metallorganische Verbindungen, Georg Thieme Verlag Stuttgart, 1970; p. 175 ff, Umsetzung lithiumorganischer Verbindungen mit Aldehyden [Reaction of Lithium-organic Compounds with Aldehydes] by reaction with the organometallic compounds, such as magnesium, lithium or zinc compounds, that can be obtained from compounds of general formula 79

Hal-$R^3$ (79)

in which
Hal and $R^3$ have the above-mentioned meaning.
Compounds of general formula 79 are commercially available products (ABCR, Fluka).
Compounds of general formula 78 are produced from compounds of general formula 80

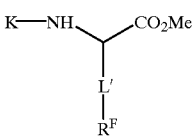
(80)

in which
L', $R^F$ and K have the above-mentioned meaning, by reduction with diisobutylaluminum hydride (Tett. Lett., 1962, 619; Tett. Lett., 1969, 1779; Synthesis, 1975, 617).
Compounds of general formula 80 are produced from compounds of general formula 45

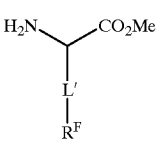
(45)

in which
L' and $R^F$ have the above-mentioned meaning, in a way known to one skilled in the art by introducing protective group K.

The neutralization of optionally still present free carboxy groups is done with the aid of inorganic bases (for example, hydroxides, carbonates or bicarbonates) of, for example, sodium, potassium, lithium, magnesium or calcium and/or organic bases such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine or of amides of originally neutral or acidic amino acids.

To provide neutral complex compounds, enough of the desired bases can be added, for example, to the acid complex salts in aqueous solution or suspension to ensure that the neutral point is reached. The solution obtained can then be evaporated to dryness in a vacuum. often, it is advantageous to precipitate the neutral salts formed by adding water-miscible solvents, such as, for example, lower alcohols (methanol, ethanol, isopropanol and others), lower ketones (acetone and others), polar ethers (tetrahydrofuran, dioxane, 1,2-dimethoxyethane and others) and to obtain easily isolated and readily purified crystallizates. It has proven especially advantageous to add the desired base as early as during the complexing of the reaction mixture and thus to save a process step.

Pharmaceutical agents that contain at least one physiologically compatible compound of general formula I, optionally with the additives that are commonly used in galenicals, are also the object of the invention.

The production of the pharmaceutical agents according to the invention is carried out in a way known in the art, by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca complexes that correspond to the metal complexes according to the invention) or—if necessary—electrolytes, such as, for example, sodium chloride or—if necessary—antioxidants such as, for example, ascorbic acid.

In principle, it is also possible to produce the pharmaceutical agents according to the invention without isolating the complexes. In any case, special care must be used to undertake the chelation so that the complexes according to the invention are practically free from noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex.

The pharmaceutical agents according to the invention preferably contain 0.1 $\mu$mol - 1 mol/l of the complex and are generally dosed in amounts of 0.0001–5 mmol/kg. They are intended for enteral and parenteral administration. The complex compounds according to formula I are used
1. with the ions of the elements of atomic numbers 21–29, 39, 42, 44 and 57–83 for therapy monitoring using NMR diagnosis and diagnostic radiology,
2. with the ions of the elements of atomic numbers 12, 20–30, 39, 42, 44 and 57–83 in a mixture with contrast media for NMR diagnosis or diagnostic radiology,
3. with the ions of the elements of atomic numbers 12, 20–30, 39, 42, 44 and 57–83 in a mixture with chemotherapy agents,
4. with the ions of the elements of atomic numbers 12, 20–30, 39, 42, 44 and 57–83 in a mixture with contrast media for NMR diagnosis or diagnostic radiology and with chemotherapy agents.

The agents according to the invention show the high effectiveness that is necessary to burden the body with the smallest possible amounts of foreign substances, and the good compatibility that is necessary to maintain the noninvasive nature of the studies.

The good water-solubility and low osmolality of the agents according to the invention make it possible to produce highly concentrated solutions, so that osmotic effects do not lead to local undesired reactions. In addition, the agents according to the invention exhibit not only high stability in vitro, but also surprisingly high stability in vivo, so that a release or an exchange of the ions that are bound to the complexes—and toxic in themselves—is carried out only extremely slowly within the time in which the compounds of formula I are completely eliminated again.

The complex compounds of formula I can also be used advantageously as susceptibility reagents and as shift reagents for in vivo NMR spectroscopy.

The compounds of formula I are also distinguished in that they are eliminated completely from the body and are thus highly compatible.

When the agents according to the invention are administered in vivo, the latter can be administered together with a suitable vehicle, such as, for example, serum or physiological common salt solution and together with another protein such as, for example, human serum albumin. In this case, the dosage is dependent on the type of cellular impairment, the metal ion used and the type of imaging method.

The compounds of formula I are used in the form of their aqueous solutions with the additives that are commonly used in pharmaceutics (such as buffers, stabilizers, etc.).

In compounds that are sparingly water-soluble, the addition of solubilizers such as ethanol, dimethyl sulfoxide, propylene glycol or Tween® 80, Triton® X-100 has proven to be effective.

In 96% ethanol, the solubility of the substances according to the invention is very high; more than 500 mmol/l can be reached. Highly concentrated alcohol also promotes the embolization process.

The varying viscosities in the different solvents (mainly 66% propylene glycol) can be used to this end to administer a free-flowing solution that can be administered via a thin catheter with only slight resistance. The viscosity of the embolizing agent is greatly increased by the diluting effect of the blood in the target organ, so that a state as in pure water or plasma is achieved.

In combination preparations for treating tumors, preferably 5-fluorouracil, mitomycin C, cisplatin, doxorubicin and mitomycin are used. As required, aqueous solutions, aqueous solutions with the solubilizers that are commonly used in pharmaceutics or microcrystal suspensions that can be mixed with the compounds of formula I are used.

The chemotherapy agents are administered at doses of 1–2000 mg/preferably 5–1000 mg per administration, whereby repeated administration is possible.

The agents according to the invention are brought preferably into the site of action of the tumor that is to be treated with a catheter. The volume administered depends on the size of the tumor. Generally, 2–80 ml is administered.

Taken overall, the compounds of general formula I, optionally in combination with chemotherapy agents, have been able to open new vistas for the treatment of tumors.

Moreover, these compounds make possible noninvasive therapy monitoring using NMR diagnosis or diagnostic radiology (interventional radiology).

The following examples are used for a more detailed explanation of the object of the invention:

EXAMPLE 1 a) N-Ethyl-N-(perfluorooctylsulfonyl)-amino-acetic acid-t-butyl ester 20 g (37.94 mmol) of N-ethylperfluorooctylsulfonamide and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. The salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 21.66 g (89% of theory) of a waxy colorless solid
Elementary analysis:
Cld: C 29.96 H 2.51 F 50.36 N 2.18 S 5.00
Fnd: C 29.81 H 2.70 F 50.15 N 2.30 S 4.83 b) N-Ethyl-N-(perfluorooctylsulfonyl)-amino-acetic acid 20 g (31.18 mmol) of the title compound of Example 1a) is dissolved in 200 ml of trifluoroacetic acid and stirred overnight at room temperature. It is evaporated to dryness in a vacuum. The residue is recrystallized from methanol/ether.

Yield: 17.34 g (95% of theory) of a colorless crystalline solid
Elementary analysis:
Cld: C 24.63 H 1.38 F 55.19 N 2.39 S 5.48
Fnd: C 24.48 H 1.50 F 55.01 N 2.17 S 5.59 c) Gadolinium complex of 10-[2-hydroxy-4-aza-5-oxo-7-aza-7-(perfluorooctylsulfonyl)-nonyl)-1,4,7-tris(carboxymethyl)-1,4,7,10-tetraazacyclododecane 10 g (17.09 mmol) of the title compound of Example 1b) and 1.97 g (18.79 mmol) of N-hydroxysuccinimide are dissolved in a mixture of 50 ml of dimethylformamide/50 ml of chloroform. At 0° C., 3.88 g (18.79 mmol) of dicyclohexylcarbodiimide is added and stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added and stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 16.37 g (78% of theory) of a colorless, vitreous solid
Water content: 7.1%
$T_1$-relaxivity (L/mmol·sec) at 20 MHz, 37° C.:
41 (water) 49 (human plasma)
Elementary analysis (relative to anhydrous substance):
Cld: C 30.58 H 3.18 F 28.31 Gd 13.78 N 7.37 S 2.81
Fnd: C 30.40 H 3.29 F 28.14 Gd 13.55 N 7.28 S 2.65 d) 10-(2-Hydroxy-4-aza-5-oxo-7-aza-7-(perfluorooctylsulfonyl)-nonyl]-1,4,7-tris(carboxymethyl)-1,4,7,10-tetraazacyclododecane 10 g (8.76 mmol) of the title compound of Example 1c) is dissolved in a mixture of 100 ml of water/100 ml of ethanol, and 1.73 g (13.71 mmol) of oxalic acid-dihydrate is added. It is heated for 8 hours to 80° C. It is cooled to 0° C., and precipitated gadolinium oxalate is filtered out. The filtrate is evaporated to dryness, and the residue is purified on RP-18 (RP-18/mobile solvent: gradient consisting of water/i-propanol/acetonitrile).

Yield: 8.96 g (94% of theory) of a vitreous solid
Water content: 9.3%
Elementary analysis (relative to anhydrous substance):
Cld: C 35.30 H 3.98 F 32.73 N 8.52 S 3.25
Fnd: C 35.10 H 4.15 F 32.51 N 8.35 S 3.15 e) Manganese complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane (as sodium salt)

5 g (5.07 mmol) of the title compound of Example 1d) is dissolved in 100 ml of water, and 0.58 g (5.07 mmol) of manganese(II) carbonate is added. It is stirred for 3 hours at 80° C. The solution is filtered, and the filtrate is adjusted to pH 7.2 with 1N sodium hydroxide solution, then it is freeze-dried.

Yield: 5.87 g (quantitative) of a colorless amorphous powder
Water content: 8.4%
$T_1$-relaxivity (L/mmol sec) at 20 MHz, 37° C.:
2.7 (water)
4.2 (human plasma)
Elementary analysis (relative to anhydrous substance):
Cld: C 32.81 H 3.42 F 30.42 Mn 5.17 N 7.92 Na 2.17 S 3.02
Fnd: C 32.62 H 3.57 F 30.21 Mn 5.06 N 7.80 Na 2.01 S 2.90 f) Ytterbium complex of 10-r2-hydroxy-4-aza-5-oxo-7-aza-7-(perfluorooctyl-sulfonyl)-nonyl]-1,4,7,-tris(carboxymethyl)-1,4,7,10-tetraazacyclododecane 1.33 g (2.53 mmol) of ytterbium carbonate is added to 5 g (5.07 mmol) of the title compound of Example 1d) in 100 ml of water/30 ml of ethanol, and it is stirred for 3 hours at 80° C. The solution is filtered, and the filtrate is evaporated to dryness in a vacuum.

Yield: 6.36 g (quantitative) of a vitreous solid.
Water content: 7.8%.
Elementary analysis (relative to anhydrous substance):
Cld: C 30.11 H 3.14 F 27.92 N 7.27 S 2.77 Yb 14.96
Fnd: C 30.02 H 3.27 F 27.80 N 7.10 S 2.68 Yb 14.75 g) Dysprosium complex of 10-f2-hydroxy-4-aza-5-oxo-7-aza-7-(perfluorooctyl-sulfonyl)-nonyl]-1,4,7,-tris(carboxymethyl)-1,4,7,10-tetraazacyclododecane 0.95 g (2.53 mmol) of dysprosium oxide is added to 5 g (5.07 mmol) of the title compound of Example 1d) in 100 ml of water/30 ml of ethanol, and it is stirred for 3 hours at 80° C. The solution is filtered, and the filtrate is evaporated to dryness in a vacuum.

Yield: 6.35 g (quantitative) of a colorless, vitreous solid.
Water content: 8.5%.
Elementary analysis (relative to anhydrous substance):
Cld: C 30.39 H 3.17 F 28.18 N 7.33 S 2.80 Dy 14.18
Fnd: C 30.17 H 3.25 F 28.03 N 7.21 S 2.65 Dy 14.00

EXAMPLE 2 a) 13,13,13,12,12,11,11,10,10,9,9,8,8,7,7,6,6-Heptadecafluoro-3-oxatridecanoic acid-t-butyl ester 10.51 g (53.9 mmol) of bromoacetic acid-tert-butyl ester is added in drops to a mixture of 10 g (21.55 mmol) of 1H,1H,2H,2H-perfluorodecan-1-ol and 0.73 g (2.15 mmol) of tetrabutylammonium hydrogen sulfate in 100 ml of 60% potassium hydroxide solution/50 ml of toluene while being stirred vigorously at 0° C. It is stirred for 1 hour at 0° C. 200 ml of toluene is added, the aqueous phase is separated and extracted twice with 50 ml of toluene each. The combined organic phases are dried on magnesium sulfate and concentrated by evaporation in a vacuum. The residue is chromatographed on silica gel (mobile solvent: hexane/dichlormethane/acetone=20/10/1).

Yield: 9.72 g (78% of theory) of a colorless viscous oil
Elementary analysis:
Cld: C 33.23 H 2.61 F 55.85
Fnd: C 33.09 H 2.78 F 55.71 b) 13,13,13,12,12,11,11,10,10,9,9,8,8,7,7,6,6-Heptadecafluoro-3-oxatridecanoic acid 9.0 g (15.56 mmol) of the title compound of Example 2a) is dissolved in 180 ml of trifluoroacetic acid and stirred overnight at room temperature. It is evaporated to dryness in a vacuum. The residue is recrystallized from methanol/ether.
Yield: 7.80 g (96% of theory) of a colorless solid
Elementary analysis:
Cld: C 27.60 H 1.35 F 61.85
Fnd: C 27.48 H 1.49 F 61.66 c) Gadolinium complex of 10-[2-hydroxy-4-aza-5-oxo-7-oxa-10,10,11,11,12,12,13,13,14,14,15,15,16,16,17,17,17-heptadecafluoro-heptadecyl]-1,4,7-tris(carboxymethyl)-1,4,7,10-tetraazacyclododecane 7.0 g (13.41 mmol) of the title compound of Example 2b) and 1.70 g (14.75 mmol) of N-hydroxysuccinimide are dissolved in a mixture of 30 ml of dimethylformamide/20 ml of chloroform. At 0° C., 3.04 g (14.75 mmol) of dicyclohexylcarbodiimide is added and stirred for 1 hour at 0° C., then for 3 hours at room temperature. It is cooled again to 0° C., and 4.48 g (44.25 mmol) of triethylamine/50 ml of 2-propanol is added. Then, 8.46 g (14.75 mmol) of the gadolinium complex of 10-(3-amino-2-hydroxy-propyl)-1,4,7-tris(carboxymethyl)-1,4,7,10-tetraazacyclododecane, dissolved in 40 ml of water, is added and stirred for 3 hours at room temperature. It is evaporated to dryness, the residue is taken up in a mixture of 100 ml of methanol/30 ml of chloroform, and dicyclohexylurea is filtered out. The filtrate is evaporated to dryness and purified by RP-chromatography (RP-18/mobile solvent: gradient consisting of water/n-propanol/acetonitrile).
Yield: 11.8 g (75% of theory) of a colorless, vitreous solid
Water content: 8.2%
$T_1$-relaxivity (L/mmol·sec) at 20 MHz, 37° C.:
19 (water)
33 (human plasma)
Elementary analysis:
Cld: C 32.32 H 3.27 F 29.96 Gd 14.59 N 6.50
Fnd: C 32.16 H 3.42 F 29.78 Gd 14.39 N 6.40

EXAMPLE 3 a) 1,2-Epoxy-4-oxa-1H,1H,2H,3H,3H,5H,5H,6H,6H-perfluorotetradecane 7.97 g (86.18 mmol) of epichlorohydrin is added in drops to a mixture of 20 g (43.09 mmol) of 1H,1H,2H,2H-perfluorodecan-1-ol and 0.79 g (2.32 mmol) of tetrabutylammonium hydrogen sulfate in 200 ml of 60% potassium hydroxide solution/100 ml of toluene while being stirred vigorously at 10° C., and care is taken to ensure that the temperature of the reaction solution is not higher than 20° C. It is allowed to stir for 2 hours at 15° C., and then 3.99 g (43.09 mmol) of epichlorohydrin is added in drops as described above. Then, it is stirred overnight at room temperature. 100 ml of methyl-tert-butyl ether is added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone=20/10/1).
Yield: 19.05 g (85% of theory) of a colorless oil
Elementary analysis:
Cld: C 30.02 H 1.74 F 62.09
Fnd: C 29.87 H 1.95 F 61.81 b) 10-[-2Hydroxy-4-oxa-1H,1H,2H,3H,3H,5H,5H,6H,6H-perfluorotetradecyl]-1,4,7-tris(carboxymethyl)-1,4,7,10-tetraazacyclododecane 8.3 g (207.6 mmol) of sodium hydroxide is added to 12.0 (34.60 mmol) of 1,4,7-tris(carboxymethyl)-1,4,7,10-tetraazacyclododecane in 50 ml of water. A solution of 18.0 g (34.60 mmol) of the title compound of Example 3a), dissolved in 60 ml of n-butanol/60 ml of 2-propanol, is added dropwise to it, and the solution is heated overnight to 70° C. It is evaporated to dryness in a vacuum, the residue is taken up in 300 ml of water and adjusted to pH 3 with 3N hydrochloric acid. Then, it is extracted twice with 200 ml of n-butanol. The combined butanol phases are evaporated to dryness in a vacuum, and the residue is purified by RP-chromatography (RP-18/mobile solvent: gradient consisting of water/n-butanol/acetonitrile).
Yield: 26.61 g (79% of theory)
Water content: 11.0%
Elementary analysis (relative to anhydrous substance):
Cld: C 37.42 H 4.07 F 37.27 N 6.47
Fnd: C 37.25 H 4.19 F 37.08 N 6.30 c) Gadolinium complex of 10-[-2hydroxy-4-oxa-1H,1H,2H,3H,3H,5H,5H,6H,6H-perfluorotetradecyl]-1,4,7-tris(carboxymethyl)-1,4,7,10-tetraazacyclododecane 10 g (11.54 mmol) of the title compound of Example 3b) is dissolved in a mixture of 100 ml of water/50 ml of 2-propanol, and 2.09 g (5.77 mmol) of gadolinium oxide is added. It is stirred for 3 hours at 80° C. The solution is filtered and evaporated to dryness in a vacuum.
Yield: 12.48 g (quantitative) of a vitreous solid
Water content: 5.6%
$T_1$-relaxivity (L/mmol·sec) at 20 MHz, 37° C.:
15.2 (water)
27.5 (human plasma)
Elementary analysis (relative to anhydrous substance):
Cld: C 31.77 H 3.16 F 31.64 Gd 15.40 N 5.49
Fnd: C 31.55 H 3.30 F 31.49 Gd 15.28 N 5.35

EXAMPLE 4 a) 1,2-Epoxy-4-oxa-1H,1H,2H,3H,3H,5H,5H,6H,6H-perfluorododecane 10.17 g (109.9 mmol) of epichlorohydrin is added in drops to a mixture of 20 g (54.93 mmol) of 1H,1H,2H,2H-perfluorooctan-1-ol and 1.87 g (5.5 mmol) of tetrabutylammonium hydrogen sulfate in 200 ml of 60% aqueous potassium hydroxide solution/10 ml of toluene while being stirred vigorously at 10° C., and care is taken to ensure that the temperature of the reaction solution is not higher than 20° C. It is allowed to stir for 2 hours at 15° C., and then 5.08 g (54.93 mmol) of epichlorohydrin is added in drops as described above. Then, it is stirred overnight at room temperature. 100 ml of toluene and 100 ml of methyl-tert-butyl ether are added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone=20/10/1).
Yield: 19.15 g (83% of theory) of a colorless oil
Elementary analysis:
Cld: C 31.44 H 2.16 F 58.78
Fnd: C 31.40 H 2.29 F 58.55 b) 10-[2-Hydroxy-4-oxa-1H,1H,2H,3H,3H,5H,5H,6H,6H-perfluorododecyl]-1,4,7-tris(carboxymethyl)-1,4,7,10-tetraazacyclododecane 10.3 g (257 mmol) of sodium hydroxide is added to 14.84 g (42.84 mmol) of 1,4,7-tris(carboxymethyl)-1,4,7,10- tetraazacyclododecane (DO3A) in 70 ml of water. A solution of 18 g (42.84 mmol) of the title compound of Example 4a), dissolved in 80 ml of n-butanol/60 ml of 2-propanol, is added dropwise to it, and the solution is heated overnight to 70° C. It is evaporated to dryness in a vacuum, the residue is taken up in 300 ml of water and adjusted to pH 3 with 3N hydrochloric acid. Then, it is extracted twice with 200 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 27.4 g (75% of theory) of a vitreous solid
Water content: 10.1%
Elementary analysis (relative to anhydrous substance):
Cld: C 39.17 H 4.60 F 32.22 N 7.31
Fnd: C 39.05 H 4.85 F 32.05 N 7.19 c) Gadolinium complex of 10-[2-hydroxy-4-oxa-1H, 1H,2H,3H,3H,5H,5H,6H,6H-perfluorododecyl]-1,4,7-tris(carboxymethyl)-1,4,7,10-tetraazacyclododecane 10 g (13.04 mmol) of the title compound of Example 4b) is dissolved in a mixture of 100 ml of water/50 ml of 2-propanol, and 2.36 g (6.52 mmol) of gadolinium oxide is added. It is stirred for 3 hours at 80° C. The solution is filtered and evaporated to dryness in a vacuum.

Yield: 12.77 g (quantitative) of a vitreous solid
Water content: 6.1%
Elementary analysis (relative to anhydrous substance):
Cld: C 32.61 H 3.50 F 26.82 Gd 17.08 N 6.08
Fnd: C 32.43 H 3.69 F 26.67 Gd 16.85 N 5.91

EXAMPLE 5 a) 9,9,9,8,8,7,7,6,6-Nonafluoro-3-oxa-nonanoic acid-t-butyl ester 29.54 g (151.5 mmol) of bromoacetic acid-tert-butyl ester is added in drops to a mixture of 20 g (75.73 mmol) of 1H,1H,2H,2H-perfluorohexan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for 1 hour at 0° C. 100 ml of toluene is added, the aqueous phase is separated and extracted twice with 50 ml of toluene. The combined organic phases are dried on magnesium sulfate and concentrated by evaporation in a vacuum. The residue is chromatographed on silica gel (mobile solvent: hexane/dichloromethane/acetone=20/10/1).

Yield: 21.48 g (75% of theory) of a colorless oil
Elementary analysis:
Cld: C 38.11 H 4.00 F 45.21
Fnd: C 37.95 H 4.18 F 45.03 b) 9,9,9,8,8,7,7,6,6-Nonanefluoro-3-oxa-nonanoic acid 20 g (52.88 mmol) of the title compound of Example 5a) is dissolved in 300 ml of trifluoroacetic acid and stirred overnight at room temperature. It is evaporated to dryness in a vacuum. The residue is recrystallized from hexane/ether.

Yield: 14.82 g (87% of theory) of a colorless crystalline solid
Elementary analysis:
Cld: C 29.83 H 2.19 F 53.08
Fnd: C 29.71 H 2.40 F 52.90 c) Gadolinium complex of 10-[2-hydroxy-4-aza-5-oxo-7-oxa-10,10,11,11,12,12,13,13,13-nonafluoro-tridecyl]-1,4,7-tris(carboxymethyl)-1,4,7,10-tetraazacyclododecane 7.41 g (23.01 mmol) of the title compound of Example 5b) and 2.91 g (25.31 mmol) of N-hydroxysuccinimide are dissolved in a mixture of 40 ml of dimethylformamide/20 ml of chloroform. At 0° C., 5.22 g (25.31 mmol) of dicyclohexylcarbodiimide is added and stirred for 1 hour at 0° C., then for 3 hours at room temperature. It is cooled again to 0° C., and 6.98 g (69 mmol) of triethylamine/30 ml of 2-propanol is added. Then, 13.2 g (23.01 mmol) of the gadolinium complex of 10-(3-amino-2-hydroxy-propyl)-1 4,7-tris(carboxymethyl)-1,4,7,10-tetraazacyclododecane, dissolved in 40 ml of water, is added and stirred for 3 hours at room temperature. It is evaporated to dryness, the residue is taken up in a mixture of 200 ml of methanol/50 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 15.20 g (71% of theory) of a colorless vitreous solid
Water content: 5.7%
Elementary analysis (relative to anhydrous substance):
Cld: C 34.21 H 4.02 F 19.48 Gd 17.91 N 7.98
Fnd: C 34.09 H 4.18 F 19.31 Gd 17.74 N 7.87

EXAMPLE 6 a) N-Ethyl-N-(perfluorooctylsulfonyl)-amino-acetic acid-N-(2-aminoethyl)-amide 15 g (25.63 mmol) of the title compound of Example 1b) and 3.24 g (28.19 mmol) of N-hydroxysuccinimide are dissolved in 80 ml of dimethylformamide, and 5.82 g (28.19 mmol) of dicyclohexylcarbodiimide is added at 0° C. It is stirred for 1 hour at 0° C., then for 2 hours at room temperature. Precipitated dicyclohexylurea is filtered out, and the filtrate is added in drops within 30 minutes to a solution of 46.21 g (768.9 mmol) of ethylenediamine in 300 ml of dichloromethane. It is stirred for 5 hours at room temperature. 1000 ml of $H_2O$ is added, and the organic phase is separated. The latter is washed twice with 500 ml of water each, then dried on magnesium sulfate and evaporated to dryness in a vacuum. The purification is carried out by chromatography on silica gel. (Mobile solvent: dichloromethane/2-propanol=15/1).

Yield: 11.79 g (75% of theory) of a colorless, waxy solid
Elementary analysis:
Cld: C 27.42 H 2.30 F 52.66 N 4.57 S 5.23
Fnd: C 27.20 H 2.41 F 52.48 N 4.38 S 5.10 b) N-Ethyl-N-(perfluorooctylsulfonyl)-amino-acetic acid-N-[2-(bromoacetyl)-aminoethyl]-amide 10 g (16.3 mmol) of the title compound of Example 6a) and 2.02 g (20 mmol) of triethylamine are dissolved in 40 ml of dichloromethane. At −10° C., 3.29 g (16.3 mmol) of bromoacetyl bromide is added in drops within 30 minutes and stirred for 2 hours at 0° C. The solution is poured into 300 ml of 1N hydrochloric acid and stirred well. The organic phase is separated, dried on magnesium sulfate and concentrated by evaporation in a vacuum. The residue is chromatographed on silica gel (mobile solvent: dichlormethane/acetone=20/1).

Yield: 11.1 g (91% of theory) of a slightly yellow-colored waxy solid
Elementary analysis:
Cld: C 25.68 H 2.02 Br 10.68 F 43.16 N 5.62 S 4.29
Fnd: C 25.47 H 2.18 Br 10.45 F 43.29 N 5.47 S 4.10 c) 10-[2-Oxo-3-aza-6-aza-7-oxo-9-aza-9-(perfluorooctylsulfonyl)-undecyl]-1,4,7-tris(carboxymethyl)-1,4,7,10-tetraazacyclododecane 4.63 g (13.36 mmol) of 1,4,7-tris(carboxymethyl-1,4,7,10-tetraazacyclododecane (DO3A) and 18.5 g (133.6 mmol) of potassium carbonate are added to 10 g (13.36 mmol) of the title compound of Example 6b) in 180 ml of methanol. It is refluxed for 12 hours. The inorganic salts are filtered off, and the filtrate is evaporated to dryness. The residue is taken up in 100 ml of water and adjusted to pH 3 with 5N hydrochloric acid. It is extracted twice with 150 ml of n-butanol. The combined organic phases are evaporated to dryness in a vacuum, and the residue is purified by RP-chromatography (RP-18/mobile solvent=gradient consisting of water/n-butanol/acetonitrile).

Yield: 10.43 g (67% of theory) of a colorless solid
Water content: 13.0%
Elementary analysis (relative to anhydrous substance):
Cld: C 35.55 H 3.98 F 31.86 N 9.67 S 3.16
Fnd: C 35.37 H 3.75 F 31.64 N 9.78 S 3.25 d) Gadolinium complex of 10-[2-oxo-3-aza-6-aza-7-oxo-9-aza-9-(perfluorooctylsulfonyl)-undecyl]-1,4,7-tris(carboxymethyl)-1,4,7,10-tetraazacyclododecane 10 g (9.86 mmol) of the title compound of Example 6c) is dissolved in a mixture of 50 ml of water/20 ml of ethanol, and 1.79 g (4.93 mnmol) of gadolinium oxide is added. It is stirred for 4 hours at 80° C. The solution is filtered and evaporated to dryness in a vacuum.

Yield: 12.4 g (quantitative)
Water content: 7.1%
Elementary analysis (relative to anhydrous substance):
Cld: C 30.85 H 3.19 F 27–65 Gd 13.46 N 8.39 S 2.75
Fnd: C 30.64 H 3.35 F 27.58 Gd 13.29 N 8.28 S 2.65

EXAMPLE 7 a) 1H,1H,2H,2H-Perfluorodecan-1-ol-p-toluenesulfonic acid ester 12.57 g (65.93 mmol) of p-toluenesulfonic acid chloride is added to 30 g (64.64 mmol) of 1H,1H,2H,2H-perfluorodecan-1-ol in 300 ml of dichloromethane and 10.12 g (100 mmol) of triethylamine at 0° C. It is stirred for 2 hours at 0° C., then for 2 hours at room temperature. The solution is poured into 500 ml of cold 2N hydrochloric acid and stirred vigorously. The organic phase is separated, dried on magnesium sulfate and evaporated to dryness. The residue is recrystallized from a little methanol.

Yield: 39.97 (95% of theory) of a colorless crystalline powder
Elementary analysis:
Cld: C 33.02 H 1.79 F 52.23 S 5.19
Fnd: C 32.81 H 1.93 F 52.04 S 5.05 b) 10-[(1-Hydroxymethyl-1-carboxy)-methyl]-1,4,7-tris(carboxymethyl)-1,4,7,10-tetraazacyclododecane 37.2 g (173.4 mmol) of 2-chloro-3-benzyloxy-propanoic acid is added to a solution of 20 g (57.78 mmol) of 1,4,7-tris(carboxymethyl)-1,4,7,10-tetraazacyclododecane (DO3A), 31.21 g (780 mmol) of sodium hydroxide and 2 g (12 mmol) of potassium iodide in 100 ml of dimethylformamide, and it is stirred for 3 days at 60° C. It is evaporated to dryness, and the residue is dissolved in 300 ml of water. Then, it is adjusted to pH 3 with 3N hydrochloric acid and extracted twice with 250 ml of dichloromethane each. 4 g of palladium catalyst (10% Pd/C) is added to the aqueous phase and hydrogenated for 5 hours at 60° C. The catalyst is filtered off, and the filtrate is evaporated to dryness. The residue is purified by RP-chromatography (RP-18/mobile solvent=gradient consisting of water/2-propanol/acetonitrile).

Yield: 5.92 g (21% of theory relative to DO3A) of a colorless, vitreous solid
Water content: 11.1%
Elementary analysis (relative to anhydrous substance):
Cld: C 47.00 H 6.96 N 12.90
Fnd: C 46.81 H 6.78 N 12.99 c) 10-[1-Hydroxymethyl-1-(methoxycarbonyl)-methyl]-1,4,7-tris (methoxycarbonylmethyl)-1,4,7,10-tetraazacyclododecane 9.53 g (80 mmol) of thionyl chloride is added in drops to 200 ml of methanol at 0° C. Then, 5.8 g (13.35 mmol) of the title compound of Example 7b) is added and stirred for 1 hour at 0° C. Then, it is heated for 6 hours to 60° C. It is evaporated to dryness, the residue is taken up in 150 ml of methylene chloride and extracted 3 times with 200 ml of 8% aqueous soda solution each. The organic phase is dried on magnesium sulfate and evaporated to dryness. 6.09 g (93% of theory) of the title compound is obtained as slightly yellowish-colored oil.

Elementary analysis:
Cld: C 51.42 H 7.81 N 11.42
Fnd: C 51.20 H 7.95 N 11.28 d) 10-[1-(Methoxycarbonyl)-3-oxa-1H,2H,2H,4H,4H,5H,5H-perfluorotridecyl]-1,4,7-tris(methoxycarbonylmethyl)-1,4,7,10-tetraazacyclododecane 0.44 g (14.68 mmol) of sodium hydride (80% suspension in mineral oil) is added to 6 g (12.23 mmol) of the title compound of Example 7c) in 40 ml of dimethylformamide and stirred for 30 minutes at −10° C. Then, 8.32 g (13.45 mmol) of the title compound of Example 7a) is added and stirred for 8 hours at room temperature. 400 ml of ice water is carefully added and extracted twice with 300 ml of ethyl acetate each. The combined ethyl acetate phases are washed with saturated aqueous common salt solution and dried on magnesium sulfate. It is evaporated to dryness in a vacuum, and the residue is chromatographed on silica gel (mobile solvent: dichloromethane/methanol=20/1).

Yield: 7.68 g (67% of theory) of a viscous yellow oil
Elementary analysis:
Cld: C 39.75 H 4.41 F 34.48 N 5.98
Fnd: C 39.58 H 4.60 F 34.27 N 5.75 e) 10-[1-Carboxy-3-oxa-1H,2H,2H,4H,4H,5H,5H-perfluorotridecyl]-1,4,7-tris(carboxymethyl)-1,4,7,10-tetraazacyclododecane 7.5 g (8.01 mmol) of the title compound of Example 7d) is suspended in a mixture of 50 ml of water/30 ml of ethanol, and then 3.84 g (96 mmol) of sodium hydroxide is added. It is refluxed overnight. It is cooled to room temperature and adjusted to pH 3 with 3N hydrochloric acid. It is evaporated to dryness in a vacuum, and the residue is purified by RP-chromatography (RP-18/mobile solvent=gradient consisting of water/n-butanol/acetonitrile).

Yield: 6.84 g (87% of theory) of a vitreous solid
Water content: 10.3%
Elementary analysis (relative to anhydrous substance):
Cld: C 36.83 H 3.78 F 36.68 N 6.36
Fnd: C 36.67 H 3.90 F 36.49 N 6.25 f) Gadolinium complex of 10-[1-carboxy-3-oxa-1H,2H,2H,4H,4H,5H,5H-perfluorotridecyl]1,4,7-tris(carboxymethyl)-1,4,7,10-tetraazacyclododecane (as sodium salt)

6 g (6.81 mmol) of the title compound of Example 7e) is suspended in 80 ml of water, and 1.23 g (3.4 mmol) of gadolinium oxide is added. It is heated for 3 hours to 90° C. It is allowed to cool to room temperature and adjusted to pH 7.2 with 2N sodium hydroxide solution. The solution is filtered and then freeze-dried.

Yield: 7.83 g (quantitative) of a colorless, flocculent powder
Water content: 8.1%
Elementary analysis (relative to anhydrous substance):
Cld: C 30.69 H 2.77 F 30.56 Gd 14.88 N 5.30 Na 2.18
Fnd: C 30.48 H 2.85 F 30.37 Gd 14.69 N 5.17 Na 1.95

EXAMPLE 8 a) 2H,2H-Perfluorooctanal 30 g (82.4 mmol) of 1H,1H,2H,2H-perfluorooctan-1-ol is dissolved in 500 ml of dichloromethane, and 17.76 g (82.4 mmol) of pyridinium chlorochromate is added. It is stirred overnight at room temperature. The solution is filtered with a short column, filled with aluminum oxide (neutral), the filtrate is evaporated to dryness and the residue is chromatographed on silica gel (mobile solvent: dichloromethane/hexane/acetone=10/10/1).

Yield: 26.55 g (89% of theory) of a waxy solid
Elementary analysis:
Cld: C 26.54 H 0.84 F 68.21
Fnd: C 26.47 H 1.05 F 68.10 b) 2-Amino-2H,3H,3H-perfluorononanoic acid (as hydrochloride)

7.04 g (143.6 mmol) of sodium cyanide and 8.45 g (158 mmol) of ammonium chloride are dissolved in 30 ml of water. 40 ml of ethanol and 26 g (71.8 mmol) of the title compound of Example 8a) are added to this solution. It is heated for 2 hours to 45° C. 300 ml of water is added, and it is extracted 3 times with 200 ml of benzene each. The combined benzene phases are washed 3 times with 200 ml of water each, and the organic phase is evaporated to dryness in a vacuum. The residue is taken up in 100 ml of 6N aqueous hydrochloric acid/50 ml of methanol and refluxed for 2 hours. It is evaporated to dryness in a vacuum. The residue is recrystallized from a little 2-propanol/methyl-tert-butyl ether.

Yield: 11.15 g (35% of theory) of a crystalline solid
Elementary analysis:
Cld: C 24.37 H 1.59 Cl 7.99 F 55.68 N 3.16
Fnd: C 24.15 H 1.72 Cl 7.65 F 55.51 N 3.05 c) 2-[(N-Benzyloxycarbonyl)-triglycidyl]-amino-2H,3H,3H-perfluorononanoic acid 8.37 g (24.8 mmol) of N-benzyloxycarbonyl-triglycine and 3.14 g (27.28 mmol) of N-hydroxysuccinimide are dissolved in 80 ml of dimethylformamide, and 5.63 g (27.28 mmol) of dicyclohexylcarbodiimide is added at 0° C. It is stirred for 1 hour at 0° C., then for 2 hours at room temperature. It is cooled to 0° C., 7.53 g (74.4 mmol) of triethylamine and 11 g (24.8 mmol) of the title compound of Example 8b are added and then stirred overnight at room temperature. It is evaporated to dryness in a vacuum, the residue is taken up in 300 ml of 5% aqueous citric acid and extracted 3 times with 200 ml of ethyl acetate each. The combined organic phases are dried on magnesium sulfate and evaporated to dryness in a vacuum. The residue is chromatographed on silica gel (mobile solvent: dichloromethane/n-propanol=20/1).

Yield: 11.83 g (67% of theory) of a colorless, sheetlike solid
Elementary analysis:
Cld: C 38.78 H 2.97 F 34.67 N 7.86
Fnd: C 38.59 H 2.85 F 34.48 N 7.91 d) 2-[Triglycidyl]-amino-2H,3H,3H-perfluorononanoic acid 11.5 g (16.14 mmol) of the title compound of Example 8c) is dissolved in 200 ml of 2-propanol, and 3 g of palladium catalyst (10% Pd/C) is added. It is hydrogenated overnight at room temperature. Catalyst is filtered out, and the filtrate is evaporated to dryness.

Yield: 9.33 g (quantitative) of a colorless solid
Elementary analysis:
Cld: C 31.15 H 2.61 F 42.71 N 9.69
Fnd: C 31.29 H 2.80 F 42.53 N 9.48 e) 2-(1H,1H-Perfluoroheptyl)-1,4,7,10-tetraaza-3,6,9,12-tetraoxo-cyclododecane 9.2 g (15.91 mmol) of the title compound of Example 8d) is dissolved in 1000 ml of dimethylformamide, and 3.93 g (15.91 mmol) of 2-ethoxy-1-ethoxycarbonyl-1,2-dihydroquinoline is added. It is stirred for 3 days at room temperature. It is evaporated to dryness, and the residue is chromatographed on silica gel (mobile solvent: dichloromethane/2-propanol=20/1).

Yield: 4.54 g (51% of theory) of a waxy solid
Elementary analysis:
Cld: C 32.16 H 2.34 F 44.08 N 10.00
Fnd: C 32.05 H 2.47 F 43.87 N 9.89 f) 2-(1H,1H-Perfluoroheptyl)-1,4,7,10-tetraazacyclododecane (as tetrahydrochloride)

200 ml of 1M borane-tetrahydrofuran complex solution is added to 4.4 g (7.85 mmol) of the title compound of Example 8e) and refluxed for 2 days. It is evaporated to dryness in a vacuum, and the residue is taken up in 50 ml of concentrated hydrochloric acid. 100 ml of ethanol is added, and it is refluxed for 8 hours. It is evaporated to dryness in a vacuum, and the residue is recrystallized from ethanol.

Yield: 4.75 g (93% of theory) of a colorless, crystalline powder
Elementary analysis:
Cld: C 27.71 H 3.88 Cl 21.81 F 37.99 N 8.62
Fnd: C 27.65 H 3.95 Cl 21.40 F 37.69 N 8.41 g) 2-(1H,1H-Perfluoroheptyl)-1,4,7,10-tetra(carboxymethyl)-1,4,7,10-tetraazacyclododecane 4.6 g (7.07 mmol) of the title compound of Example 8f) and 4.0 g (42.4 mmol) of chloroacetic acid are dissolved in 40 ml of water, and the pH is adjusted to 10 by adding 30% aqueous potassium hydroxide solution. It is heated for 8 hours to 70° C. and in this case, the pH is kept between 8 and 10 (by adding 30% aqueous potassium hydroxide solution). The solution is cooled to room temperature, adjusted to pH 2 with concentrated hydrochloric acid and evaporated to dryness. The residue is taken up in 150 ml of methanol, the salts are filtered off and the filtrate is evaporated to dryness in a vacuum. The residue is purified by RP-18 chromatography (RP-18/mobile solvent: gradient consisting of water/2-propanol/acetonitrile).

Yield: 5.03 g (87% of theory) of a vitreous solid
Water content: 10.1%
Elementary analysis (relative to anhydrous substance):
Cld: C 37.51 H 3.97 F 33.53 N 7.61
Fnd: C 37.35 H 4.12 F 33.40 N 7.45 h) Gadolinium complex of 2-(1H,1H-perfluoroheptyl)-1,4,7,10-tetra(carboxymethyl)-1,4,7,10-tetraazacyclododecane (as sodium salt)

4.5 g (6.11 mmol) of the title compound of Example 8g) is suspended in 100 ml of water, and 1.107 g (3.05 mmol) of gadolinium oxide is added. It is heated for 3 hours to 90° C. It is allowed to cool to room temperature and adjusted to pH 7.2 with 2N sodium hydroxide solution. The solution is filtered and then freeze-dried.

Yield: 6.03 g (quantitative) of a colorless powder
Water content: 7.5%
Elementary analysis (relative to anhydrous substance):
Cld: C 30.23 H 2.87 F 27.03 Gd 17.21 N 6.13 Na 2.52
Fnd: C 30.10 H 3.05 F 26.81 Gd 17.15 N 5.95 Na 2.30

EXAMPLE 9 a) 10-[2-Hydroxy-1H,1H,2H,3H,3H-perfluorononyl]-1,4,7-tris(carboxymethyl)-1,4,7,10-tetraazacyclododecane 13.85 g (346.4 mmol) of sodium hydroxide is added to 15 g (43.3 mmol) of 1,4,7-tris(carboxymethyl)-1,4,7,10-tetraazacyclododecane in 50 ml of water. A solution of 27.68 g (64.95 mmol) of 1,2-epoxy-1H,1H,2H,3H,3H- perfluorononane, dissolved in 50 ml of n-butanol/50 ml of 2-propanol, is added dropwise to it, and the solution is heated overnight to 80° C. It is evaporated to dryness in a vacuum, the residue is taken up in 200 ml of water and adjusted to pH 3 with 3N hydrochloric acid. Then, it is extracted twice with 200 ml of n-butanol. The combined butanol phases are evaporated to dryness in a vacuum, and the residue is purified by RP-chromatography (RP-18/ mobile solvent: gradient consisting of water/n-butanol/ acetonitrile).

Yield: 30.34 g (78% of theory) of a vitreous solid
Water content: 13.7%
Elementary analysis (relative to anhydrous substance):
Cld: C 37.32 H 4.04 F 36.89 N 7.25
Fnd: C 37.15 H 4.21 F 36.70 N 7.19 b) Gadolinium complex of 10-[2-hydroxy-1H,1H,2H,3H, 3H-perfluorononyl]-1,4,7-tris(carboxymethyl)-1,4,7,10-tetraazacyclododecane 10 g (12.94 mmol) of the title compound of Example 9a) is dissolved in 100 ml of water/50 ml of ethanol, and 2.34 g (6.47 mmol) of gadolinium oxide is added. It is stirred for 3 hours at 80° C. The solution is filtered and evaporated to dryness in a vacuum.

Yield: 13.16 g (quantitative) of a colorless, vitreous solid
Water content: 9.1%
Elementary analysis (relative to anhydrous substance):
Cld: C 31.11 H 3.05 F 30.75 Gd 16.97 N 6.05
Fnd: C 31.01 H 3.19 F 30.55 Gd 16.71 N 5.88

EXAMPLE 10 a) 9H,9H,10H,11H,12H,12H-Perfluoroeicos-10-ene 24.77 g (52.26 mmol) of 1H,1H,2H,2H-perfluorodecyl-1-iodide and 13.71 g (52.26 mmol) of triphenylphosphine are heated to 70° C. in 500 ml of acetone while being stirred. The initially clear solution quickly turns milky, and the colorless phosphonium salt is precipitated. The phosphonium salt is filtered off and dried in a vacuum at 40° C.

Yield: 38.9 g (89% of theory)

This phosphonium salt is used directly in the following reaction without purification: 5.22 g (46.5 mmol) of potassium-tert-butylate, 0.20 g (0.75 mmol) of 18-crown 6 and 19.54 g (42.28 mmol) of 2H,2H-perfluorodecanol are added to the above-produced phosphonium salt, 38.9 g (46.5 mmol) in 250 ml of dichloromethane, and it is stirred for 10 hours at room temperature. It is evaporated to dryness, and the residue is chromatographed on silica gel (mobile solvent: dichloromethane/n-hexane/diethyl ether=10/20/1).

Yield: 30.3 g (65% of theory relative to the iodide used) of a colorless waxy solid
Elementary analysis:
Cld: C 26.92 H 0.68 F 72.40
Fnd: C 26.81 H 0.79 F 72.20 b) 10,11-Epoxy-9H,9H,10H,11H,12H,12H-perfluoroeicosane 10.47 g (36.42 mmol) of 3-chloroperoxybenzoic acid (about 60%) is added to 25 g (28.02 mmol) of the title compound of Example 10a), dissolved in 250 ml of dichloromethane, at 0° C., and it is stirred overnight at room temperature. 300 ml of 5% aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/ diethyl ether=10/10/1).

Yield: 24.17 g (95% of theory) of a colorless solid
Elementary analysis:
Cld: C 26.45 H 0.67 F 71.12
Fnd: C 26.25 H 0.88 F 71.35 c) 10-[1-(1H,1H-Perfluorononyl)-2-hydroxy-1H,2H,3H, 3H-perfluoroundecyl]-1,4,7-tris(carboxymethyl)-1,4,7, 10-tetraazacyclododecane 7.04 g (0.176 mmol) of sodium hydroxide is added to 7.63 g (22.02 mmol) of 1,4,7-tris(carboxymethyl)-1,4,7,10-tetraazacyclododecane in 35 ml of water. A solution of 20 g (22.02 mmol) of the title compound of Example 10b), dissolved in 50 ml of n-butanol/40 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/ mobile solvent: gradient consisting of water/n-butanol/ acetonitrile).

Yield: 9.79 g (31% of theory) of a colorless, vitreous solid
Water content: 12.5%
Elementary analysis (relative to anhydrous substance):
Cld: C 32.55 H 2.57 F 51.49 N 4.47
Fnd: C 32.38 H 2.75 F 51.29 N 4.28 d) Gadolinium complex of 10-[1-(1H,1H-perfluorononyl)-2-hydroxy-1H, 2H,3H,3H-perfluoroundecyl]-1,4,7-tris (carboxymethyl)-1,4,7,10-tetraazacyclododecane 8 g (6.38 mmol) of the title compound of Example 10c) is =dissolved in 50 ml of water/40 ml of ethanol/20 ml of chloroform, and 1.16 g (3.19 mmol) of gadolinium oxide is added. It is stirred for 4 hours at ·90° C. in an autoclave. The solution is filtered and evaporated to dryness in a vacuum.

Yield: 9.47 g (quantitative) of a vitreous solid
Water content: 5.2%
Elementary analysis (relative to anhydrous substance):
Cld: C 28.99 H 2.07 F 45.85 Gd 11.16 N 3.98
Fnd: C 28.81 H 2.19 F 45.71 Gd 11.03 N 4.12

EXAMPLE 11 a) 7H,7H,8H,9H,10H,10H-Perfluorohexadec-8-ene 18.7 g (50 mmol) of 1H,1H,2H,2H-perfluorooctyl-1-iodide and 13.11 g (50 mmol) of triphenylphosphine are heated to 70° C. in 400 ml of acetone while being stirred. The initially clear solution quickly turns milky, and the colorless phosphonium salt is precipitated. The phosphonium salt is filtered off and dried in a vacuum at 40° C.

Yield: 28.95 g (91% of theory)

This phosphonium salt is used directly in the following reaction without purification: 5.05 g (45.5 mmol) of potassium-tert-butylate, 0.20 g (0.75 mmol) of 18-crown 6 and 14.98 g (41.36 mmol) of the title compound of Example 8a) are added to the above-produced phosphonium salt, 28.95 g (45.5 mmol) in 200 ml of dichloromethane, and it is stirred for 10 hours at room temperature. It is evaporated to dryness, and the residue is chromatographed on silica gel (mobile solvent: dichloromethane/n-hexane/diethyl ether= 10/20/1).

Yield: 19.65 g (61% of theory) of a colorless, waxy solid
Elementary analysis:
Cld: C 22.38 H 0.94 F 76.69
Fnd: C 22.20 H 0.99 F 76.51 b) 8,9-Epoxy-7H,7H,8H,9H,10H,10H-perfluorohexadecane 11.03 g (38.35 mmol) of 3-chloroperoxybenzoic acid (about 60%) is added to 19 g (29.5 mmol) of the title compound of Example 11a), dissolved in 200 ml of dichloromethane, at 0° C., and it is stirred overnight at room temperature. 300 ml of 5k aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/diethyl ether=10/10/1).

Yield: 19.43 g (93% of theory) of a colorless solid
Elementary analysis:
Cld: C 27.14 H 0.85 F 69.75
Fnd: C 27.01 H 0.97 F 69.60 c) 10-[1-(1H,1H-Perfluoroheptyl)-2-hydroxy-1H,2H,3H,3H-perfluorononyl]-1,4,7-tris(carboxymethyl)-1,4,7,10-tetraazacyclododecane 8.59 g (214.6 mmol) of sodium hydroxide is added to 9.3 g (26.83 mmol) of 1,4,7-tris(carboxymethyl)-1,4,7,10-tetraazacyclododecane in 50 ml of water. A solution of 19 g (26.83 mmol) of the title compound of Example 11b), dissolved in 70 ml of n-butanol/60 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 9.4 g (29% of theory) of a vitreous solid
Water content: 12.7%
Elementary analysis (relative to anhydrous substance):
Cld: C 34.17 H 3.06 F 46.84 N 5.31
Fnd: C 33.98 H 3.18 F 46.65 N 5.20 d) Gadolinium complex of 10-[1-(1H,1H-perfluoroheptyl)-2-hydroxy-1H,2H,3H,3H-perfluorononyl]-1,4,7-tris(carboxymethyl)-1,4,7,10-tetraazacyclododecane 9 g (8.53 mmol) of the title compound of Example 11c) is dissolved in 60 ml of water/40 ml of ethanol/30 ml of chloroform, and 1.54 g (4.27 mmol) of gadolinium oxide is added. It is stirred for 4 hours at 90° C. in an autoclave. The solution is filtered and evaporated to dryness in a vacuum.

Yield: 11.45 g (quantitative) of a colorless, vitreous solid
Water content: 10.2%
Elementary analysis (relative to anhydrous substance):
Cld: C 29.81 H 2.42 F 40.86 Gd 13.01 N 4.63
Fnd: C 29.60 H 2.60 F 40.63 Gd 12.84 N 4.51

EXAMPLE 12 a) 7,12-Dioxa-5H,5H,6H,6H,8H,8H,9H,10H,11H,11H,13H,13H,14H,14H-perfluorooctadec-9-ene 30 g (91.74 mmol) of 1H,1H,2H,2H-perfluorohexyl-1-bromide is dissolved in 100 ml of toluene, then 3.23 g (36.7 mmol) of cis-1,4-butene-diol and 1 g (2.95 mmol) of tetrabutylammonium hydrogen sulfate are added. It is cooled to 0° C., and 16 g (400 mmol) of finely powdered sodium hydroxide is added. Then, it is stirred for 1 hour at 0° C. and overnight at room temperature. Solid is filtered out, the filtrate is washed twice with 200 ml of water each, the organic phase is dried on magnesium sulfate and then evaporated to dryness in a vacuum. The residue is chromatographed on silica gel (mobile solvent: dichloromethane/n-hexane/acetone=15/15/1).

Yield: 11.71 g (55% of theory relative to diol) of a waxy solid
Elementary analysis:
Cld: C 33.12 H 2.43 F 58.93
Fnd: C 33.05 H 2.61 F 58.73 b) 9,10-Epoxy-7,12-dioxa-5H,5H,6H,6H,8H,8H,9H,10H,11H,11H,13H,13H,14H,14H-perfluorooctadecane 7.08 g (24.64 mmol) of 3-chloroperoxybenzoic acid (about 60%) is added to 11 g (18.96 mmol) of the title compound of Example 12a), dissolved in 100 ml of dichloromethane, at 0° C., and it is stirred overnight at room temperature. 150 ml of 5% aqueous sodium carbonate solution is added and stirred well. The organic phase is separated, dried on magnesium sulfate and evaporated to dryness in a vacuum. The residue is chromatographed on silica gel (mobile solvent: n-hexane/dichloromethane/diethyl ether=10/10/1).

Yield: 10.74 g (95% of theory) of a colorless solid
Elementary analysis:
Cld: C 32.23 H 2.37 F 57.35
Fnd: C 32.13 H 2.51 F 57.20 c) 10-[1-(2-Oxa-1H,1H,3H,3H,4H,4H-perfluorooctyl)-2-hydroxy-4-oxa-1H,2H,3H,3H,5H,5H,6H,6H-perfluorodecyl]-1,4,7-tris(carboxymethyl)-1,4,7,10-tetraazacyclododecane 5.63 g (141 mmol) of sodium hydroxide is added to 6.1 g (17.61 mmol) of 1,4,7-tris(carboxymethyl)-1,4,7,10-tetraazacyclododecane in 40 ml of water. A solution of 10.5 g (17.61 mmol) of the title compound of Example 12b), dissolved in 50 ml of n-butanol/40 ml of 2-propanol, is added dropwise to it, and the solution is heated overnight to 120° C. in an autoclave. It is evaporated to dryness in a vacuum, the residue is taken up in 200 ml of water and adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 4.96 g (27% of theory) of a colorless, vitreous solid
Water content: 9.7%
Elementary analysis (relative to anhydrous substance):
Cld: C 38.27 H 4.17 F 36.32 N 5.95
Fnd: C 38.12 H 4.20 F 36.20 N 5.81 d) Gadolinium complex of 10-[1-(2-oxa-1H,1H,3H,3H,4H,4H-perfluorooctyl)-2-hydroxy-4-oxa-1H,2H,3H,3H,5H,5H,6H,6H-perfluorodecyl]-1,4,7-tris(carboxymethyl)-1,4,7,10-tetraazacyclododecane 4.7 g (5 mmol) of the title compound of Example 12c) is dissolved in 30 ml of water/30 ml of ethanol/20 ml of chloroform, and 0.90 g (2.5 mmol) of gadolinium oxide is added. It is stirred for 3.5 hours at 90° C. in an autoclave. The solution is filtered and evaporated to dryness in a vacuum.

Yield: 5.89 g (quantitative) of a colorless, vitreous solid
Water content: 7.1%
Elementary analysis (relative to anhydrous substance):
Cld: C 32.88 H 3.31 F 31.21 Gd 14.35 N 5.11
Fnd: C 32.67 H 3.45 F 31.04 Gd 14.18 N 5.02

EXAMPLE 13 a) 1-Phenyl-2,6-dioxa-1H,1H,3H,3H,4H,5H,5H,7H,7H,8H,8H-perfluorohexadecan-4-ol 1 g (2.94 mmol) of tetrabutylammonium hydrogen sulfate and 15.6 g (390 mmol) of finely powdered sodium hydroxide are added to 7.14 g (39.2 mmol) of glycerol-l-monobenzylether and 25 g (43.55 mmol) of 1H,1H,2H,2H-perfluorodecyl-1-iodide in 100 ml of toluene. It is stirred for 24 hours at room temperature. The organic phase is separated from the solid and washed twice with 5% aqueous hydrochloric acid each. The organic phase is dried on magnesium sulfate and evaporated to dryness in a vacuum. The residue is chromatographed on silica gel (mobile solvent: n-hexane/acetone=15/1).

Yield: 19.95 g (81% of theory) of a colorless oil
Elementary analysis:

Cld: C 38.23 H 2.73 F 51.40
Fnd: C 38.10 H 2.89 F 51.25 b) 1-Phenyl-4-(decyloxy)-2,6-dioxa-1H,1H,3H,3H,4H,5H, 5H,7H,7H,8H,8H-perfluorohexadecane 1.12 g (37.24 mmol) of sodium hydride (80% suspension in mineral oil) is added in portions to 19.5 g (31.03 mmol) of the title compound of Example 13a), dissolved in 100 ml of dimethylformamide, and it is stirred for 2 hours at room temperature. Then, 8.24 g (37.24 mmol) of n-decyl bromide is added and stirred overnight at 50° C. 150 ml of ice water is added and extracted twice with 150 ml of ethyl acetate each. The combined organic phases are washed twice with 150 ml of water each, dried on magnesium sulfate and evaporated to dryness. The residue is chromatographed on silica gel (mobile solvent: n-hexane/acetone=20:1).

Yield: 22.66 g (95% of theory) of a waxy solid
Elementary analysis:
Cld: C 46.88 H 4.85 F 42.02
Fnd: C 46.64 H 4.97 F 41.87 c) 2-(Decyloxy)-4-oxa-1H,1H,2H,3H,3H,5H,5H,6H,6H-perfluorotetradecan-1-ol 20 g (26.02 mmol) of the title compound of Example 13b) is dissolved in 200 ml of isopropanol, and 3 g of palladium catalyst (10% Pd/C) is added. It is hydrogenated overnight at room temperature. The catalyst is filtered off, and the filtrate is evaporated to dryness in a vacuum.

Yield: 17.65 g (quantitative) of a colorless solid
Elementary analysis:
Cld: C 40.72 H 4.61 F 47.60
Fnd: C 40.55 H 4.76 F 47.43 d) 1,2-Epoxy-4-oxa-6-(decyloxy)-8-oxa-1H,1H,2H,3H,3H, 5H,5H,6H,7H,7H,9H,9H,$_1$OH,1OH-perfluorooctadecane 9.25 g (100 mmol) of epichlorohydrin is added in drops to a mixture of 17 g (25.06 mmol) of the title compound of Example 13c) and 2 g (5.89 mmol) of tetrabutylammonium hydrogen sulfate in 300 ml of 60% aqueous potassium hydroxide solution/100 ml of toluene while being stirred vigorously at 10° C., and care is taken to ensure that the temperature of the reaction solution does not exceed 20° C. It is allowed to stir for 2 hours at 15° C., and then 4.63 g (50 mmol) of epichlorohydrin is added in drops as described above. Then, it is stirred overnight at room temperature. 100 ml of toluene and methyl-tert-butyl ether are added, and the aqueous phase is separated. The latter is extracted twice more with 100 ml of toluene each. The organic phases are combined, dried on magnesium sulfate and concentrated by evaporation in a vacuum. The residue is chromatographed on silica gel (mobile solvent: dichloromethane/hexane/acetone=20/10/1).

Yield: 14.91 g (81% of theory) of a colorless solid
Elementary analysis:
Cld: C 42.51 H 4.80 F 43.97
Fnd: C 42.37 H 4.96 F 43.68 e) 10-[2-Hydroxy-4,8-dioxa-6-(decyloxy)-1H,1H, 2H,3H, 3H,5H,5H,6H,7H,7H,9H,9H,10H,10H-perfluorooctadecyl]-1,4,7-tris(carboxymethyl)-1,4,7,10-tetraazacyclododecane 6.11 g (152.8 mmol) of sodium hydroxide is added to 6.6 g (19.06 mmol) of 1,4,7-tris(carboxymethyl)-1,4,7,10-tetraazacyclododecane in 60 ml of water. A solution of 14 g (19.06 mmol) of the title compound of Example 13d), dissolved in 80 ml of n-butanol/40 ml of 2-propanol, is added dropwise to it, and the solution is heated overnight to 80° C. in an autoclave. It is evaporated to dryness in a vacuum, the residue is taken up in 200 ml of water, and it is adjusted to pH 3 with 3N hydrochloric acid. Then, it is extracted twice with 300 ml of n-butanol. The combined butanol phases are evaporated to dryness in a vacuum, and the residue is purified by RP-chromatography (RP-18/mobile solvent: gradient consisting of water/n-butanol/acetonitrile).

Yield: 17.88 g (76% of theory) of a vitreous solid
Water content: 12.5%
Elementary analysis (relative to anhydrous substance):
Cld: C 44.49 H 5.60 F 29.91 N 5.19
Fnd: C 44.31 H 5.75 F 29.70 N 5.03 f) Gadolinium complex of 10-[2-hydroxy-4,8-dioxa-6-(decyloxy)-1H,1H,2H,3H,3H,5H,5H,6H,7H,7H,9H,9H, 10H,10H-perfluorooctadecyl)-1,4,7-tris(carboxymethyl)-1,4,7,10-tetraazacyclododecane 10 g (9.26 mmol) of the title compound of Example 13e) is dissolved in 30 ml of water/10 ml of ethanol/30 ml of chloroform, and 1.68 g (4.63 mmol) of gadolinium oxide is added. It is stirred for 3.5 hours at 90° C. in an autoclave. The solution is filtered and evaporated to dryness in a vacuum.

Yield: 12.39 g (quantitative) of a colorless, vitreous solid
Water content: 7.8%
Elementary analysis (relative to anhydrous substance):
Cld: C 38.93 H 4.66 F 26.17 Gd 12.74 N 4.54
Fnd: C 38.71 H 4.82 F 26.01 Gd 12.55 N 4.38

EXAMPLE 14 a) 1-Phenyl-2-oxa-4,4,4-tris(2-oxa-1H,1H,3H,3H,4H,4H-perfluorodecyl)-butane 2 g (5.89 mmol) of tetrabutylammonium hydrogen sulfate and 22.48 g (562 mmol) of finely powdered sodium hydroxide are added to 4.24 g (18.74 mmol) of pentaerythritol monobenzyl ether and 40 g (93.7 mmol) of lH,lH,2H,2H-perfluorooctyl-1-bromide in 150 ml of toluene. It is stirred for 24 hours at room temperature. The organic phase is separated from the solid and washed twice with 5% aqueous hydrochloric acid each. The organic phase is dried on magnesium sulfate and evaporated to dryness in a vacuum. The residue is chromatographed on silica gel (mobile solvent: n-hexane/acetone=25/1).

Yield: 14.45 g (61% of theory relative to the benzyl ether) of a colorless, waxy solid
Elementary analysis:
Cld: C 34.19 H 2.15 F 58.59
Fnd: C 34.02 H 2.31 F 58.41 b) 2,2,2-Tris(2-oxa-1H,1H,3H,3H,4H,4H-perfluorodecyl)-ethan-1-ol 14 g (11.07 mmol) of the title compound of Example 14a) is dissolved in 100 ml of isopropanol/100 ml of tetrahydrofuran, and 3 g of palladium catalyst (10% Pd/C) is added. It is hydrogenated overnight at room temperature. The catalyst is filtered off, and the filtrate is evaporated to dryness in a vacuum.

Yield: 13 g (quantitative) of a colorless solid
Elementary analysis:
Cld: C 29.66 H 1.80 F 63.09
Fnd: C 29.45 H 1.97 F 62.91 c) 1,2-Epoxy-4-oxa-6,6,6-tris(2-oxa-1H,1H,3H,3H,4H,4H-perfluorodecyl)-hexane 3.94 g (42.57 mmol) of epichlorohydrin is added in drops to a mixture of 12.5 g (10.64 mmol) of the title compound of Example 14b) and 1 g (2.95 mmol) of tetrabutylammonium hydrogen sulfate in 150 ml of 60% aqueous potassium hydroxide solution/50 ml of toluene while being stirred vigorously at 10° C., and care is taken to ensure that the temperature of the reaction solution does not exceed 20° C. It is allowed to stir for 2 hours at 15° C., and then 1.97 g (21.29 mmol) of epichlorohydrin is added in drops as described above. Then, it is stirred overnight at room temperature. 100 ml of toluene and 100 ml of methyl-tert-butyl ether are added, and the aqueous phase is separated. The latter is extracted twice more with 50 ml of toluene each. The organic phases are combined, dried on magnesium sulfate and concentrated by evaporation in a vacuum. The residue is chromatographed on silica gel (mobile solvent: dichloromethane/hexane/acetone 20/10/1).

Yield: 8.12 g (62% of theory) of a colorless solid
Elementary analysis:
Cld: C 31.24 H 2.05 F 60.22
Fnd: C 31.09 H 2.19 F 60.10 d) 10-[2-Hydroxy-4-oxa-6,6,6-tris(2-oxa-1H,1H,3H,3H,4H,4H-perfluorodecyl)-hexyl]-1,4,7-tris(carboxymethyl)-1,4,7,10-tetraazacyclododecane 2.08 g (52 mmol) of sodium hydroxide is added to 2.25 g (6.50 mmol) of 1,4,7-tris(carboxymethyl)-1,4,7,10-tetraazacyclododecane in 30 ml of water. A solution of 8.0 g (6.50 mmol) of the title compound of Example 14c), dissolved in 50 ml of n-butanol/30 ml of 2-propanol, is added dropwise to it, and the solution is heated overnight to 100° C. in an autoclave. It is evaporated to dryness in a vacuum, the residue is taken up in 200 ml of water and adjusted to pH 3 with 3N hydrochloric acid. Then, it is extracted twice with 100 ml of n-butanol. The combined butanol phases are evaporated to dryness in a vacuum, and the residue is purified by RP-chromatography (RP-18/ mobile solvent: gradient consisting of water/n-butanol/ acetonitrile).

Yield: 7.79 g (67% of theory) of a colorless, vitreous solid
Water content: 11.9%
Elementary analysis (relative to anhydrous substance):
Cld: C 35.06 H 3.20 F 47.02 N 3.56
Fnd: C 34.90 H 3.38 F 46.86 N 3.47 e) Gadolinium complex of 10-[2-hydroxy-4-oxa-6,6,6-tris (2-oxa-1H,1H,3H,3H,4H,4H-perfluorodecyl)-hexyl]-1,4,7-tris(carboxymethyl)-1,4,7,10-tetraazacyclododecane 7 g (4.44 mmol) of the title compound of Example 14d) is dissolved in 30 ml of water/50 ml of ethanol/50 ml of chloroform, and 0.80 g (2.22 mmol) of gadolinium oxide is added. It is stirred for 5 hours at 90° C. in an autoclave. The solution is filtered and evaporated to dryness in a vacuum.

Yield: 8.34 g (quantitative) of a colorless, vitreous solid
Water content: 8.1%
Elementary analysis (relative to anhydrous substance):
Cld: C 31.94 H 2.74 F 42.83 Gd 9.09 N 3.24
Fnd: C 31.74 H 2.91 F 42.67 Gd 8.85 N 3.15

EXAMPLE 15 a) 1,7-Bis[acetyl-(2-(N-ethyl-N-perfluorooctylsulfonylamino)]-1,4,7-triazaheptane 20 g (34.17 mmol) of the title compound of Example 1b) and 4.33 g (37.59 mmol) of N-hydroxysuccinimide are dissolved in 150 ml of dimethylformamide. 7.76 g (37.59 mmol) of dicyclohexylcarbodiimide is added at 0° C. and stirred for 3 hours at room temperature. Dicyclohexylurea is filtered out, and the filtrate is added in drops to a solution of 1.76 g (17.09 mmol) of diethylenetriamine and 13.83 g (136.7 mmol) of triethylamine in 200 ml of dimethylformamide at room temperature. It is stirred overnight at room temperature. It is evaporated to dryness in a vacuum, and the residue is taken up in 200 ml of 5% aqueous soda solution. It is extracted twice with 150 ml of dichloromethane each, the combined organic phases are dried on magnesium sulfate and evaporated to dryness in a vacuum. The residue is chromatographed on silica gel (mobile solvent: dichloromethane/2-propanol=20/1).

Yield: 16.5 g (78% of theory) of a waxy solid
Elementary analysis:
Cld: C 27.17 H 2.04 F 52.19 N 5.66 S 5.18
Fnd: C 27.03 H 2.17 F 52.04 N 5.49 S 5.07 b) 4-(3-Carboxy-propanoyl)-1,7-bis-{acetyl-(2-(N-ethyl-N-perfluorooctylsulfonylamino)]}-1,4,7-triazaheptane 3.92 g (38.78 mmol) of triethylamine is added to 16 g (12.93 mmol) of the title compound of Example 15a) in 100 ml of methylene chloride, and the solution is cooled to 0° C. Then, 2.59 g (25.86 mmol) of succinic anhydride is added and stirred for 3 hours at 0° C., overnight at room temperature. 200 ml of 5% aqueous hydrochloric acid is added and shaken well. The organic phase is separated and dried on magnesium sulfate. It is evaporated to dryness in a vacuum, and the residue is chromatographed on silica gel (mobile solvent: dichloromethane/2-propanol=15/1).

Yield: 15.74 g (91% of theory) of a colorless solid
Elementary analysis:
Cld: C 28.73 H 2.19 F 48.29 N 5.24 S 4.79
Fnd: C 28.58 H 2.40 F 48.17 N 5.17 S 4.65 c) 10-[7-Hydroxy-5-aza-4-oxo-octanoic acid-N,N-bis(3-aza-4-oxo-6-aza-6-(perfluorooctylsulfonyl)-octyl)-amide]-1,4,7-tris(carboxymethyl)-1,4,7,10-tetraazacyclododecane 15 g (11.21 mmol) of the title compound of Example 15b) and 1.42 g (12.33 mmol) of N-hydroxysuccinimide are dissolved in a mixture of 80 ml of dimethylformamide/30 ml of chloroform. 2.54 g (12.33 mmol) of dicyclohexylcarbodiimide is added at 0° C. and stirred for 1 hour at 0° C., then for 3 hours at room temperature. It is cooled again to 0° C., and 4.05 g (40 mol) of triethylamine/50 ml of 2-propanol is added. Then, 7.07 g (12.33 mmol) of the gadolinium complex of 10-[2-hydroxy-3-amino-propyl]-1,4,7-tris (carboxymethyl)-1,4,7,10-tetraazacyclododecane, dissolved in 30 ml of water, is added and stirred for 3 hours at room temperature. It is evaporated to dryness, the residue is taken up in a mixture of 100 ml of methanol/50 ml of chloroform, and dicyclohexylurea is filtered out. The filtrate is evaporated to dryness and purified by RP-chromatography (RP-18/mobile solvent: gradient consisting of water/n-propanol/ acetonitrile).

Yield: 17.76 g (78% of theory) of a colorless, vitreous solid
Water content: 6.8%
Elementary analysis (relative to anhydrous substance):
Cld: C 31.08 H 3.03 F 34.12 Gd 8.31 N 7.40 S 3.39
Fnd: C 30.89 H 3.15 F 34.01 Gd 8.14 N 7.25 S 3.24

EXAMPLE 16

Gadolinium complex of 1,4,7-tris (carboxylatomethyl)-10-(2-hydroxy-19,19,20,20,21, 21,22,22,23,23,24,24,25,25,26,26,26-heptadecafluoro-4,7,10,13,16-penta-oxa-hexacosane)-1,4,7,10-tetraazacyclododecane a) 16,16,17,17,18,18,19,19,20,20,21,21,22,22,22-Heptadecafluoro-3,6,9,12-tetra-oxa-docosan-1-ol A mixture of 20 g (32.35 mmol) of 1-p-toluenesulfonyloxy-1H,1H, 2H,2H-perfluorodecane [see Example 7a], 1 g of tetrabutylammonium hydrogen sulfate, 62.83 g (323.5 mmol) of tetraethylene glycol, 300 ml of dichloromethane and 100 ml of 50% sodium hydroxide solution is stirred intensively at about 5° C. for 24 hours. It is then diluted with 200 ml of dichloromethane, the phases are separated, and the dichloromethane phase is washed with water. The organic phase is dried on magnesium sulfate and concentrated by evaporation in a vacuum. 18.5 g of the desired title compound is obtained as light yellow oil.

b) 1,2-Epoxy-19,19,20,20,21,21,22,22,23,23,24,24,25,25, 26,26,26-heptadecafluoro-4,7,10,13,16-penta-oxa-hexacosane A mixture of 17 g (26.5 mol) of 16,16,17,17,18,18,19,19, 20,20,21,21,22,22,22-heptadecafluoro-3,6,9,12-tetra-oxa-docosan-1-ol, 0.5 g of tetrabutylammonium hydrogen sulfate, 2.94 g of epichlorohydrin, 200 ml of dichloromethane and 50 ml of 50% sodium hydroxide solution is stirred intensively at room temperature for 8 hours. The phases are separated, the aqueous phase is shaken with 100 ml of dichloromethane, the organic phases are combined, shaken with 50 ml of water, dried on magnesium sulfate and concentrated by evaporation in a vacuum. The residue is chromatographed on silica gel with hexane/5–50% ethyl acetate, and 12.92 g of the title compound is obtained as oil.

Elementary analysis:
Cld: C 36.22 H 3.62 F 46.38
Fnd: C 36.00 H 3.78 F 46.20 c) 1,4,7-Tris(carboxylatomethyl)-10-(2-hydroxy-19,19,20, 20,21,21,22,22,23,23,24,24,25,25,26,26,26-heptadecafluoro-4,7,10,13,16-penta-oxa-hexacosane)-1, 4,7,10-tetraazacyclododecane A solution of 12.05 g (17.3 mmol) of 1,2-epoxy-19,19, 20,20,21,21,22,22,23,23,24,24,25,25,26,26,26-heptadecafluoro-4,7,10,13,16-penta-oxa-hexacosane in 50 ml of tetrahydrofuran is added to a solution of 6 g (17.3 mmol) of 1,4,7-(triscarboxylatomethyl)-1,4,7,10-tetraazacyclododecane and 4 g of sodium hydroxide in 30 ml of water. It is stirred overnight at 70° C., then largely concentrated by evaporation in a vacuum, the residue is taken up in 150 ml of water and adjusted to pH 3 with 6N hydrochloric acid and extracted several times with n-butanol. The combined extracts are concentrated by evaporation in a vacuum, and the residue is purified by chromatography on RP-18 with a gradient consisting of water/n-butanol/acetonitrile. 13.71 g of the title compound is obtained as yellow viscous oil.

Elementary analysis:
Cld: C 40.31 H 4.93 F 30.97 N 5.37
Fnd: C 40.08 H 5.21 F 30.77 N 5.29 d) Gadolinium complex of 1,4,7-tris(carboxylatomethyl)-10-(2-hydroxy-19,19,20,20,21,21,22,22,23,23,24,24,25, 25,26,26,26-heptadecafluoro-4,7,10,13,16-penta-oxa-hexacosane)-1,4,7,10-tetraazacyclododecane A mixture of 5 g (4.79 mmol) of 1,4,7-tris(carboxylatomethyl)-10-(2-hydroxy-19,19,20,20,21,21,22,22,23,23, 24,24,25,25,26,26,26-heptadecafluoro-4,7,10,13,16-penta-oxa-hexacosane)-1,4,7,10-tetraazacyclododecane, 50 ml of water and 30 ml of ethanol is mixed with 869 mg (2.397 mmol) of gadolinium oxide, and it is refluxed for 5 hours. The hot solution is filtered and concentrated by evaporation in a vacuum. 5.60 g of the title compound is obtained as a vitreous, solid substance with a water content of 4.1%.

Elementary analysis (relative to anhydrous substance):
Cld: C 35.12 H 4.04 F 26.98 Gd 13.14 N 4.68
Fnd: C 34.90 H 4.38 F 26.70 Gd 13.10 N 4.62

EXAMPLE 17

Gadolinium complex of 1,4,7-tris(carboxylatomethyl)-10-(4-aza-2-hydroxy-26,26,26,25,25,24,24,23,23,22,22,21, 21,20,20,19,19-heptadecafluoro-5-oxo-16-thia-hexacosyl)-1,4,7,10-tetraazacyclododecane a) 22,22,22,21,21,20,20,19,19,18,18,17,17,16,16,15,15-Heptadecafluoro-12-thia-docosanoic acid A solution of 10 g (37.71 mmol) of 11-bromoundecanoic acid in 150 ml of dichloromethane is mixed with 11.43 g of triethylamine and 18.11 g (37.71 mmol) of 1H,1H,2H,2H-perfluorodecylmercaptan, and it is stirred overnight at room temperature. The solution is extracted several times with 2N hydrochloric acid, washed with common salt solution, dried on magnesium sulfate and concentrated by evaporation in a vacuum. 21.5 g of the title compound is obtained as yellow oil.

Elementary analysis:
Cld: C 37.96 H 3.79 F 48.61 S 4.83 Fnd: C 38.30 H 4.01 F 48.40 S 5.20 b) Gadolinium complex of 1,4,7-tris(carboxylatomethyl)-10-(4-aza-2-hydroxy-26,26,26,25,25,24,24,23,23,22, 22, 21,21,20,20,19,19-heptadecafluoro-5-oxo-16-thia-hexacosyl)-1,4,7,10-tetraazacyclododecane 5 g (7.52 mmol) of the title compound of Example 17a) and 0.95 g of N-hydroxysuccinimide are dissolved in a mixture of 25 ml of dimethylformamide and 15 ml of chloroform. 1.71 g of dicyclohexylcarbodiimide is added at 0° C. and stirred for 1 hour at 0° C., then for 3 hours at room temperature. It is then cooled again to 0° C. and mixed with 3 ml of triethylamine and 20 ml of n-propanol. Then, 4.75 g (8.27 mmol) of the gadolinium complex of 10-(3-amino-2-hydroxy-propyl)-1,4,7-tris(carboxylatomethyl)-1,4,7,10-tetraazacyclododecane, dissolved in 25 ml of water, is added and stirred for 3 hours at 20° C. It is evaporated to dryness, the residue is taken up in a mixture of 55 ml of methanol and 20 ml of chloroform, and dicyclohexylurea is filtered out. The filtrate is evaporated to dryness and purified by chromatography on RP-18 with a gradient consisting of water/n-propanol/acetonitrile. 6.15 g of the title compound is obtained as a vitreous solid, with a water content of 2.3%.

Elementary analysis (relative to anhydrous substance):
Cld: C 37.41 H 4.38 F 26.47 Gd 12.89 N 5.74 S 2.63 Fnd: C 37.08 H 4.60 F 26.30 Gd 12.68 N 5.91 S 2.49

EXAMPLE 18

Gadolinium complex of 1,4,7-tris(carboxylatomethyl)-10-[1-(1,2-dihydroxyethyl)-3-oxa-6,6,7,7,8,8,9,9,10,10,11, 11,11-tridecafluoro]undecane-1,4,7,10-tetraazacyclododecane a) 1-p-Toluenesulfonyloxy-1H,1H,2H,2H-perfluorooctane 20 ml of pyridine is added to a solution of 25 g (68.7 mmol) of 1H,1H,2H,2H-perfluorooctan-1-ol in 300 ml of dichloromethane at 0° C., and 13.49 g (70.76 mmol) of p-toluenesulfonic acid chloride is added in portions while being stirred. It is stirred for 3 more hours at 0° C., and the dichloromethane is drawn off at room temperature in a vacuum. The remaining pyridine solution is mixed with ice water, whereby the desired product precipitates. The residue is decanted and dissolved in dichloromethane, the solution is washed with water, dried on magnesium sulfate and concentrated by evaporation in a vacuum. The residue is purified by chromatography on silica gel with hexane/5–40% ethyl acetate. 29.2 g of the title compound is obtained as viscous foam.

Elementary analysis: Cld: C 34.76 H 2.14 F 47.65 S 6.19 Fnd: C 34.98 H 2.38 F 47.39 S 6.42 b) 1,4,7-Tris(benzyloxycarbonyl)-10-[1-(2,2-dimethyl-1, 3-dioxolan-4-yl)-6,6,7,7,8,8,9,9,10,10,11,11,11-tridecafluoro-3-oxa]-undecane-1,4,7,10-tetraazacyclododecane 20 ml of 50% sodium hydroxide solution, 0.5 g of tetrabutylammonium hydrogen sulfate and 5.18 g (10 mmol) of 1-p-toluenesulfonyloxy-1H,1H,2H,2H-perfluorooctane [see Example 18a)] are added in succession to 7.33 g (10 mmol) of 1,4,7-tris(benzyloxycarbonyl)-10-[2-hydroxy-1-

(2,2-dimethyl-1,3-dioxolan-4-yl]-ethyl-1,4,7,10-tetraazacyclododecane [J. Mag. Res. Imag. 5, 7–10, (1955)], dissolved in 100 ml of dichloromethane, and the mixture is stirred intensively overnight at room temperature. The phases are separated, the organic phase is washed several times with water, dried on magnesium sulfate and concentrated by evaporation in a vacuum. The residue is purified by chromatography on silica gel with dichloromethane/1–10% ethanol. 8.02 g of the title compound is obtained as viscous oil.

Elementary analysis: Cld: C 53.01 H 5.02 F 23.19 N 5.26 Fnd: C 53.30 H 5.39 F 23.01 N 5.40 c) 1-[1-(2,2-Dimethyl-1,3-dioxolan-4-yl)-6,6,7,7,8,8,9,9,10,10,11,11,11-tridecafluoro-3-oxa]-undecane-1,4,7,10-tetraazacyclododecane A solution of 7 g (6.57 mmol) of 1,4,7-tris(benzyloxycarbonyl)-10-[1-(2,2-dimethyl-1,3-dioxolan-4-yl)-6,6,7,7,8,8,9,9,10,10,11,11,11-tridecafluoro-3-oxa]-undecane-1,4,7,10-tetraazacyclododecane in 100 ml of isopropyl alcohol is mixed with 0.7 g of palladium on carbon (10%), and it is shaken for 3 hours under hydrogen atmosphere. Catalyst is filtered out, and the solution is concentrated by evaporation in a vacuum. 4.20 g of the title compound is obtained as vitreous foam.

Elementary analysis: Cld: C 41.70 H 5.32 F 37.28 N 8.46 Fnd: C 41.61 H 5.57 F 37.10 N 8.59 d) 1,4,7-Tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane 3.36 g (24.15 mmol) of bromoacetic acid in 50 ml of water is dissolved and mixed with 6N sodium hydroxide solution until pH 7 is reached. A solution of 4 g (6.04 mmol) of 1-[1-(2,2-dimethyl-1,3-dioxolan-4-yl)-6,6,7,7,8,8,9,9,10,10,11,11,11-tridecafluoro-3-oxa]-undecane-1,4,7,10-tetraazacyclododecane, dissolved in 20 ml of isopropyl alcohol, and enough 6N sodium hydroxide solution are added in drops at 40° C. while simultaneously being stirred so that the pH is kept at 9–10. Then, it is mixed with semiconcentrated hydrochloric acid up to pH 1 and stirred for another 3 hours at 60° C. It is cooled to room temperature, and the solution is extracted several times with n-butanol. The organic extract is concentrated by evaporation, and the residue is purified by chromatography on RP-18 with a gradient consisting of water/n-butanol/acetonitrile. 3.85 g of the title compound is obtained as yellow oil with a water content of 3.9%.

Elementary analysis (relative to anhydrous substance): Cld: C 39.20 H 4.68 F 31.00 N 7.03 Fnd: C 39.08 H 4.98 F 30.72 N 7.29 e) Gadolinium complex of 1,4,7-tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane A mixture of 1.59 g (2 mmol) of 1,4,7-tris(carboxylatomethyl)-10-[1-(1,2-dihydroxy-ethyl)-3-oxa-6,6,7,7,8,8,9,9,10,10,11,11,11-tridecafluoro]undecane-1,4,7,10-tetraazacyclododecane, 25 ml of water and 15 ml of ethanol is mixed with 363 mg (1 mmol) of gadolinium oxide, and it is refluxed for 5 hours. The hot solution is filtered, concentrated by evaporation in a vacuum, and 1.85 g of the title compound is obtained as a vitreous, solid substance with a water content of 4.2%.

Elementary analysis (relative to anhydrous substance): Cld: C 32.84 H 3.60 F 25.98 Gd 16.54 N 5.89 Fnd: C 32.53 H 3.71 F 25.72 Gd 16.39 N 5.93

EXAMPLE 19

Gadolinium complex of 1,4,7-tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane a) 1-Hydroxy-4-(2H,2H,3H,3H-1-oxa-perfluoroundec-1-yl)-benzene 5 g (45.41 mmol) of hydroquinone is mixed with 100 ml of acetone and mixed while being stirred in succession with 13.8 g of potassium carbonate and 14.04 g (22.7 mmol) of 1-p-toluenesulfonyloxy-1H,1H,2H,2H-perfluorodecane [see Example 7a)]. It is refluxed for 6 hours, then largely concentrated by evaporation in a vacuum, diluted with 200 ml of water, adjusted to pH 3 with citric acid and extracted several times with dichloromethane. The organic extract is dried on magnesium sulfate and concentrated by evaporation in a vacuum. The residue is purified by chromatography on silica gel with hexane/5–30% ethyl acetate. 8.20 g of the desired title compound is obtained as viscous oil.

Elementary analysis: Cld: C 34.55 H 1.63 F 58.07 Fnd: C 34.31 H 1.79 F 58.01 b) 1-(3,4-Epoxy-1-oxa-but-1-yl)-4-(2H,2H,3H,3H-1-oxa-perfluoroundec-1-yl)-benzene A mixture of 8 g (14.38 mmol) of 1-hydroxy-4-(2H,2H,3H,3H-1-oxa-perfluoroundec-1-yl)-benzene, 0.4 g of tetrabutylammonium hydrogen sulfate, 1.60 g (17.26 mmol) of epichlorohydrin, 150 ml of dichloromethane and 30 ml of 50% sodium hydroxide solution is stirred intensively for 30 minutes in an ice bath, then for 5 hours at room temperature. The phases are separated, the organic phase is washed with water, dried on magnesium sulfate and concentrated by evaporation in a vacuum. The residue is purified by chromatography on silica gel with hexane/5–30% ethyl acetate, and 6.60 g of the title compound is obtained as viscous oil.

Elementary analysis: Cld: C 37.27 H 2.41 F 52.75 Fnd: C 37.10 H 2.66 F 52.80 c) 1,4,7-Tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane A solution of 6.12 g (10 mmol) of 1-(3,4-epoxy-1-oxa-but-1-yl)-4-(2H,2H,3H,3H-1-oxa-perfluoroundec-1-yl)-benzene in 25 ml of tetrahydrofuran is added to a solution of 3.46 g (10 mmol) of 1,4,7-tris(carboxylatomethyl)-1,4,7,10-tetraazacyclododecane and 2.5 g of sodium hydroxide in 25 ml of water, and it is refluxed for 24 hours, then largely concentrated by evaporation in a vacuum, the residue is dissolved in 100 ml of water, adjusted to pH 3 with 6N hydrochloric acid and extracted several times with n-butanol. The combined extracts are concentrated by evaporation in a vacuum. The residue is purified by chromatography on RP-18 with a gradient consisting of water/n-butanol/acetonitrile. 6.71 g of the title compound is obtained as viscous oil.

Elementary analysis: Cld: C 41.35 H 4.10 F 33.69 N 5.84 Fnd: C 41.58 H 4.38 F 33.50 N 5.91 d) Gadolinium complex of 1,4,7-tris(carboxylatomethyl)-10-{2-hydroxy-4-oxa-4-[4-(2H,2H,3H, 3H-1-oxa-perfluoroundec-1-yl)]-phenyl}-but-1-yl-1,4,7,10-tetraazacyclododecane A mixture of 4.79 g (5 mmol) of 1,4,7-tris(carboxylatomethyl)-10-{2-hydroxy-4-oxa-4-[4-(2H,2H,3H,3H-1-oxa-perfluoroundec-1-yl)]-phenyl}-but-1-yl-1,4,7,10-tetraazacyclododecane, 50 ml of water and 30 ml of ethanol is mixed with 906 mg (2.5 mmol) of gadolinium oxide and refluxed for 5 hours. The hot solution is filtered and concentrated by evaporation in a vacuum. 5.50 g of the title compound is obtained as a vitreous solid substance with a water content of 4.9%.

Elementary analysis (relative to anhydrous substance): Cld: C 35.62 H 3.26 F 29.02 Gd 14.13 N 5.03 Fnd: C 35.40 H 3.50 F 28.81 Gd 14.01 N 5.18

EXAMPLE 20

Gadolinium complex, disodium salt of 3,9-bis(carboxymethyl)-6-[(1-carboxy)-1H,2H,2H,4H,4H,5H,5H-3-oxa-perfluorotridecyl]-3,6,9-triazaundecanedioic acid a) N-t-Butoxycarbonyl-serine-(1H,1H,2H,2H-perfluorodecyl)-ether-benzyl ester 300 mg (10 mmol) of sodium hydride (80% in oil) is added in portions to a solution of 2.953 g (10 mmol) of N-t-butyloxycarbonyl-serine-benzyl ester (Bachem commercially available products) in 30 ml of dry dimethylformamide. After dissolving is completed, it is mixed with 6.072 g (10 mmol) of the tosylate produced under 7a). It is stirred for 12 hours at room temperature. Then, it is poured into 500 ml of ice water, the product is taken up in dichloromethane, the organic solution is washed with water, dried on sodium sulfate and evaporated to dryness. The residue is purified by chromatography on silica gel. A mixture of dichloromethane with increasing addition of methanol is used as eluant.

The title compound is obtained as syrup.

Yield: 5.902 g (79.6% of theory)

Elementary analysis: Cld: C 40.50 H 3.26 F 43.56 N 1.89 Fnd: C 40.64 H 3.37 F 43.49 N 1.83 b) Serine-(1H,1H,2H,2H-perfluorodecyl)-ether-benzyl ester (as salt of trifluoroacetic acid 7.414 g (10 mmol) of the N-protected compound that is produced under 20a) is dissolved in 50 ml of a mixture of trifluoroacetic acid and dichloromethane at a 2:1 ratio, and it is stirred overnight at room temperature. It is evaporated to dryness, and the remainder of the trifluoroacetic acid is removed by codistillation with ethanol. The title compound is isolated as a salt of trifluoroacetic acid.

Yield: 7.418 g (98.2% of theory)

Elementary analysis: Cld: C 34.98 H 2.27 F 50.30 N 1.85 Fnd: C 34.89 H 2.31 F 50.39 N 1.80 c) 3,9-Bis(t-butoxycarbonylmethyl)-6-[(1-benzyloxycarbonyl)-1H,2H,2H,4H,4H,5H,5H-3-oxa-perfluorotridecyl)-3,6,9-triazaundecanedioic acid-di(t-butyl)-ester 3.777 g (5 mmol) of the amine-trifluoroacetate that is produced under 20b) and 3.523 g (10 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer phase is separated, extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane with increasing addition of methanol is used as eluant. The title compound is obtained as a glass-like solid.

Yield: 3.162 g (53.4% of theory)

Elementary analysis: Cld: C 48.69 H 5.62 F 27.28 N 3.55 Fnd: C 48.82 H 5.72 F 27.37 N 3.50 d) 3,9-Bis(carboxymethyl)-6-[(1-carboxy)-1H,2H,2H,4H,4H,5H,5H-3-oxa-perfluorotridecyl]-3,6,9-triazaundecanedioic acid 5.920 g (5 mmol) of the compound that is produced under 20c) is added to a mixture of 25 ml of trifluoroacetic acid/dichloromethane at a 2:1 ratio. It is allowed to stir overnight at room temperature, then evaporated to dryness, the residue is taken up in 100 ml of 3N hydrochloric acid, refluxed for 3 hours, then evaporated to dryness in a vacuum and taken up in 160 ml of a mixture of water, ethanol and chloroform (10:5:1). The solution is set at a constant pH (about 3) by adding ion exchanger IRA 67 (OH form). It is quickly suctioned off, and the title compound is obtained as a vitreous solid.

Yield: 3.080 g (71.3% of theory)

Water content: 11.3%

Elementary analysis (relative to anhydrous substance): Cld: C 34.53 H 3.25 F 37.15 N 4.83 Fnd: C 34.41 H 3.32 F 37.29 N 4.90 e) Gadolinium complex, disodium salt of 3,9-bis(carboxymethyl)-6-[(1-carboxy)-1H,2H,2H,4H,4H,5H,5H-3-oxa-perfluorotridecyl]-3,6,9-triazaundecanedioic acid 2.941 g (3.0 mmol, relative to 11.3% water content) of the acid that is produced under 20d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. The pH of the solution is then adjusted to 7.2 by adding sodium hydroxide solution. The solution is then concentrated by evaporation, whereby strong foaming can be observed. The residue is codistilled with distilled water. The title compound is obtained as a vitreous solid.

Yield: 3.489 g (quantitative)

Water content: 8.2%

Elementary analysis (relative to anhydrous substance): Cld: C 28.12 H 2.17 F 30.25 Gd 14.73 N 3.94 Na 4.31 Fnd: C 28.25 H 2.26 F 30.40 Gd 14.85 N 3.99 Na 4.38

EXAMPLE 21

Gadolinium complex, monosodium salt of 3,6,9-tris(carboxymethyl)-3,6,9-triazaundecanedioic acid-mono-N-{ethyl-2-amino-[carbonylmethyl-amino-(N-ethyl-N-perfluorooctylsulfonyl)]}-amide a) 3,6,9-Tris(carboxylatomethyl)-3,6,9-triazaundecanedioic acid-mono-N-{ethyl-2-amino-[carbonylmethyl-amino-(N-ethyl-N-perfluorooctylsulfonyl)]}-amide 17.87 g (50 mmol) of diethylenetriaminepentaacetic acid-bis-anhydride is suspended in 200 ml of a mixture of dimethylformamide and dichloromethane at a 4:1 ratio and mixed in portions with the mixture of 3.137 g (5 mmol) of [N-(2-aminoethyl)-N-perfluorooctylsulfonyl]-aminoacetic acid-N-(2-aminoethyl)-amide and 6.50 g (64.2 mmol) of triethylamine while being stirred vigorously. It is allowed to stir for 5 more hours, evaporated to dryness, mixed with 300 ml of ice water, and the pH of the batch is adjusted to about 3 with 3N hydrochloric acid. It is extracted twice with 200 ml of n-butanol each, the organic solutions are combined and concentrated by evaporation. The product is purified by chromatography on silica gel RP-18. Water and tetrahydrofuran are used as eluants. The title compound is obtained as a vitreous solid.

Yield: 2.722 g (54.3% of theory)

Water content: 9.7%

Elementary analysis (relative to anhydrous substance): Cld: C 33.54 H 3.52 F 32.21 N 8.38 S 3.20 Fnd: C 33.65 H 3.60 F 32.14 N 8.51 S 3.29 b) Gadolinium complex, monosodium salt of 3,6,9-tris(carboxymethyl)-3,6,9-triazaundecanedioic acidmono-N-{ethyl-2-amino-[carbonylmethyl-amino-(N-ethyl-N-perfluorooctylsulfonyl)]}-amide 3.259 g (3 mmol, relative to 9.7% water) of the compound that is produced under 21a) is added to 90 ml of a mixture of distilled water and ethanol (2:1). While being stirred, 543.8 mg (1.5 mmol) of gadolinium oxide is added in portions. It is stirred until dissolved, then the pH of the solution is adjusted to 7.2 by adding sodium hydroxide solution, and it is concentrated by evaporation, whereby strong foaming occurs. The residue is codistilled with distilled water. The title compound is obtained as a glass-like solid.

Yield: 3.861 g (quantitative)
Water content: 8.4%

The elementary analysis is relative to anhydrous substance: Cld: C 28.53 H 2.65 F 27.40 Gd 13.34 N 7.13 Na 1.95 S 2.72 Fnd: C 28.61 H 2.68 F 27.48 Gd 13.40 N 7.08 Na 1.99 S 2.76

EXAMPLE 22

Gadolinium complex, monosodium salt of 3,9-bis(carboxymethyl)-6-1H,1H,4H,4H,5H,5H,8H,8H,10H,10H,11H,11H-2,7-dioxo-3,6-diaza-9-oxa-perfluoromonodecyl)-3,6,9-triazaundecanedioic acid a) Glycolic acid-(1H,1H,2H,2H-perfluorodecyl)-ether-N-(2-aminoethyl)-amide 10.44 g (20 mmol) of compound 2b) is dissolved in 80 ml of dichloromethane and mixed with 2.30 g (20 mmol) of N-hydroxysuccinimide as well as 4.13 g (20 mmol) of dicyclohexylcarbodiimide. It is allowed to stir overnight, dicyclohexylurea is filtered out, and the filtrate is stirred in a solution of 60.1 g (1000 mmol) of ethylenediamine in 100 ml of dichloromethane. It is allowed to stir overnight, mixed with 1.5 l of water, and the organic phase is separated. The dichloromethane solution is washed with water, dried on sodium sulfate, evaporated to dryness and the residue is purified by chromatography on silica gel. A mixture of dichloromethane with increasing addition of isopropanol is used as eluant.

Yield: 9.615 g (85.2% of theory)
Elementary analysis: Cld: C 29.80 H 2.32 F 57.24 N 4.96 Fnd: C 29.96 H 2.37 F 57.12 N 5.01 b) Glycolic acid-(1H,1H,2H,2H-perfluorodecyl)-ether-N-[ethyl-2-(benzyloxycarbonyl-aminomethylcarbonylamino)]-amide 2.092 g (10 mmol) of benzyloxycarbonylglycine is dissolved in 15 ml of dichloromethane and mixed with 1.151 g (10 mmol) of N-hydroxysuccinimide as well as 2.063 g (10 mmol) of dicyclohexylcarbodiimide. It is allowed to stir overnight, dicyclohexylurea is filtered out and evaporated to dryness. The residue is purified on silica gel by column chromatography. A mixture of dichloromethane and ethanol is used as eluant. The title compound is obtained as a vitreous solid.

Yield: 6.905 g (91.4% of theory)
Elementary analysis: Cld: C 38.16 H 2.94 F 42.75 N 5.56 Fnd: C 38.28 H 2.98 F 42.82 N 5.50 c) Glycolic acid-(1H,1H,2H,2H-perfluorodecyl)-ether-N-[ethyl-(2-aminomethyl-carboxylamino)-amide 3.777 g (5 mmol) of the compound that is produced under 22b) is hydrogenated in 100 ml of a mixture of tetrahydrofuran and ethanol at a 2:1 ratio in the presence of 0.2 g of Pearlman's catalyst (Pd 20%/C) until 112 ml of hydrogen is taken up. Catalyst is suctioned off, rewashed well with ethanol and evaporated to dryness. The title compound is obtained as a glass-like solid.

Yield: 3.097 g (99.7% of theory)
Elementary analysis: Cld: C 30.93 H 2.60 F 51.98 N 6.76 Fnd: C 30.87 H 2.64 F 52.11 N 6.82 d) 3,9-Bis(t-butyloxycarbonylmethyl)-6-(1H,1H,4H,4H,5H,5H,8H,8H,10H,10H,11H,11H,-2,7-dioxo-3,6-diaza-9-oxa-perfluorononadecyl)3,6,9-triazaundecanedioic acid-bis(t-butylester)

3.107 g (5 mmol) of the amine that is produced under 22c) and 3.523 g (10 mmol) of N,N-bis(t-butyloxycarbonylmethyl)-2-(bromoethyl)-amine are added to a mixture of 10 ml of acetonitrile and 20 ml of phosphate buffer of pH 8 and stirred intensively for 2 hours at room temperature. Then, the buffer phase is separated, it is extracted with 10 ml of acetonitrile, and the latter is added to the organic phase. After 20 ml of fresh buffer is added, it is stirred for 20 more hours at room temperature. The organic phase is separated, it is concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The compound is purified on silica gel by chromatography. Dichloromethane with increasing addition of methanol is used as eluant. The title compound is obtained as a glass-like solid.

Yield: 3.044 g (52.3% of theory)
Elementary analysis: Cld: C 45.40 H 5.71 F 27.75 N 6.02 Fnd: C 45.47 H 5.78 F 27.68 N 6.10 e) 3,9-Bis(carboxymethyl)-6-(1H,1H,4H,4H,5H,5H,8H,8H,10H,10H,11H, 11H-2,7-dioxo-3,6-diaza-9-oxa-perfluoromonodecyl)-3,6,9-triazaundecanedioic acid 5.820 g (5 mmol) of the compound that is produced under 22d) is added to a mixture of 120 ml of trifluoroacetic acid/dichloromethane at a 2:1 ratio. It is allowed to stir overnight at room temperature, evaporated to dryness, the remainder of trifluoroacetic acid is removed by codistillation with ethanol and taken up in 240 ml of a mixture of water, ethanol and chloroform. The solution is set at a constant pH (about 3) by adding ion exchanger IRA-67 (OH— form). It is quickly suctioned off, concentrated by evaporation, and the title compound is obtained as a vitreous solid.

Yield: 3.214 g (68.4% of theory)
Water content: 10.3%
Elementary analysis (relative to anhydrous substance): Cld: C 35.79 H 3.65 F 34.37 N 7.45 Fnd: C 35.90 H 3.72 F 34.31 N 7.51 f) Gadolinium complex, monosodium salt of 3,9-bis(carboxymethyl)-6-(1H,1H,4H,4H,5H,5H,8H,8H,10H,10H,11H,11H-2,7-dioxo-3,6-diaza-9-oxa-perfluorononadecyl)-3,6,9-triaza-undecanedioic acid 3.143 g (3.0 mmol, relative to 10.3% water content) of the acid that is produced under 22e) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, the solution is concentrated by evaporation, whereby strong foaming can be observed. The residue is codistilled with distilled water. The title compound is obtained as a vitreous solid.

Yield: 3.635 g (quantitative)
Water content: 7.9%
Elementary analysis (relative to anhydrous substance): Cld: C 30.14 H 2.71 F 28.95 Gd 14.09 N 6.28 Na 2.06 Fnd: C 30.21 H 2.78 F 29.03 Gd 14.16 N 6.22 Na 2.11

EXAMPLE 23

Gadolinium complex of 3,6,9-tris(carboxymethyl)-3,6,9-triazaundecanedioic acid-bis{N-[2-aminoethyl-(N-ethyl-N-perfluorooctylsulfonyl]-amide} a) N-Ethyl-(2-benzyloxycarbonylamino-ethyl)-perfluorooctylsulfonic acid amide 5.272 g (10 mmol) of perfluorooctylsulfonic acid-N-ethylamide is dissolved in 30 ml of dimethylformamide. With exclusion of moisture, it is mixed with 330 mg (11 mmol) of sodium hydride (80% in oil). After gas generation is completed, the solution of 2.093 g (10 mmol) of N-benzyloxycarbonyl-aziridine is added dropwise to it. It is poured into 300 ml of ice water, extracted with dichloromethane, the organic solution is washed with water, it is dried on sodium sulfate and evaporated to dryness. The residue is chromatographed on silica gel with dichloromethane/methanol. The title compound is a glass-like solid.

Yield: 6.149 g (87.3% of theory)
Elementary analysis: Cld: C 34.10 H 2.43 F 45.85 N 3.98 S 4.55 Fnd: C 34.00 H 2.49 F 45.97 N 4.06 S 4.49 b) N-Ethyl-N-2-(aminoethyl)-perfluorooctylsulfonamide 3.522 g (5 mmol) of the compound that is produced under 23a) is hydrogenated in 100 ml of a mixture of tetrahydrofuran and ethanol at a 2:1 ratio in the presence of 0.2 g of Pearlman's catalyst (Pd 20%/C) until 112 ml of hydrogen is taken up. Catalyst is suctioned off, it is rewashed well with ethanol and evaporated to dryness. The title compound is obtained as an amorphous solid.

Yield: 2.814 g (98.7% of theory)
Elementary analysis: Cld: C 25.27 H 1.94 F 56.64 N 4.91 S 5.62 Fnd: C 25.39 H 1.99 F 56.57 N 4.96 S 5.53 c) 3,6,9-Tris(carboxymethyl)-3,6,9-triazaundecanedioic acid-bis{N-[2-aminoethyl-(N-ethyl-N-perfluorooctylsulfonyl)]-amide}

5.703 g (10 mmol) of the compound that is produced under 23b) as well as 1.518 g (15 mmol) of triethylamine are dissolved in 30 ml of dry dimethylformamide and mixed in portions with 1.787 g (5 mmol) of diethylenetriaminepentaacetic acid-bisanhydride while being stirred and with exclusion of moisture. It is allowed to stir overnight, then concentrated by evaporation, mixed with water, the pH is adjusted to about 3 with 3N hydrochloric acid, and it is extracted twice with 100 ml of n-butanol each. The organic solutions are combined, concentrated by evaporation and subjected to a chromatography on silica gel RP-18. Water and tetrahydrofuran are used as eluant. The title compound is obtained as a glass-like solid.

Yield: 6.172 g (82.4% of theory)
Water content: 9.8%
Elementary analysis (relative to anhydrous substance): Cld: C 30.47 H 2.76 F 43.12 N 6.55 S 4.28 Fnd: C 30.59 H 2.81 F 43.00 N 6.61 S 4.33 d) Gadolinium complex of 3,6,9-tris(carboxymethyl)-3,6,9-triazaundecanedioic acid-bis{N-[2-aminoethyl-(N-ethyl-N-perfluorooctylsulfonyl)]-amide}

6.570 g (4 mmol, relative to 9.8% water content) of the compound that is produced under 23c) is added to a mixture of 120 ml of distilled water, 60 ml of ethanol and 20 ml of chloroform. 725 mg (82.0 mmol) of gadolinium oxide is added in portions while being stirred and heated to 50° C. It is stirred until dissolved, then concentrated by evaporation, whereby strong foaming occurs, and the residue is subjected to codistillation with distilled water. The codistillation is repeated twice. The title compound is obtained as a glass-like solid.

Yield: 7.191 g (quantitative)
Water content: 8.1%
Elementary analysis (relative to anhydrous substance): Cld: C 27.63 H 2.32 F 39.10 Gd 9.52 N 5.93 S 3.88 Fnd: C 27.50 H 2.37 F 39.22 Gd 9.61 N 5.85 S 3.95

EXAMPLE 24

Gadolinium complex of 3,6,9-tris(carboxymethyl)-3,6,9-triazaundecanedioic acid-bis{N-<2-aminoethyl-[glycolic acid-(1H,1H,2H,2H-perfluorodecyl-ether)-amide]>-amide} a) 3,6,9-Tris(carboxymethyl)-3,6,9-triazaundecanedioic acid-bis{N-<2-aminoethyl-glycolic acid-(1H,1H,2H,2H-perfluorodecyl-ether)-amide]>-amide}

6.771 g (12 mmol) of the compound that is produced under Example 22a) as well as 1.821 g (18 mmol) of triethylamine are dissolved in 40 ml of dry dimethylformamide and mixed in portions with 2.144 g (6 mmol) of diethylenetriaminepentaacetic acid-bisanhydride while being stirred and with exclusion of moisture. It is allowed to stir overnight, then concentrated by evaporation, mixed with 20 ml of water, the pH is adjusted to about 3, and it is extracted with 3N hydrochloric acid twice with 150 ml of butanol each. The organic solutions are combined, concentrated by evaporation, and the residue is subjected to a chromatography on silica gel RP-18. Water and tetrahydrofuran are used as eluant. The title compound is obtained as a glass-like solid.

Yield: 6.989 g (78.4% of theory)
Water content: 7.1%
Elementary analysis (relative to anhydrous substance): Cld: C 33.95 H 3.05 F 43.47 N 6.60 Fnd: C 34.06 H 3.11 F 43.40 N 6.67 b) Gadolinium complex of 3,6,9-tris(carboxymethyl)-3,6,9-triazaundecanedioic acid-bis{N-<2-aminoethyl-[glycolic acid-(1H,1H,2H,2H-perfluorodecyl-ether)-amide)>-amide}

4.798 g (3 mmol, relative to 7.1% water) of the compound that is produced under 24a) is added to a mixture of 100 ml of distilled water, 50 ml of ethanol and 20 ml of chloroform. 543.8 mg (1.5 mmol) of gadolinium oxide is added in portions while being stirred and heated to 50° C. It is stirred until dissolved, then concentrated by evaporation, whereby strong foaming occurs. The residue is codistilled several times with distilled water. The title compound is obtained as a glass-like solid.

Yield: 5.285 g (quantitative)
Water content: 6.9%
The elementary analysis is relative to anhydrous substance. Cld: C 30.76 H 2.58 F 39.39 Gd 9.59 N 5.98 Fnd: C 30.87 H 2.65 F 39.51 Gd 9.69 N 6.11

EXAMPLE 25

Gadolinium complex, sodium salt of 3,9-bis(carboxymethyl)-6-[N-(1H,1H,2H,2H-perfluorodecyl)-aminocarbonylmethyl-3,6,9-triazaundecanedioic acid a) N-Benzyloxycarbonylglycine-N-(1H,1H,2H,2H-perfluorodecyl)-amide 7.877 g (15 mmol) of 1H,1H,2H,2H-perfluorodecylamine (J. Fluor. Chem. 55, 85 (1991)) is dissolved in 70 ml of dichloromethane and mixed with 1.726 g (15 mmol) of N-hydroxysuccinimide, 3.095 g (15 mmol) of dicyclohexylcarbodiimide and 3.138 g (15 mmol) of N-benzyloxycarbonylglycine (commercially available products, Bachem). It is allowed to stir overnight, the dicyclohexylurea is filtered off, concentrated by evaporation, and the residue is subjected to column chromatography on silica gel. Mixtures of dichloromethane and ethanol are used as eluant. The title compound is obtained as a solid.

Yield: 8.951 g (91.2% of theory)
Elementary analysis: Cld: C 36.71 H 2.31 F 49.36 N 4.28 Fnd: C 36.87 H 2.39 F 49.51 N 4.37 b) Glycine-N-(1H,1H,2H,2H-perfluorodecyl)-amide 7.594 g (10 mmol) of the compound that is produced under 28a) is dissolved in 150 ml of a mixture of tetrahydrofuran and ethanol at a 2:1 ratio and hydrogenated in the presence of 0.25 g of Pearlman's catalyst (Pd 20%/C) until 224 ml of hydrogen is taken up. Catalyst is suctioned out, rewashed well with ethanol and evaporated to dryness. The title compound is obtained as an amorphous solid.

Yield: 6.21 g (99.3% of theory)

Elementary analysis: Cld: C 25.37 H 1.60 F 56.84 N 4.93 Fnd: C 25.28 H 1.65 F 56.92 N 4.99 c) 3,9-Bis(t-butyloxycarbonylmethyl)-6-N-[1H,1H,2H,2H-perfluorodecyl)-aminocarbonylmethyl-3,6,9-triazaundecanedioic acid-di(t-butylester)

2.841 g (5 mmol) of the amine that is produced under 25b) and 3.875 g (11 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer phase is separated, it is extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane with increasing addition of methanol is used as eluant. The title compound is obtained as a glass-like solid.

Yield: 4.161 g (78.3% of theory)

Elementary analysis: Cld: C 45.20 H 5.59 F 30.39 N 5.27 Fnd: C 45.35 H 5.67 F 30.47 N 5.34 d) 3,9-Bis(carboxymethyl)-6-N-(1H,1H,2H,2H-perfluorodecyl)-aminocarbonylmethyl-3,6,9-triazaundecanedioic acid 4.783 g (4.5 mmol) of the compound that is produced under 25c) is added to a mixture of 100 ml of trifluoroacetic acid/dichloromethane at a 2:1 ratio. It is allowed to stir overnight at room temperature, then evaporated to dryness, the remainder of trifluoroacetic acid is removed by codistillation with ethanol and taken up in 160 ml of a mixture of water, ethanol and chloroform (10:5:1). A pH of about 3 (pH constant) is set by adding ion exchanger IRA-67 (OH- form). It is suctioned off quickly, concentrated by evaporation, and the title compound is obtained as a vitreous solid.

Yield: 3.007 g (79.7% of theory)

Water content: 10.9%

Elementary analysis (relative to anhydrous substance): Cld: C 34.38 H 3.25 F 38.52 N 6.68 Fnd: C 34.29 H 3.33 F 38.65 N 6.77 e) Gadolinium complex, monosodium salt of 3,9-bis(carboxymethyl)-6-N-(1H,1H,2H,2H-perfluorodecyl)-aminocarbonylmethyl)-3,6,9-triazaundecanedioic acid 2.823 g (3.0 mmol, relative to 10.9% water content) of the acid that is produced under Example 25d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution. The solution is concentrated by evaporation. In this case, strong foaming occurs. The residue is codistilled twice with distilled water. The title compound is obtained as a vitreous solid.

Yield: 3.353 g (quant)

Water content: 9.2%

The elementary analysis is relative to anhydrous substance. Cld: C 28.41 H 2.28 F 31.83 Gd 15.50 N 5.52 Na 2.27 Fnd: C 28.51 H 2.33 F 31.76 Gd 15.57 N 5.46 Na 2.35

EXAMPLE 26

Gadolinium complex, disodium salt of 3,6,9-tris(carboxymethyl)-4-[N-1H,1H,2H,2H-perfluorodecyloxy)-benzyl]-3,6,9-triaza-undecanedioic acid a) 3,6,9-Tris-(t-butyloxycarbonylmethyl)-4-[4-(1H,1H,2H,2H-perfluorodecyloxy)-benzyl]-3,6,9-triazaundecanedioic acid-di(t-butylester)

6.131 g (5 mmol) of 3,6,9-tris(t-butyloxycarbonylmethyl)-4-(4-hydroxybenzyl)-3,6,9-triazaundecanedioic acid-di(t-butylester), produced according to PCT WO 88/07521, is added to 50 ml of dry dimethylformamide, and it is mixed in portions with 150 g (5 mmol) of sodium hydride (80% in oil) while being stirred and with exclusion of moisture. After dissolving is completed, it is mixed with 3.092 g (5 mmol) of the tosylate that is produced under Example 7a). It is stirred for 12 hours at 40° C. Then, it is poured into 500 ml of ice water, the product is taken up in dichloromethane, the organic solution is washed with water, dried on sodium sulfate and evaporated to dryness. The residue is purified by chromatography on silica gel. A mixture of dichloromethane, isopropanol, hexane at a 20:1:5 ratio is used as eluant.

The title compound is obtained as an amorphous solid.

Yield: 5.015 g (81.8% of theory)

Elementary analysis: Cld: C 49.96 H 5.92 F 26.34 N 3.43 Fnd: C 50.11 H 6.00 F 26.43 N 3.38 b) 3,6,9-Tris(carboxymethyl)-4-[4-(1H,1H,2H,2H-perfluorodecyloxy)-benzyl]-3,6,9-triazaundecanedioic acid 3.678 g (3 mmol) of the compound that is produced under Example 26a) is dissolved in 100 ml of a mixture of trifluoroacetic acid and dichloromethane at a 2:1 ratio, and it is stirred overnight at room temperature. It is evaporated to dryness, and the remainder of trifluoroacetic acid is removed by codistillation with ethanol. The residue is taken up in 160 ml of a mixture of water, ethanol and chloroform (10:5:1). By adding ion exchanger IRA-67 (OH— form), a pH of about 3 (constant pH) is set. It is quickly suctioned off, concentrated by evaporation, and the title compound is obtained as a vitreous solid.

Yield: 2.357 g (83.1% of theory)

Water content: 11.3%

The elementary analysis is relative to anhydrous substance. Cld: C 39.38 H 3.41 F 34.16 N 4.44 Fnd: C 39.52 H 3.47 F 34.32 N 4.36 c) Gadolinium complex, disodium salt of 3,6,9-tris(carboxymethyl)-4-(N-(1H,1H,2H,2H-perfluorodecyloxy)-benzyl]-3,6,9-triaza-undecanedioic acid 3.145 g (3.0 mmol, relative to 11.3% water content) of the acid that is produced under Example 26b) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, and it is concentrated by evaporation. In this case, strong foaming occurs. The residue is codistilled twice with distilled water. The title compound is obtained as a vitreous solid.

Yield: 3.804 g (quantitative)
Water content: 9.8%
Elementary analysis (relative to anhydrous substance):
Cld: C 32.55 H 2.38 F 28.24 Gd 13.75 N 3.67 Na 4.02 Fnd: C 32.44 H 2.43 F 28.30 Gd 13.66 N 3.71 Na 4.10

EXAMPLE 27

Gadolinium complex of 10-[(-perfluorooctyl-sulfonyl)-piperazin-1-yl-carbonylmethyl]-1,4,7-tris(carboxymethyl)-1,4,7,10-tetraazacyclododecane a) 1-Perfluorooctylsulfonyl-piperazine 34.39 g (398.3 mmol) of piperazine, 50 g (99.6 mmol) of perfluorooctylsulfonyl fluoride and 10.12 g (100 mmol) of triethylamine are heated for 24 hours to 85° C. 500 ml of water is added, and it is extracted twice with 200 ml of dichloromethane each. The organic phase is dried on magnesium sulfate and evaporated to dryness in a vacuum. The residue is chromatographed on silica gel (mobile solvent: dichloromethane/2-propanol=25:1).

Yield: 17.55 g (31% of theory) of a colorless, amorphous solid

Elementary analysis: Cld: C 25.36 H 1.60 F 56.84 N 4.93 S 5.64 Fnd: C 25.15 H 1.80 F 56.65 N 4.81 S 5.70 b) 1-(2-Bromoacetyl)-4-perfluorooctylsulfonyl-piperazine 17 g (29.9 mmol) of the title compound of Example 27a) and 5.1 g (50 mmol) of triethylamine are dissolved in 100 ml of dichloromethane. 9.1 g (44.9 mmol) of bromoacetyl bromide is added in drops at −10° C. within 30 minutes, and it is stirred for 2 hours at 0° C. The solution is poured into 200 ml of 2N hydrochloric acid and stirred well. The organic phase is separated, dried on magnesium sulfate and concentrated by evaporation in a vacuum. The residue is chromatographed on silica gel (mobile solvent: dichloromethane/acetone=20/1).

Yield: 18.55 g (90% of theory) of a slightly yellow-colored waxy solid

Elementary analysis: Cld: C 24.40 H 1.46 F 46.86 N 4.06 S 4.65 Br 11.59 Fnd: C 24.22 H 1.60 F 46.75 N 3.97 S 4.48 Br 11.41 c) 10-[(-Perfluorooctyl-sulfonyl)-piperazin-1-yl-carbonylmethyl]-1,4,7-tris(carboxymethyl)-1,4,7,10-tetraazacyclododecane 4.63 g (13.36 mmol) of 1,4,7-tris(carboxymethyl)-1,4,7,10-tetraazacyclododecane (≙D03A) and 18.5 g (133.6 mmol) of potassium carbonate are added to 17.78 g (20 mmol) of the title compound of Example 27b) in 180 ml of methanol. It is refluxed for 12 hours. The inorganic salts are filtered off, and the filtrate is evaporated to dryness. The residue is taken up in 100 ml of water and adjusted to pH 3 with 5N hydrochloric acid. It is extracted twice with 150 ml of n-butanol. The combined organic phases are evaporated to dryness in a vacuum, and the residue is purified by RP-chromatography (RP-18/mobile solvent=gradient consisting of water/n-butanol/acetonitrile).

Yield: 12.79 g (67% of theory) of a colorless solid
Water content: 8.5%
Elementary analysis (relative to anhydrous substance):
Cld: C 35.23 H 3.70 F 33.83 N 8.80 S 3.36 Fnd: C 35.17 H 3.81 F 33.67 N 8.65 S 3.18 d) Gadolinium complex of 10-[(-perfluorooctyl-sulfonyl)-piperazin-1-yl-carbonylmethyl]-1,4,7-tris(carboxymethyl)-1,4,7,10-tetraazacyclododecane 10 g (10.47 mmol) of the title compound of Example 27c) is dissolved in a mixture of 50 ml of water/20 ml of ethanol, and 1.90 g (5.23 mmol) of gadolinium oxide is added. It is stirred for 4 hours at 80° C. The solution is filtered and evaporated to dryness in a vacuum.

Yield: 12.2 g (quantitative)
Water content: 5.1%
Elementary analysis (relative to anhydrous substance):
Cld: C 30.33 H 2.91 F 29.13 Gd 14.18 S 2.89 Fnd: C 30.39 H 2.81 F 29.02 Gd 14.01 S 2.78

EXAMPLE 28

Gadolinium complex, monosodium salt of 3,9-bis(carboxymethyl)-6-((4-perfluorooctylsulfonyl)-piperazine-1-carbonylmethyl]-3,6,9-triazaundecanedioic acid a) 1-(2-Benzyloxycarbonylamino)-methyl-carboyl-4-(perfluorooctylsulfonyl)-piperazine 8.524 g (15 mmol) of the piperazine derivative that is produced under 27a) is dissolved in 80 ml of dichloromethane and mixed with 1.726 g (15 mmol) of N-hydroxysuccinimide, 3.095 g (15 mmol) of dicyclohexylcarbodiimide and 3.138 g (15 mmol) of N-benzyloxycarbonylglycine (commercially available products, Bachem). It is allowed to stir overnight, the dicyclohexylurea is filtered off, concentrated by evaporation, and the residue is subjected to column chromatography on silica gel. Mixtures of dichloromethane and ethanol are used as eluant. The title compound is obtained as a solid.

Yield: 10.16 g (89.2% of theory)
Elementary analysis: Cld: C 34.79 H 2.39 F 42.53 N 5.53 S 4.22 Fnd: C 34.60 H 2.43 F 42.65 N 5.66 S 4.17 b) 1-(2-Amino)-acetyl-4-(perfluorooctyl)-sulfonyl-piperazine 7.594 g (10 mmol) of the compound that is produced under 28a) is dissolved in 150 ml of a mixture of tetrahydrofuran and ethanol at a 2:1 ratio, and it is hydrogenated in the presence of 0.25 g of Pearlman's catalyst (Pd 20%/C) until 224 ml of hydrogen is taken up. Catalyst is suctioned out, rewashed well with ethanol and evaporated to dryness. The title compound is obtained as an amorphous solid.

Yield: 6.21 g (99.3% of theory)
Elementary analysis: Cld: C 26.89 H 1.93 F 51.65 N 6.72 S 5.13 Fnd: C 27.03 H 1.97 F 51.77 N 6.58 S 5.20 c) 3,9-Bis(t-butyloxycarbonylmethyl)-6-[(4-perfluorooctylsulfonyl)-piperazine-1-carbonylmethyl]-3,6,9-triazaundecanedicarboxylic acid-di(t-butylester)

3.127 g (5 mmol) of the amine that is produced under 28b) and 3.875 g (11 mmol) of N,N-bis(t-butyloxycarbonylmethyl)-2-(bromoethyl)-amine are added to a mixture of 10 ml of acetonitrile and 20 ml of phosphate buffer of pH 8.0, and it is stirred intensively at room temperature for 2 hours. Then, the buffer is separated, extracted with 10 ml of acetonitrile, and the latter is added to the organic phase. After 20 ml of fresh buffer is added, it is stirred for 20 more hours at room temperature. The organic phase is separated, concentrated by evaporation, and the residue is dispersed between 100 ml of phosphate buffer (pH 8.0) and 100 ml of ethyl acetate. The organic phase is washed with saturated common salt solution, dried on sodium sulfate and concentrated by evaporation. The title compound is purified by chromatography on silica gel. Dichloromethane with increasing addition of methanol is used as eluant. The title compound is obtained as a glass-like solid.

Yield: 4.481 g (76.3% of theory)
Elementary analysis: Cld: C 43.71 H 5.42 F 27.99 N 4.85 S 2.78 Fnd: C 43.84 H 5.47 F 28.10 N 5.00 S 2.69 d) 3,9-Bis(carboxymethyl)-6-f(4-perfluorooctyl-sulfonyl)-piperazin-1-yl-carbonylmethyl]-3,6,9-triazaundecanedioic acid 5.193 g (4.5 mmol) of the compound that is produced under 28c) is added to a mixture of 100 ml of trifluoroacetic acid/dichloromethane at a 2:1 ratio. It is allowed to stir overnight at room temperature, then evaporated to dryness, the remainder of the trifluoroacetic acid is removed by codistillation with ethanol and taken up in 160 ml of a mixture of water, ethanol and chloroform (10:5:1). A pH of about 3 (constant pH) is set by adding ion exchanger IRA-67 (OH— form). It is quickly suctioned off, concentrated by evaporation, and the title compound is obtained as a vitreous solid.

Yield: 3.718 g (79.2% of theory)
Water content: 10.9%
Elementary analysis (relative to anhydrous substance):
Cld: C 33.59 H 3.25 F 34.74 N 6.03 S 3.45 Fnd: C 33.69 H 3.36 F 34.82 N 6.10 S 3.38 e) Gadolinium complex, monosodium salt of 3,9-bis(carboxymethyl)-6-[(4-perfluorooctylsulfonyl)-piperazine-1-carbonylmethyl]-3,6,9-triazaundecanedioic acid 3.13 g (3.0 mmol, relative to 10.9% water content) of the acid that is produced under Example 28d) is added to a mixture of 60 ml of distilled water and 30 ml of ethanol. 543.8 mg (1.5 mmol) of gadolinium oxide is added in portions while being stirred and heated to 50° C. After addition is completed, it is stirred until dissolved. Then, the pH of the solution is adjusted to 7.2 by adding sodium hydroxide solution, and it is concentrated by evaporation. In this case, strong foaming occurs. The residue is codistilled twice with distilled water. The title compound is obtained as a vitreous solid.

Yield: 3.678 g (quantitative)
Water content: 9.2t
Elementary analysis (relative to anhydrous substance):
Cld: C 28.24 H 2.37 F 29.21 Gd 14.22 N 5.07 Na 2.08 S 2.90 Fnd: C 28.36 H 2.41 F 29.14 Gd 14.30 N 5.15 Na 2.12 S 2.83

EXAMPLE 29

Gadolinium complex of 3,6,9-tris(carboxymethyl)-3,6,9-triazaundecanedioic acid-bis[(4-perfluorooctylsulfonyl)-piperazine]-amide a) 3,6,9-Tris(carboxymethyl)-3,6,9-triazaundecanedioic acid-bis[(4-perfluorooctylsulfonyl)-piperazine]-amide 5.683 g (10 mmol) of the compound that is produced under 27a) as well as 1.518 g (15 mmol) of triethylamine are dissolved in 30 ml of dry dimethylformamide and mixed in portions with 1.787 g (5 mmol) of diethylenetriaminepentaacetic acid-bisanhydride while being stirred and with exclusion of moisture. It is allowed to stir overnight, then concentrated by evaporation, mixed with water, the pH is adjusted to about 3 with 3N hydrochloric acid, and it is extracted twice with 100 ml of n-butanol each. The organic solutions are combined, concentrated by evaporation and subjected to a chromatography on silica gel RP-18. Water and tetrahydrofuran are used as eluant. The title compound is obtained as a glass-like solid.

Yield: 6.741 g (81.4% of theory)
Water content: 9.8%
Elementary analysis (relative to anhydrous substance):
Cld: C 30.55 H 2.50 F 43.24 N 6.56 S 4.29 Fnd: C 30.67 H 2.55 F 43.33 N 6.49 S 4.21 b) Gadolinium complex of 3,6,9-tris(carboxymethyl)-3,6,9-triazaundecanedioic acid-bis[(4-perfluorooctylsulfonyl)-piperazine]-amide 6.570 g (4 mmol, relative to 9.8% water content) of the compound that is produced under 23c) is added to a mixture of 120 ml of distilled water, 60 ml of ethanol and 20 ml of chloroform. 725 mg (82.0 mmol) of gadolinium oxide is added in portions while being stirred and heated to 50° C. It is stirred until dissolved, then concentrated by evaporation, whereby strong foaming occurs, and the residue is subjected to codistillation with distilled water. Codistillation is repeated twice. The title compound is obtained as a glass-like solid.

Yield: 7.191 g (quantitative)
Water content: 8.1%
Elementary analysis (relative to anhydrous substance):
Cld: C 27.69 H 2.08 F 39.19 Gd 9.54 N 5.95 S 3.89 Fnd: C 27.83 H 2.15 F 39.10 Gd 6.91 N 6.03 S 3.88

EXAMPLE 30 a) 11-[N-Ethyl-N-(perfluorooctylsulfonyl)-amino]undecanoic acid benzyl ester 20 g (37.94 mmol) of N-ethyl-N-perfluorooctylsulfonamide and 15.73 g (113.8 mmol) of potassium carbonate are suspended in 200 ml of acetone, and 26.96 g (75.87 mmol) of 11-bromoundecanoic acid benzyl ester is added in drops at 60° C. It is stirred for 3 hours at 60° C. The salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 26.46 g (87% of theory) of a colorless, crystalline powder
Elementary analysis: Cld: C 41.95 H 4.02 N 1.75 F 40.29 S 4.00 Fnd: C 41.78 H 4.17 N 1.68 F 40.12 S 3.88 b) 11-N-Ethyl-N-(perfluorooctylsulfonyl)-aminoundecanoic acid 20 g (24.95 mmol) of the title compound of Example 30a) is dissolved in 300 ml of isopropanol/200 ml of dichloromethane, and 3 g of palladium catalyst (10% Pd/C) is added. It is hydrogenated overnight at room temperature. Catalyst is filtered out, and the filtrate is evaporated to dryness in a vacuum. The residue is recrystallized from ether/hexane.

Yield: 16.69 g (94% of theory) of a colorless, crystalline solid.
Elementary analysis: Cld: C 35.45 H 3.68 N 1.97 F 45.39 S 4.51 Fnd: C 35.31 H 3.81 N 1.85 F 45.25 S 4.42 c) Gadolinium complex of 10-[2-hydroxy-4-aza-5-oxo-16-aza-16-(perfluorooctylsulfonyl-octadecyl]-1,4,7-tris(carboxymethyl)-1,4,7,10-tetraazacyclododecane 12.16 g (17.09 mmol) of the title compound of Example 30b) and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C. and stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of gadolinium complex of 10-(3-amino-2-hydroxypropyl) 1,4,7-tris (carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient of water/N-propanol/acetonitrile).

Yield: 16.82 g (71% of theory) of a colorless, vitreous solid.

Water content: 8.6%

Elementary analysis (relative to anhydrous substance):
Cld: C 36.02 H 4.30 F 25.49 Gd 12.41 N 6.63 S 2.53 Fnd: C 35.87 H 4.45 F 25.28 Gd 12.29 N 6.50 S 2.41 d) 10-[2-Hydroxy-4-aza-5-oxo-16-aza-16-(perfluorooctylsulfonyl-octadecyl]-1,4,7-tris(carboxymethyl)-1,4,7,10-tetraazacyclododecane 11.1 g (8.76 mmol) of the title compound of Example 30c) is dissolved in a mixture of 100 ml of water/100 ml of ethanol, and 1.73 g (13.71 mmol) of oxalic acid-dihydrate is added. It is heated for 8 hours to 80° C. It is cooled to 0° C., and precipitated gadolinium oxalate is filtered out. The filtrate is evaporated to dryness, and the residue is purified on RP-18 (RP-18/mobile solvent: gradient consisting of water/i-propanol/acetonitrile).

Yield: 9.80 g (92% of theory) of a vitreous solid.

Water content: 8.5%

Elementary analysis (relative to anhydrous substance):
Cld: C 41.01 H 5.16 F 29.02 N 7.55 S 2.88 Fnd: C 40.87 H 5.31 F 28.85 N 7.40 S 2.73 e) Ytterbium complex of 10-[2-hydroxy-4-aza-5-oxo-16-aza-16-(perfluorooctylsulfonyl-octadecyl)-1,4,7-tris(carboxymethyl)-1,4,7,10-tetraazacyclododecane 1.33 g (2.53 mmol) of ytterbium carbonate is added to 5.64 g (5.07 mmol) of the title compound of Example 30d) in 100 ml of water/50 ml of ethanol, and it is stirred for 3 hours at 80° C. The solution is filtered, and the filtrate is evaporated to dryness in a vacuum.

Yield: 7.08 g (quantitative) of a vitreous solid.

Water content: 8.1%

Elementary analysis (relative to anhydrous substance):
Cld: C 35.58 H 4.24 F 25.17 N 6.55 S 2.50 Yb 13.49 Fnd: C 35.43 H 4.37 F 25.05 N 6.48 S 2.39 Yb 13.35 f) Dysprosium complex of 10-[2-hydroxy-4-aza-5-oxo-16-aza-16-(perfluorooctylsulfonyl-octadecyl)-1,4,7-tris(carboxymethyl)-1,4,7,10-tetraazacyclododecane 0.95 g (2.53 mmol) of dysprosium oxide is added to 5.64 g (5.07 mmol) of the title compound of Example 30d) in 100 ml of water/50 ml of ethanol, and it is stirred for 3 hours at 80° C. The solution is filtered, and the filtrate is evaporated to dryness in a vacuum.

Yield: 7.10 g (quantitative) of a colorless, vitreous solid.

Water content: 9.1%

Elementary analysis (relative to anhydrous substance):
Cld: C 35.87 H 4.28 F 25.38 N 6.60 S 2.52 Dy 12.77 Fnd: C 35.69 H 4.39 F 25.18 N 6.49 S 2.43 Dy 12.70

EXAMPLE 31 a) 11,11,11,10,10,9,9,8,8,7,7-Tridecafluoro-3-oxaundecanoic acid-tert-butyl ester 19.51 g (100.0 mmol) of bromoacetic acid-tert-butyl ester is added in drops to a mixture of 27.57 g (75.73 mmol) of 1H,1H,2H,2H-perfluorooctan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for one hour at 0° C., the organic phase is separated, and the aqueous phase is extracted twice with 50 ml of toluene. The combined organic extracts are dried on sodium sulfate and concentrated by evaporation in a vacuum. The residue is chromatographed on silica gel (mobile solvent: dichloromethane).

Yield: 28.97 g (80% of theory) of a colorless oil.

Elementary analysis: Cld: C 35.16 H 3.16 F 51.64 Fnd: C 35.08 H 3.20 F 51.70 b) 11,11,11,10,10,9,9,8,8,7,7-Tridecafluoro-3-oxaundecanoic acid 25.29 g (52.88 mmol) of the title compound of Example 1a) is dissolved in 300 ml of trifluoroacetic acid, and it is stirred overnight at room temperature. It is evaporated to dryness in a vacuum, and the residue is recrystallized from hexane/diethyl ether.

Yield: 20.54 g (92% of theory) of a colorless, crystalline solid.

Elementary analysis: Cld: C 28.45 H 1.67 F 58.51 Fnd: C 28.36 H 1.60 F 58.62 c) Gadolinium complex of 10-[2-hydroxy-4-aza-5-oxo-7-oxa-10,10,11,11,12,12,13,13,14,14,15,15,15-tridecafluoro-pentadecyl]-1,4,7-tris(carboxymethyl)-1,4,7,10-tetraazacyclododecane 7.21 g (17.09 mmol) of the title compound of Example 31b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxypropyl)- 1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 12.68 g (71% of theory) of a colorless, vitreous solid.

Water content: 6.4%

Elementary analysis (relative to anhydrous substance):
Cld: C 33.16 H 3.61 F 25.26 Gd 16.08 N 7.16 Fnd: C 32.85 H 3.84 F 25.01 Gd 15.87 N 7.03

EXAMPLE 32 a) 15,15,15,14,14,13,13,12,12,11,11,10,10,9,9,8,8-7,7-Henicosafluoro-3-oxapenta-decanoic acid-tert-butyl ester 19.51 g (100.0 mmol) of bromoacetic acid-tert-butyl ester is added in drops to a mixture of 42.72 g (75.73 mmol) of 1H,1H,2H,2H-perfluorooctan-1-ol and 2.57 g (7.57 mmol) of tetrabutylammonium hydrogen sulfate in 300 ml of 60% aqueous potassium hydroxide solution/200 ml of toluene while being stirred vigorously at 0° C. It is stirred for one hour at 0° C., the organic phase is separated, and the aqueous phase is extracted twice with 50 ml of toluene. The combined organic extracts are dried on sodium sulfate and concentrated by evaporation in a vacuum. The residue is chromatographed on silica gel (mobile solvent: dichloromethane).

Yield: 42.12 g (82% of theory) of a colorless oil.

Elementary analysis: Cld: C 31.87 H 2.23 F 58.82 Fnd: C 31.73 H 2.20 F 58.90 b) 15,15,15,14,14,13,13,12,12,11,11,10,10,9,9,8,8,7,7-Henicosafluoro-3-oxapentadecanoic acid-tert-butyl ester 35.87 g (52.88 mmol) of the title compound of Example 1a) is dissolved in 300 ml of trifluoroacetic acid, and it is stirred overnight at room temperature. It is evaporated to dryness in a vacuum, and the residue is recrystallized from hexane/diethyl ether.

Yield: 30.60 g (93% of theory) of a colorless, crystalline solid.

Elementary analysis: Cld: C 27.03 H 1.13 F 64.12 Fnd: C 26.91 H 1.20 F 64.02 c) Gadolinium complex of 10-[2-hydroxy-4-aza-5-oxo-7-oxa-10,10,11,11,12,12,13,13,14,14,15,15,16,16,17,17,18,18,19,19, 19-henicosafluoro-nonadecyl]-1,4,7-tris(carboxymethyl)-1,4,7-tris(carboxymethyl)-1,4,7,10-tetraazacyclododecane 10.63 g (17.09 mmol) of the title compound of Example 32b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 14.73 g (69% of theory) of a colorless, vitreous solid.

Water content: 5.7%

Elementary analysis (relative to anhydrous substance): Cld: C 31.61 H 2.99 F 33.87 Gd 13.35 N 5.95 Fnd: C 31.49 H 3.15 F 33.68 Gd 13.21 N 6.01

EXAMPLE 33 a) N-(2-Bromopropionyl)glycine-benzyl ester 55.9 g (326.1 mmol) of 2-bromopropionic acid chloride is added in drops to 100 g (296.4 mmol) of glycine benzyl ester-p-toluenesulfonic acid salt and 33.0 g (326.1 mmol) of triethylamine in 400 ml of methylene chloride at 0° C. The temperature is not allowed to exceed 5° C. After the addition is completed, it is stirred for one hour at 0° C., then for 2 hours at room temperature. 500 ml of ice water is added, and the water phase is adjusted to pH 2 with 10% aqueous hydrochloric acid. The organic phase is separated and washed once each with 300 ml of 5% aqueous soda solution and 400 ml of water. The organic phase is dried on magnesium sulfate and evaporated to dryness in a vacuum. The residue is recrystallized from diisopropyl ether.

Yield: 68.51 g (75% of theory) of a colorless, crystalline powder

Melting point: 69–70° C.

Elementary analysis: Cld: C 48.02 H 4.70 N 4.67 Br 26.62 Fnd: C 47.91 H 4.82 N 4.51 Br 26.47 b) 1-[4-(Benzyloxycarbonyl)-1-methyl-2-oxo-3-azabutyl]-1,4,7,10-tetraazacyclododecane 50 g (162.2 mmol) of the title compound of Example 1a) is added to 55.8 g (324.4 mmol) of 1,4,7,10-tetraazacyclododecane, dissolved in 600 ml of chloroform, and it is stirred overnight at room temperature. 500 ml of water is added, the organic phase is separated, and it is washed twice with 400 ml of water in each case. The organic phase is dried on magnesium sulfate and evaporated to dryness in a vacuum. The residue is chromatographed on silica gel (mobile solvent: chloroform/methanol/aqueous 25% ammonia=10/5/1).

Yield: 40.0 g [63% of theory relative to 1a) used] of a light yellowish viscous oil.

Elementary analysis: Cld: C 61.36 H 8.50 N 17.39 Fnd: C 61.54 H 8.68 N 17.68 c) 10-[4-(Benzyloxycarbonyl)-1-methyl-2-oxo-3-azabutyl]-1,4,7-tris(tert-butoxy-carbonylmethyl)-1,4,7,10-tetraazacyclododecane (sodium bromide complex)

33 g (169 mmol) of bromoacetic acid-tert-butyl ester is added to 20 g (51.08 mmol) of the title compound of Example 1b) and 17.91 g (169 mmol) of sodium carbonate in 300 ml of acetonitrile, and it is stirred for 24 hours at 60° C. It is cooled to 0° C., salts are filtered out, and the filtrate is evaporated to dryness. The residue is chromatographed on silica gel (mobile solvent: ethyl acetate/ethanol: 15/1). The fractions that contain the product are concentrated by evaporation, and the residue is recrystallized from diisopropyl ether.

Yield: 34.62 g (81% of theory) of a colorless, crystalline powder

Melting point: 116–117° C.

Elementary analysis: Cld: C 54.54 H 7.59 N 8.37 Na 2.74 Br 9.56 Fnd: C 54.70 H 7.65 N 8.24 Na 2.60 Br 9.37 d) 10-(4-Carboxy-1-methyl-2-oxo-3-azabutyl)-1,4,7-tris(tert-butoxycarbonylmethyl)-1,4,7,10-tetraazacyclododecane (sodium bromide complex)

30 g (35.85 mmol) of the title compound of Example 1c is dissolved in 500 ml of isopropanol, and 3 g of palladium catalyst (10% Pd/C) is added. It is hydrogenated overnight at room temperature. Catalyst is filtered out, the filtrate is evaporated to dryness in a vacuum and recrystallized from acetone.

Yield: 22.75 g (85% of theory) of a colorless, crystalline powder

Melting point: 225° C. (decomposition)

Elementary analysis: Cld: C 49.86 H 7.69 N 9.38 Na 3.07 Br 10.71 Fnd: C 49.75 H 7.81 N 9.25 Na 2.94 Br 10.58 e) 10-[1-Methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane 10 g (13.39 mmol) of the title compound of Example 33d and 7.61 g (13.39 mmol) of the title compound of Example 27a are dissolved in 150 ml of tetrahydrofuran. 3.97 g (16.07 mmol) of N-ethoxycarbonyl-2-ethoxy-1,2-dihydroquinoline (EEDQ) is added at 0° C., stirred for 3 hours at 0° C., then for 12 hours at room temperature. It is evaporated to dryness in a vacuum. The residue is taken up in 150 ml of trifluoroacetic acid and stirred for 12 hours at room temperature. It is evaporated to dryness, the residue is dissolved in water and adjusted to pH 3.2 with 10% aqueous sodium hydroxide solution. For purification, it is chromatographed on RP-18 (gradient consisting of water/acetonitrile/tetrahydrofuran).

Yield: 9.67 g (63% of theory) of a hygroscopic solid.

Water content: 10.5%

Elementary analysis (relative to anhydrous substance): Cld: C 36.30 H 3.93 N 9.56 F 31.49 S 3.13 Fnd: C 36.14 H 3.98 N 9.40 F 31.67 S 3.02 f) Gadolinium complex of 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane 5 g (4.87 mmol) of the title compound of Example 33e is dissolved in 60 ml of water, and 0.883 g (2.44 mmol) of gadolinium oxide is added. It is stirred for 3 hours at 90° C. The solution is filtered, and the filtrate is freeze-dried.

Yield: 6.47 g (quantitative) of a voluminous, amorphous powder

Water content: 11.3%

Elementary analysis (relative to anhydrous substance): Cld: C 31.56 H 3.16 N 8.31 F 27.37 S 2.72 Gd 13.33 Fnd: C 31.37 H 3.35 N 8.18 F 27.19 S 2.92 Gd 13.05

EXAMPLE 34 a) 4-Perfluorooctanesulfonylpiperazin-1-ylpentanediamic acid

A solution of 10.62 g (105.0 mmol) of triethylamine and 59.67 g (105.0 mmol) of the title compound of Example 27a) in 50 ml of tetrahydrofuran are added in drops to a suspension of 11.41 g (100.0 mmol) of glutaric anhydride in 100 ml of tetrahydrofuran while being stirred vigorously at 0° C., and it is allowed to come to room temperature overnight. The reaction mixture is acidified with 100 ml of 2N HCl and extracted three times with 100 ml of tetrahydrofuran. The combined organic extracts are dried with sodium sulfate, filtered and concentrated by evaporation. The residue is recrystallized from 2-propanol/ethyl acetate.

Yield: 52.30 g (73% of theory) of a colorless, crystalline solid.

Elementary analysis: Cld: C 29.92 H 2.22 N 4.11 F 47.33 S 4.70 Fnd: C 29.90 H 2.18 N 4.07 F 47.42 S 4.79 b) Gadolinium complex of 10-[2-hydroxy-4-aza-5,9-dioxo-9-{4-perfluorooctyl)-piperazin-1-yl}-nonyl]-1,4,7-tris(carboxymethyl)-1,4,7-tris(carboxymethyl)-1,4,7,10-tetraazacyclododecane 11.66 g (17.09 mmol) of the title compound of Example 34a and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxypropyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18/mobile solvent: gradient consisting of water/n-propanol/acetonitrile).

Yield: 16.7 g (73% of theory) of a colorless, vitreous solid.

Water content: 7.5%

Elementary analysis (relative to anhydrous substance): Cld: C 32.99 H 3.50 F 26.09 Gd 12.70 N 7.92 S 2.59 Fnd: C 32.75 H 3.68 F 25.88 Gd 12.55 N 7.84 S 2.63

EXAMPLE 35 a) N-Benzylperfluorooctanesulfonamide 50.21 g (100.0 mmol) of perfluorooctanesulfonyl fluoride is added in drops to a mixture of 10.62 g (105.0 mmol) of triethylamine and 10.72 g (100.0 mmol) of benzylamine at 80° C. while being stirred vigorously. It is stirred for 2 days at 80° C., the reaction mixture is mixed with 300 ml of water and extracted 3 times with ethyl acetate. The combined organic extracts are dried on sodium sulfate, filtered and concentrated by evaporation. The residue is chromatographed on silica gel (mobile solvent: dichloromethane/methanol=4/1).

Yield: 45.96 g (78% of theory) of a colorless liquid

Elementary analysis: Cld: C 30.57, H 1.37, N 2.38, S 5.44, F 54.81 Fnd: C 30.49 H 1.30, N 2.42, S 5.50, F 54.90 b) N-Benzyl-N-(perfluorooctylsulfonyl)-aminoacetic acid-t-butyl ester 22.4 g (37.94 mmol) of the title compound of Example 35a and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 24.02 g (90% of theory) of a waxy, colorless solid

Elementary analysis: Cld: C 35.86, H 2.58, N 1.99, S 4.56, F 45.91 Fnd: C 35.67 H 2.71, N 2.13, S 4.45, F 45.83 c) N-Benzyl-N-(perfluorooctylsulfonyl)-aminoacetic acid 20 g (28.43 mmol) of the title compound of Example 35b is dissolved in 200 ml of trifluoroacetic acid, and it is stirred overnight at room temperature. It is evaporated to dryness in a vacuum. The residue is recrystallized from methanol/ether.

Yield: 17.48 g (95% of theory) of a colorless, crystalline solid

Elementary analysis: Cld: C 31.54, H 1.56, N 2.16, S 4.95, F 49.89 Fnd: C 31.38 H 1.70, N 2.05, S 4.87, F 49.71 d) Gadolinium complex of 10-[2-hydroxy-4-aza-5-oxo-7-aza-7-(perfluorooctylsulfonyl)-8-phenyl-octyl]-1,4,7-tris(carboxymethyl)-1,4,7,10-tetraazacyclododecane 11.06 g (17.09 mmol) of the title compound of Example 35c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added and stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 16.49 g (75% of theory) of a colorless, vitreous solid

Water content: 6.5%

Elementary analysis: Cld: C 33.95, H 3.18, N 6.99, S 2.67, F 26.85, Gd 13.07 Fnd: C 33.81 H 3.24, N 6.82, S 2.54, F 26.64 Gd 12.91

EXAMPLE 36 a) N-Decylperfluorooctanesulfonamide 50.21 g (100.0 mmol) of perfluorooctanesulfonyl fluoride is added in drops to a mixture of 10.62 g (105.0 mmol) of triethylamine and 15.73 g (100.0 mmol) of decylamine at 80° C. while being stirred vigorously. It is stirred for 2 days at 80° C., the reaction mixture is mixed with 300 ml of water and extracted three times with ethyl acetate. The combined organic extracts are dried on sodium sulfate, filtered and concentrated by evaporation. The residue is chromatographed on silica gel (mobile solvent: dichloromethane/methanol=4/1).

Yield: 43.48 g (68% of theory) of a colorless, viscous liquid

Elementary analysis: Cld: C 33.81, H 3.47, N 2.19, S 5.02, F 50.51 Fnd: C 33.71 H 3.39, N 2.15, S 4.93, F 50.31 b) N-Decyl-N-(perfluorooctylsulfonyl)-aminoacetic acid-t-butyl ester 24.26 g (37.94 mmol) of the title compound of Example 36a and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 24.87 g (87% of theory) of a waxy, colorless solid
Elementary analysis: Cld: C 38.25, H 4.28, N 1.86, S 4.26, F 42.86 Fnd: C 38.09 H 4.41, N 1.74, S 4.10, F 42.67 c) N-Decyl-N-(perfluorooctylsulfonyl)-aminoacetic acid 20 g (26.54 mmol) of the title compound of Example 36b is dissolved in 200 ml of trifluoroacetic acid and stirred overnight at room temperature. It is evaporated to dryness in a vacuum. The residue is recrystallized from methanol/ether.

Yield: 17.22 g (93% of theory) of a colorless, crystalline solid

Elementary analysis: Cld: C 34.44, H 3.47, N 2.01, S 4.60, F 46.31 Fnd: C 34.28 H 3.30, N 1.95, S 4.65, F 46.28 d) Gadolinium complex of 10-[2-hydroxy-4-aza-5-oxo-7-aza-7-(perfluorooctylsulfonyl)-heptadecyl]-1,4,7-tris(carboxymethyl)-1,4,7,10-tetraazacyclododecane 11.92 g (17.09 mmol) of the title compound of Example 36c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/50 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 16.76 g (71% of theory) of a colorless, vitreous solid

Water content: 6.5%

Elementary analysis: Cld: C 35.46, H 4.18, N 6.71, S 2.56, F 25.77 Gd 12.55 Fnd: c 35.28 H 4.33, N 6.80 S 2.61, F 25.65 Gd 12.41

EXAMPLE 37 a) N-Hexylperfluorooctanesulfonamide 50.21 g (100.0 mmol) of perfluoroctanesulfonyl fluoride is added in drops to a mixture of 10.62 g (105.0 mmol) of triethylamine and 10.12 g (100.0 mmol) of benzylamine at 80° C. while being stirred vigorously. It is stirred for 2 days at 80° C., the reaction mixture is mixed with 300 ml of water and extracted three times with ethyl acetate. The combined organic extracts are dried on sodium sulfate, filtered and concentrated by evaporation. The residue is chromatographed on silica gel (mobile solvent: dichloromethane/methanol=4/1).

Yield: 45.50 g (78% of theory) of a colorless liquid
Elementary analysis: Cld: C 28.83, H 2.42, N 2.40, S 5.50, F 55.37 Fnd: C 28.29 H 2.39, N 2.44, S 5.55, F 55.50 b) N-Hexyl-N-(perfluorooctylsulfonyl)-aminoacetic acid-t-butyl ester 22.13 g (37.94 mmol) of the title compound of Example 37a and 15.73 g (113.8 mmol) of potassium carbonate are suspended in 200 ml of acetone, and 14.80 g (75.87 mmol) of bromoacetic acid-tert-butyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 23.02 g (87% of theory) of a waxy, colorless solid
Elementary analysis: Cld: C 34.44, H 3.47, N 2.01, S 4.60, F 46.31 Fnd: C 34.31 H 3.61, N 1.97, S 4.65, F 46.25 c) N-Hexyl-N-(perfluorooctylsulfonyl)-aminoacetic acid 20 g (28.43 mmol) of the title compound of Example 37b is dissolved in 200 ml of trifluoroacetic acid, and it is stirred overnight at room temperature. It is evaporated to dryness in a vacuum. The residue is recrystallized from methanol/ether.

Yield: 16.74 g (91% of theory) of a colorless, crystalline solid

Elementary analysis: Cld: C 29.96, H 2.51, N 2.18, S 5.00, F 50.36 Fnd: C 29.87 H 2.70, N 2.05, S 4.84, F 50.17 d) Gadolinium complex of 10-[2-hydroxy-4-aza-5-oxo-7-aza-7-(perfluorooctylsulfonyl)-tridecyl]-1,4,7-tris(carboxymethyl)-1,4,7,10-tetraazacyclododecane 10.96 g (17.09 mmol) of the title compound of Example 37c and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/S0 ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 16.46 g (75% of theory) of a colorless, vitreous solid

Water content: 6.8%

Elementary analysis: Cld: C 33.11, H 3.70, N 7.02, S 2.68, F 26.98 Gd 13.14 Fnd: C 33.01 H 3.84, N 6.95, S 2.57, F 26.85 Gd 13.03

EXAMPLE 38 a) 11-[N-Ethyl-N-(perfluorooctylsulfonyl)-amino]-hexanoic acid benzyl ester 20 g (37.94 mmol) of N-ethyl-N-perfluorooctylsulfonylamide and 15.73 g (113.8 mmol) of potassium carbonate are suspended in 200 ml of acetone, and 21.64 g (75.87 mmol) of 6-bromohexanoic acid benzyl ester is added in drops at 60° C. It is stirred for 3 hours at 60° C. Salts are filtered out, and the filtrate is evaporated to dryness in a vacuum. The residue is chromatographed on silica gel (mobile solvent: hexane/dichloromethane/acetone=10/10/1). After the product-containing fractions are concentrated by evaporation, the residue is recrystallized from methanol/ether.

Yield: 25.26 g (91% of theory) of a colorless, crystalline powder

Elementary analysis: Cld: C 37.77, H 3.03, N 1.91, S 4.38, F 44.15 Fnd: C 37.61 H 3.18, N 1.84, S 4.27, F 44.01 b) 11-[N-Ethyl-N-(perfluorooctylsulfonyl)-amino]-hexanoic acid 20 g (27.34 mmol) of the title compound of Example 38b is dissolved in 300 ml of isopropanol/200 ml of dichloromethane, and 3 g of palladium catalyst (10% Pd/C) is added. It is hydrogenated overnight at room temperature. Catalyst is filtered out, and the filtrate is evaporated to dryness in a vacuum. The residue is recrystallized from ether/hexane.

Yield: 16.13 g (92% of theory) of a colorless, crystalline solid

Elementary analysis: Cld: C 29.96, H 2.51, N 2.18, S 5.00, F 50.36 Fnd: C 29.81 H 2.70, N 2.09, S 4.93, F 50.14 d) Gadolinium complex of 10-[2-hydroxy-4-aza-5-oxo-11-aza-11-(perfluorooctylsulfonyl)-tridecyl]-1,4,7-tris (carboxymethyl)-1,4,7,10-tetraazacyclododecane 10.96 g (17.09 mmol) of the title compound of Example 38b and 1.97 g (18.79 mmol) of N-hydroxysuccinimide are dissolved in a mixture of 50 ml of dimethylformamide/50 ml of chloroform. 3.88 g (18.79 mmol) of dicyclohexylcarbodiimide is added at 0° C., and it is stirred for 1 hour at 0° C., then for 3 hours at room temperature. It is cooled again to 0° C., and 5.19 g (51.27 mmol) of triethylamine/SO ml of 2-propanol is added. Then, 10.78 g (18.79 mmol) of the gadolinium complex of 10-(3-amino-2-hydroxy-propyl)-1,4,7-tris(carboxymethyl)-1,4,7,10-tetraazacyclododecane (WO 95/17451), dissolved in 50 ml of water, is added, and it is stirred for 3 hours at room temperature. It is evaporated to dryness, the residue is taken up in a mixture of 200 ml of methanol/100 ml of chloroform, and dicyclohexylurea is filtered out. The filtrate is evaporated to dryness and purified by RP-chromatography (RP-18 mobile solvent: gradient consisting of water/n-propanol/acetonitrile).

Yield: 15.0 g (69% of theory) of a colorless, vitreous solid
Water content: 5.9%
Elementary analysis: Cld: C 33.11, H 3.70, N 7.02, S 2.68, F 26.98 Gd 13.14 Fnd: C 33.01 H 3.83, N 6.91, S 2.49, F 26.83 Gd 13.05

EXAMPLE 39

A 100 mmol/l solution in water, which contained an addition of 100 mg of I/ml of Isovist® as an x-ray-opaque marker, was produced from the compound of Example 1c). This solution is transparent and has a gel-like solid consistency, but can be administered with ease by hand or with an infusion pump with a 20 cm long, 0.58 mm $\phi_i$ tube at a rate of 160 µl/min.

EXAMPLE 40

Solubility of the Gadolinium Complex of Example 1c) in Various Solvents and with Various Additives and Forms of Administration A 100 mmol/L of solution in water is produced from the compound of Example 1c). This solution is transparent and has a gel-like solid consistency, but can be administered with ease by hand or with an infusion pump with a 20 cm long, 0.58 mm $\phi_i$ tube at a rate of 160 µL/min. A free-flowing solution is produced below about 10–20 mmol/L.

The addition of 10 mmol/L (final concentration) of HCl or NaOH or high salt concentrations (3 mol/L of NaCl) has no influence on the consistency of the preparation.

The addition of 8 mol/L (final concentration) of urea produces a free-flowing solution that also has very high substance concentrations (400 mmol/L).

The addition of detergents to the aqueous formulation of the compound of Example 1c) has a very different effect. Tween® 80 (polyoxyethylene-sorbitan-oleate, nonionic detergent, HLB 15, 4.6% final concentration) does not cause any change in consistency, while Triton® X-100 (octylphenol-polyethylene glycol ether, nonionic detergent, HLB 13.5, 1.7%) results in liquefaction of the gel-like consistency.

In bovine plasma, the substance is just as soluble as in pure water and produces a solution with comparable consistency.

The compound of Example 1c) is virtually insoluble in pure propylene glycol or DMSO. In 66% propylene glycol/water or 66% DMSO/water, however, the substance is also readily soluble at higher concentrations (250 mmol/L or 150 mmol/L) and produces a free-flowing solution.

In 96% ethanol, the solubility of the substance is greater than 500 mmol/L. A free-flowing solution is produced.

EXAMPLE 41

Solubility of the Dysprosium Complex of Example 30f) in Various Solvents and with Various Additives and Forms of Administration.

A 100 mmol/L of solution in water is produced from the compound of Example 30f). This solution is transparent and has a gel-like solid consistency, but can be administered with ease by hand or with an infusion pump with a 20 cm long, 0.58 mm $\phi_i$ tube at a rate of 160 µL/min. A free-flowing solution is produced below about 10–20 mmol/L.

The addition of 10 mmol/L (final concentration) of HCl or NaOH or high salt concentrations (3 mol/L of NaCl) has no influence on the consistency of the preparation.

The addition of 8 mol/L (final concentration) of urea produces a free-flowing solution that also has very high substance concentrations (400 mmol/L).

The addition of detergents to the aqueous formulation of the compound of Example 30f) has a very different effect. Tween® 80 (polyoxyethylene-sorbitan-oleate, nonionic detergent, HLE 15, 4.6% final concentration) does not entail any change in consistency, while Triton(R) X-100 (octylphenol-polyethylene glycol ether, nonionic detergent, HLB 13.5, 1.7%) results in a liquefaction of the gel-like consistency.

In bovine plasma, the substance is just as soluble as in pure water and produces a solution with comparable consistency.

The compound of Example 30f) is virtually insoluble in pure propylene glycol or DMSO. In 66% propylene glycol/water or 66% DMSO/water, however, the substance is also readily soluble at higher concentrations (250 mmol/L or 150 mmol/L) and produces a free-flowing solution.

In 96% ethanol, the solubility of the substance is greater than 500 mmol/L. A free-flowing solution is produced.

EXAMPLE 42

Incorporation of Cytostatic Agents into the Solution of the Compound of Example 1c)

The materials that are used for embolization of tumors are also suitable in principle for local administration of cytostatic agents, which are present in this way in the tumor at very high, systemic, but low and thus well-tolerated concentrations. In addition, the embolism ensures delayed release over several days, which further increases the effectiveness of the cytostatic agent.

5-Fluorouracil, doxorubicin, mitomycin C or cisplatin, in addition to some other cytostatic agents, are usually used for treating HCC. If an aqueous solution of the cytostatic agent is used for the production of the solution of the compound of Example 1c), the latter is homogeneously embedded in the formulation. The concentration used of the cytostatic agent depends on the amount of solution to be administered, so that the maximum dose that can be tolerated in mg/kg of body weight or in mg/m² of body surface is not exceeded. For the individual cytostatic agents, the following solutions for the production of a formulation of compound 1c) can be used:

| | |
|---|---|
| Cisplatin | 1–20 mg/ml |
| mitomycin C | 0.5–10 mg/ml |
| doxorubicin | 1–20 mg/ml |
| 5-fluorouracil | 10–200 mg/ml |

EXAMPLE 43

Demonstration of an embolization in an animal model. The renal vessels of rats were embolized as vessels that can be readily visualized.

A catheter (20 cm long, 0.58 mm $\phi_i$ in the A. mesenterica) was bound to the animal and advanced into the A. renalis of the left kidney. The solution of the compound of Example 1c) (here, 50 mmol/l with 150 mg of I/ml of Isovist®) was administered at 160 µl/min. Total volume 250 µl. Then, the catheter in the A. mesenterica was retracted so as not to adversely affect the blood supply of the kidneys later on. In the following x-ray pictures, the vessels of the left kidney were greatly delimited relative to the kidney parenchyma. Up to 45 minutes after the compound of Example 1c) is administered, the signal intensity of the vessels in the kidney can be considerably reduced. This can be attributed to an outward diffusing of x-ray contrast medium Isovist® and its renal elimination. To monitor the renal blood circulation, 400 µl of x-ray contrast medium Ultravist® 300 that passes through the kidneys was added to 300 mg of 1/ml i.v. in the caudal vein 1 hour after the local administration of the compound of Example 1c). Only the non-embolized right kidney with a renal duct showed a significant enhancement, an indication of good blood supply and full function of this kidney. The embolized left kidney and its renal duct, however, did not show any enhancement, which indicates the continued presence of the embolism.

The effectiveness of the process is conveyed by FIGS. 1 and 2:

Figure 1:
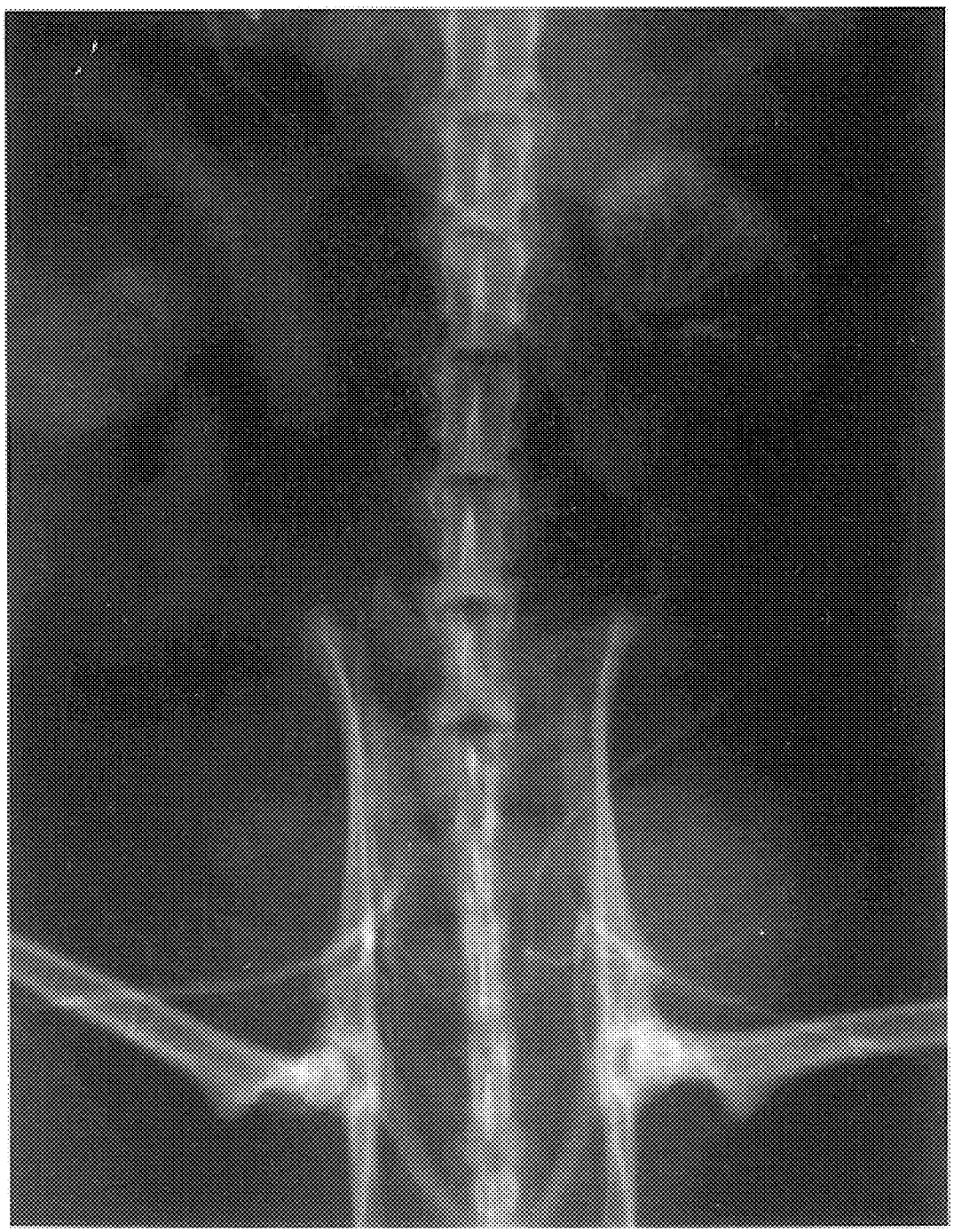
FIG. 1 is an image of embolization of the kidney of a rat directly after intraarterial, local administration of 2500 ml of a solution of the compound of Example 1c (50 mmol/L+150 mg of I/ml of Isovist® in the catheterized renal artery (left kidney, right in the figure).
Figure 2:
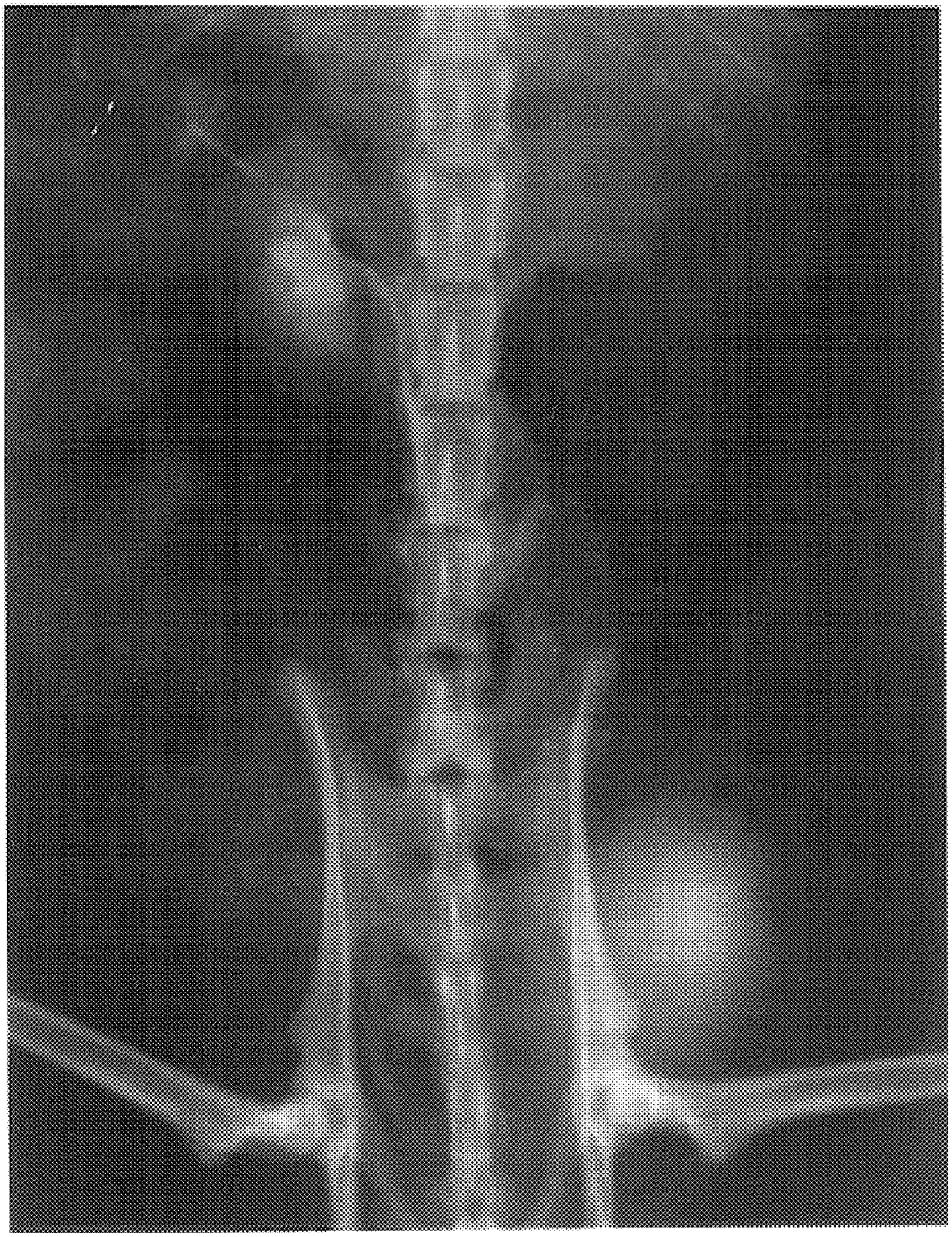
FIG. 2 is an X-ray image of the kidney of a rat as a control test.

5′ p.a. Ultravist®, 400 µl i.v.

1 hour after local administration of the compound of Example 1c), Ultravist® was given via the caudal vein. The right kidney excretes the x-ray contrast medium, the treated (embolized) left kidney is dark. The bladder (lower right) is also light.

EXAMPLE 44

Demonstration of Embolization in Another Animal Model. As Vessels that can be Readily Visualized, the Hepatic Vessels in Rabbits were Embolized.

A catheter (60 cm long, 1.5 mm $\phi_a$) was advanced into the narcotized animal via the A. femoralis to the hepatic artery through the aorta. The solution of the gadolinium complex of Example 1c) (50 mmol/L with 150 mg of I/ml of Isovist®) was aministered at 160 µL/min. Total volume 800 µL. Then, the catheter in the aorta was withdrawn so as not to impair the arterial blood supply of the liver later on. In the following x-rays, the vessels of the liver were clearly delimited from the liver parenchyma. Within 60 minutes after the compound of Example 1c) is administered, the signal intensity of the vessels in the liver only slowly decreased, which indicates continuing embolization through the substance. The reduction in signal intensity can be attributed in part to an outward diffusing of the x-ray contrast medium Isovist®.

EXAMPLE 45

Treatment of a Liver Carcinoma in Rabbits

In five male chinchilla rabbits, a tumor was placed by injection of VX-2 tumor cells in the left lobe of the liver. A catheter (60 cm long, 1 mm $\phi_a$) was advanced into the anesthetized animal via the Arteria femoralis to the vicinity of the tumor. Then, a solution of the title compound of Example 1c [75 mmol/l with 50 mg of cisplatin (=Carboplatin®) was administered. Total volume 8 ml.

Then, the catheter was removed. After 7 days, the animals were tested using MRI. It was shown that the tumor had decreased in size (average growth factor 0.8±0.20). In the control animals (3 animals), however, growth rates of 3.7±1.5 were observed.

What is claimed is:

1. A perfluoroalkyl-containing compound of formula I

$$R^F\text{—}L\text{—}A \qquad\qquad I$$

in which $R^F$ is a perfluorinated, straight-chain or branched carbon chain with formula —$C_nF_{2n}X$, in which X represents a terminal fluorine, chlorine, bromine, iodine or hydrogen atom, and n stands for numbers 4–30, L means a direct bond, a methylene group, an —NHCO group, a group

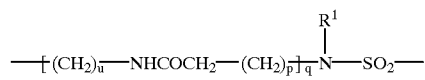

$$-\!\!\left[(CH_2)_u\right]\!\!-\!\!NHCOCH_2\!-\!(CH_2)_p\!\!\left.\right]_q\!\!-\!\!\overset{R^1}{\underset{|}{N}}\!\!-\!\!SO_2\!-$$

wherein p is 0 to 10, q and u, independently of one another, are 0 or 1 and $R^1$ is a hydrogen atom, a methyl group, a —$CH_2$—OH group, a —$CH_2CO_2H$ group or a $C_2$-$C_5$ chain, which optionally is interrupted by 1 to 3 oxygen atoms, 1 to 2 —CO—groups or an optionally substituted aryl group and/or is substituted with 1 to 4 hydroxyl groups, 1 to 2 $C_1$-$C_4$ alkoxy groups, 1 to 2 carboxy groups, or a group —$SO_3H$, or L is a straight-chain, branched, saturated or unsaturated $C_2$-$C_{30}$ carbon chain, which optionally contains 1 to 10 oxygen atoms, 1 to 3 —$NR^1$ groups, 1 to 2 sulfur atoms, a piperazine, a —$CONR^1$ group, a —$NR^1CO$-group, an —$SO_2$— group, an —$NR^1$—$CO_2$— group, 1 to 2 —CO— groups, a group

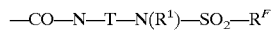

$$-\!CO\!-\!N\!-\!T\!-\!N(R^1)\!-\!SO_2\!-\!R^F$$

or 1 to 2 optionally substituted aryls and/or is interrupted by these groups and/or is optionally substituted with 1 to 3

—OR$^1$ groups, 1 to 2 oxo groups, 1 to 2 —NH—COR$^1$ groups, 1 to 2 —CONHR$^1$— groups, 1 to 2 —(CH$_2$)$_p$—CO$_2$H— groups, or 1 to 2 groups of —(CH$_2$)$_p$—(O)$_q$—CH$_2$CH$_2$—R$^F$, whereby R$^1$, R$^F$ and p and q have the above-identified meanings, and T means a C$_2$–C$_{10}$ chain, which optionally is interrupted by 1 to 2 oxygen atoms or 1 to 2 —NHCO— groups, A stands for a metal complex or a salt thereof with an organic an/or inorganic base or amino acid or amino acid amide, of formula II

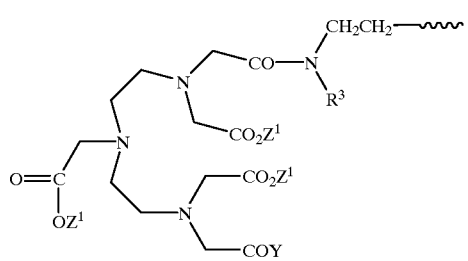

(II)

R$^3$ independently has the meaning of R$^1$ or means —(CH$_{2m}$—L—R$^F$, whereby m is 0, 1 or 2 L and R$^F$ independently have the above-mentioned meaning, Z$^1$ means a metal ion equivalent of atomic numbers 12, 20–30, 39, 42, 44 or 57–83, Y independently means —OZ$^1$,

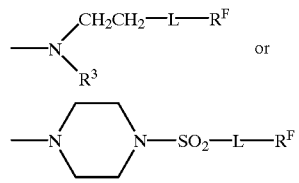

or

A stands for a complex of formula III

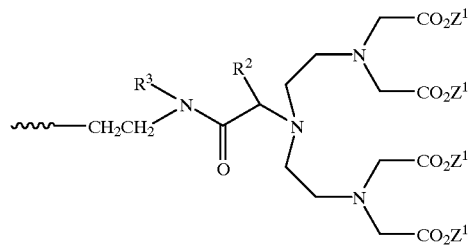

(III)

in which R$^3$ and Z$^1$ have the above-mentioned meanings and R$^2$ has the meaning of R$^1$, or A stands for a complex of formula IV

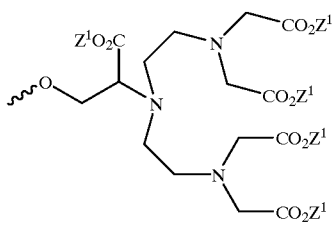

(IV)

in which Z$^1$ has the above-mentioned meaning, or

A stands for a complex of formula V

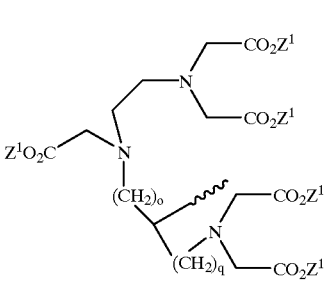

(V)

in which Z$^1$ has the above-mentioned meaning, and o and q stand for numbers 0 or 1 and the sum o+q=1 results, or A stands for a complex of formula VI

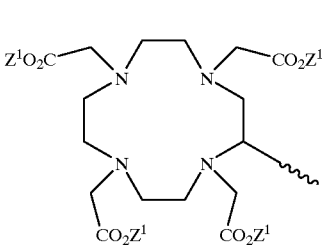

(VI)

in which Z$^1$ has the above-mentioned meaning or

A stands for a complex of formula VII

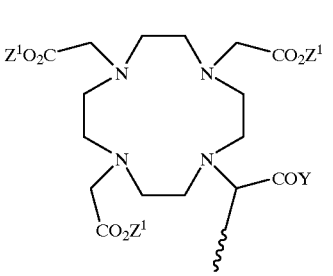

(VII)

in which Z$^1$ and Y have the above-mentioned meanings or

A stands for a complex of formula VIII

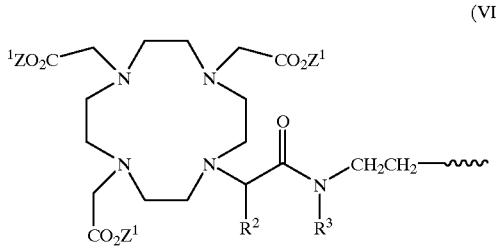

(VIII)

in which $R^3$ and $Z^1$ have the above-mentioned meanings, and $R^2$ has the above-mentioned meaning of $R^1$, or A stands for a complex of formula IX

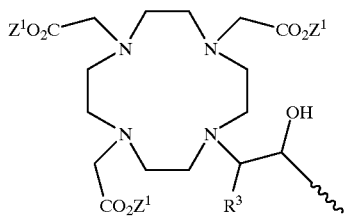

(IX)

in which $R^3$ and $Z^1$ have the above-mentioned meanings, or

A stands for a complexing agent or complex of formula X

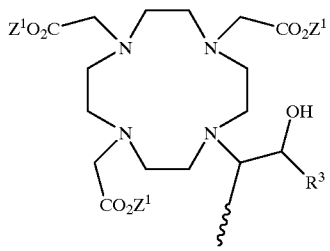

(X)

in which $R^3$ and $Z^1$ have the above-mentioned meanings, or

A stands for a complexing agent or complex of formula XI

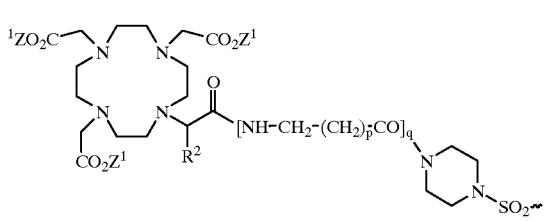

(XI)

in which $Z^1$, p and q have the above-mentioned meanings and $R^2$ has the meaning of $R^1$, or A stands for a complex of formula XII

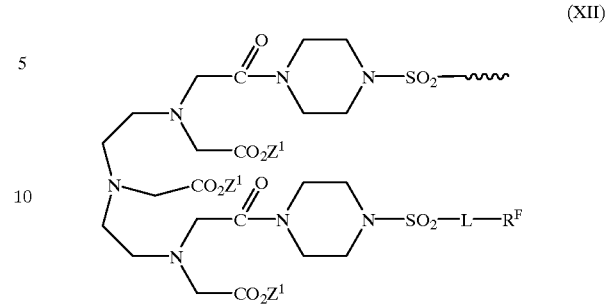

(XII)

in which L, $R^F$ and $Z^1$ have the above-mentioned meanings, or

A stands for a complex of formula XIII

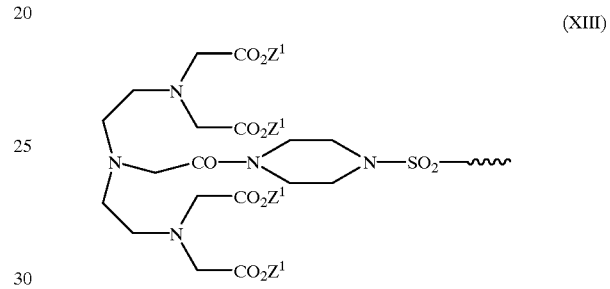

(XIII)

in which $Z^1$ has the above-mentioned meaning, with the proviso that $R^F$ is not $C(CF_3)_3$, optionally with additives used in galenicals, for tumor therapy, for heptocellular carcinoma (HCC) or for interventional radiology.

2. A compound according to claim 1, wherein n in formula $-C_nF_{2n}X$ stands for numbers 4–15.

3. A compound according to claim 1, wherein X in formula $-C_nF_{2n}X$ means a fluorine atom.

4. A compound according to claim 1 containing gadolinium complex of 10-[2-hydroxy-4-aza-5-oxo-7-aza-7-(perfluorooctylsulfonyl)-nonyl]-1,4,7-tris(carboxymethyl)-1,4,7,10-tetraazacyclododecane.

5. A compound of formula I according to claim 1 and at least one chemotherapy agent.

6. A compound according to claim 5 wherein the chemotherapy agent is 5-fluorouracil, cisplatin, doxorubicin and/or mitomycin C.

7. A compound of formula I according to claim 1 and at least one contrast medium for NMR diagnosis or diagnostic radiology.

8. A compound according to claim 5, and at least one contrast medium for NMR diagnosis or diagnostic radiology.

9. A compound according to claim 1, wherein $R^F$ is a perfluorinated, straight-chain carbon chain.

10. A method of tumor therapy, comprising administering a compound according to claim 1.

11. A method according to claim 10, wherein the compound is administered in combination with at least one chemotherapy agent.

12. A method according to claim 11, wherein 5-fluorouracil, cisplatin, doxorubicin and/or mitomycin C is/are used as a chemotherapy agent.

13. A method for interventional radiology, comprising administering a pharmaceutical agent in combination with at least one contrast medium for NMR diagnosis or diagnostic radiology, wherein the pharmaceutical agent consists essentially of a compound of formula I

   I in which

- $R^F$ is a perfluorinated, straight-chain or branched carbon chain with formula $-C_nF_{2n}X$, in which
  - X represents a terminal fluorine, chlorine, bromine, iodine or hydrogen atom, and n stands for numbers 4–30,
- L means a direct bond, a methylene group, an —NHCO group, a group

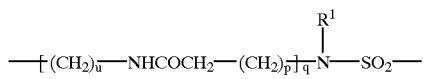

wherein p is 0 to 10, q and u, independently of one another, are 0 or 1 and

- $R^1$ is a hydrogen atom, a methyl group, a $-CH_2-OH$ group, a $-CH_2CO_2H$ group or a $C_2-C_{15}$ chain, which optionally is interrupted by 1 to 3 oxygen atoms, 1 to 2 —CO— groups or an optionally substituted aryl group and/or is substituted with 1 to 4 hydroxyl groups, 1 to 2 $C_1-C_4$ alkoxy groups, 1 to 2 carboxy groups, or a group $-SO_3H$, or L is a straight-chain, branched, saturated or unsaturated $C_2-C_{30}$ carbon chain, which optionally contains 1 to 10 oxygen atoms, 1 to 3 $-NR^1$ groups, 1 to 2 sulfur atoms, a piperazine; a $-CONR^1$ group, a $-NR^1CO$-group, an $-SO_2-$ group, an $-NR^1-CO_2$-group, 1 to 2 —CO— groups, a group

or 1 to 2 optionally substituted aryls and/or is interrupted by these groups and/or is optionally substituted with 1 to 3 $-OR^1$ groups, 1 to 2 oxo groups, 1 to 2 $-NH-COR^1-$ groups, 1 to 2 $-CONHR^1-$ groups, 1 to 2 $-(CH_p-CO_2H-$ groups, or 1 to 2 groups of $-(CH_2)_p-(O)_q-CH_2CH_2-R^F$, whereby

- $R^1$, $R^F$ and p and q have the above-identified meanings, and
- T means a $C_2-C_{10}$ chain, which optionally is interrupted by 1 to 2 oxygen atoms or 1 to 2 —NHCO— groups,
- A stands for a metal complex or a salt thereof with an organic an/or inorganic base or amino acid or amino acid amide of formula II

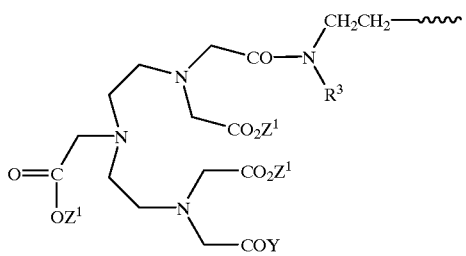

$R^3$ independently has the meaning of $R^1$ or means $-(CH_2)_m-L-R^F$, whereby m is 0, 1 or 2 L and $R^F$ independently have the above-mentioned meaning, $Z^1$ means a metal ion equivalent of atomic numbers 12, 20–30, 39, 42, 44 or 57–83, Y independently means $-OZ^1$,

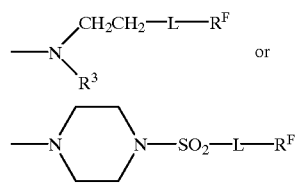

or

A stands for a complex of formula III

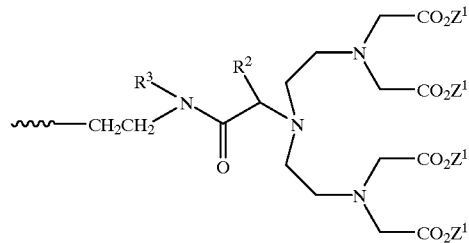

in which $R^3$ and $Z^3$ have the above-mentioned meanings and $R^2$ has the meaning of $R^1$, or A stands for a complex of formula IV

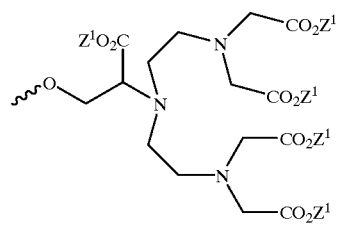

in which $Z^1$ has the above-mentioned meaning, or

A stands for a complex of formula V

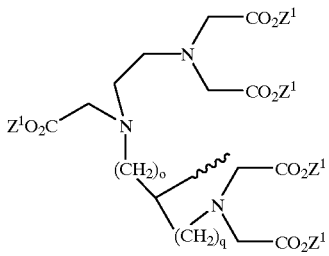
(V)

in which $Z^1$ has the above-mentioned meaning, and o and q stand for numbers 0 or 1 and the sum o+q=1 results, or A stands for a complex of formula VI

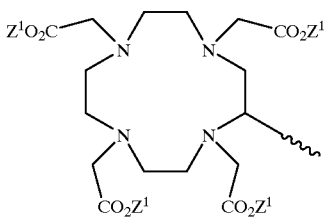
(VI)

in which $Z^1$ has the above-mentioned meaning or

A stands for a complex of formula VII

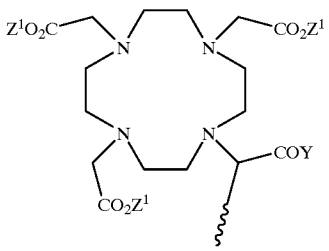
(VII)

in which $Z^1$ and Y have the above-mentioned meanings or

A stands for a complex of formula VIII

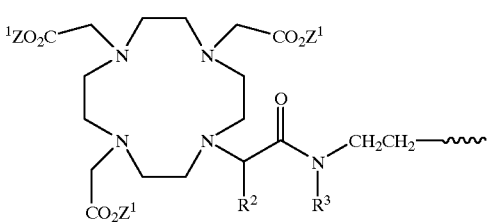
(VIII)

in which $R^3$ and $Z^1$ have the above-mentioned meanings, and $R^2$ has the above-mentioned meaning of $R^1$, or A stands for a complex of formula IX

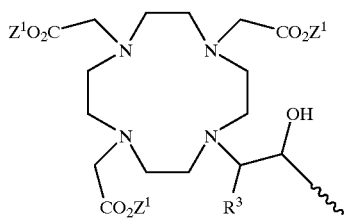
(IX)

in which $R^3$ and $Z^1$ have the above-mentioned meanings, or

A stands for a complexing agent or complex of formula X

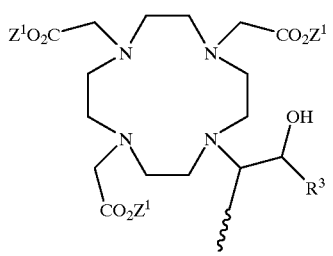
(X)

in which $R^3$ and $Z^1$ have the above-mentioned meanings, or

A stands for a completing agent or complex of formula XI

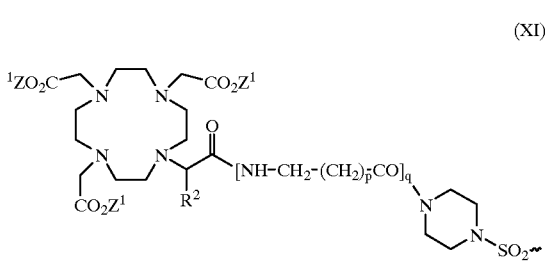
(XI)

in which $Z^1$, p and have the above-mentioned meanings and $R^2$ has the meaning of or A stands for a complex of formula XII

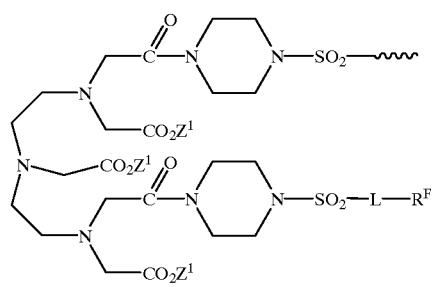
(XII)

in which L, $R^F$ and $Z^1$ have the above-mentioned meanings, or

A stands for a complex of formula XIII

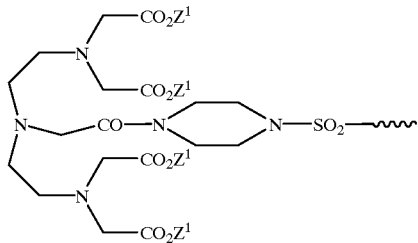

(XIII)

in which $Z^1$ has the above-mentioned meaning.

14. A method according to claim 13, wherein the pharmaceutical agent is administered in combination with at least one chemotherapy agent.

15. A method according to claim 13, wherein in the compound $R^F$ is not $C(CF_3)_3$.

16. A method according to claim 13, wherein $R^F$ is a perfluorinated, straight-chain carbon chain.

17. A method of tumor therapy, comprising administering a pharmaceutical agent consisting essentially of a compound of formula I'

I' in which
  $R^F$ is a perfluorinated, straight-chain or branched carbon chain with formula $-C_nF_{2n}X$, in which
    X represents a terminal fluorine, chlorine, bromine, iodine or hydrogen atom, and n stands for numbers 4–30,
  L means a direct bond, a methylene group, an —NHCO group, a group

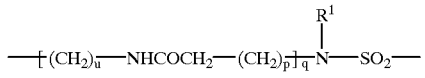

wherein p is 0 to 10, q and u, independently of one another, are 0 or 1 and
  $R^1$ is a hydrogen atom, a methyl group, a —CH$_2$—OH group, a —CH$_2$CO$_2$H group or a $C_2$–$C_{15}$ chain, which optionally is interrupted by 1 to 3 oxygen atoms, 1 to 2 —CO— groups or an optionally substituted aryl group and/or is substituted with 1 to 4 hydroxyl groups, 1 to 2 $C_1$–$C_4$ alkoxy groups, 1 to 2 carboxy groups, or a group —SO$_3$H, or L is a straight-chain, branched, saturated or unsaturated $C_2$–$C_{30}$ carbon chain, which optionally contains 1 to 10 oxygen atoms, 1 to 3 —NR$^1$ groups, 1 to 2 sulfur atoms, a piperazine, a —CONR$^1$ group, a —NR$^1$CO-group, an —SO$_2$— group, an —NR$^1$—CO$_2$— group, 1 to 2 —CO— groups, a group

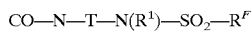

or 1 to 2 optionally substituted aryls and/or is interrupted by these groups and/or is optionally substituted with 1 to 3 —OR$^1$ groups, 1 to 2 oxo groups, 1 to 2 —NH—COR$^1$—groups, 1 to 2 —CONHR$^1$— groups, 1 to 2 —(CH)$_p$—CO$_2$H— groups, or 1 to 2 groups of —(CH$_2$)$_p$—(O)$_q$—CH$_2$CH$_2$—R$^F$, whereby
  $R^1$, $R^F$ and p and q have the above-identified meanings, and
  T means a $C_2$–$C_{10}$ chain, which optionally is interrupted by 1 to 2 oxygen atoms or 1 to 2 —NHCO— groups,
  A stands for a metal complex or a salt thereof with an organic an/or inorganic base or amino acid or amino acid amide of formula II

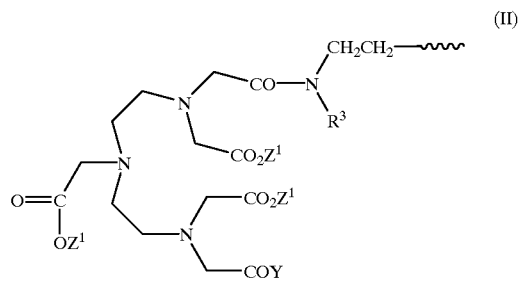

(II)

$R^3$ independently has the meaning of $R^1$ or means —(CH$_2$)$_m$—L—$R_F$, whereby m is 0, 1 or 2 L and $R^F$ independently have the above-mentioned meaning,
  $Z^1$ means a metal ion equivalent of atomic numbers 12, 20–30, 39, 42, 44 or 57–83,
  Y independently means —OZ$^1$,

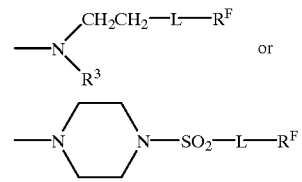

or
A stands for a complex of formula III

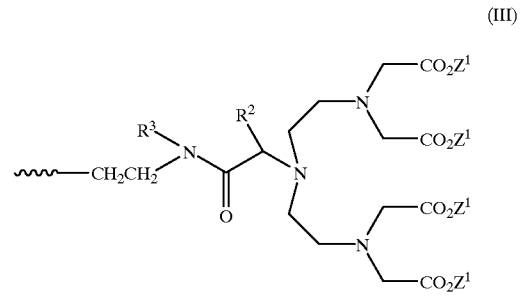

(III)

in which $R^3$ and $Z^1$ have the above-mentioned meanings and $R^2$ has the meaning of $R^1$, or A stands for a complex of formula IV

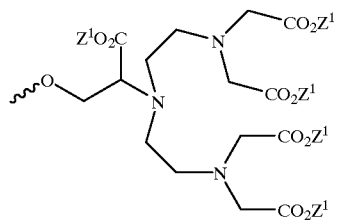
(IV)

in which $Z^1$ has the above-mentioned meaning, or

A stands for a complex of formula V

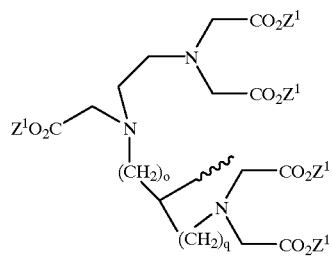
(V)

in which $Z^1$ has the above-mentioned meaning, and o and q stand for numbers 0 or 1 and the sum o+q=1 results, or A stands for a complex of formula VI

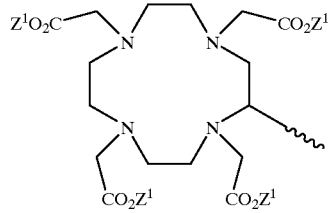
(VI)

in which $Z^1$ has the above-mentioned meaning or

A stands for a complex of formula VII

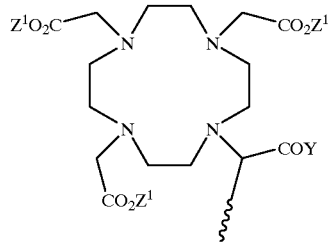
(VII)

in which $Z^1$ and Y have the above-mentioned meanings or

A stands for a complex of formula VIII

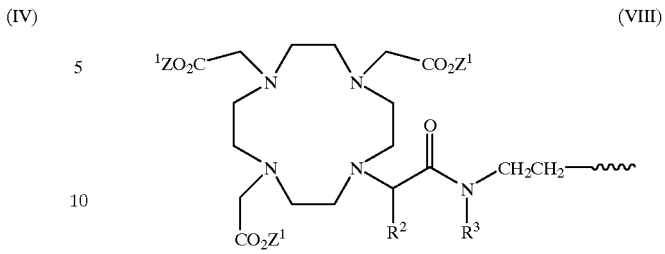
(VIII)

in which $R^3$ and $Z^1$ have the above-mentioned meanings, and $R^2$ has the above-mentioned meaning of $R^1$, or A stands for a complex of formula IX

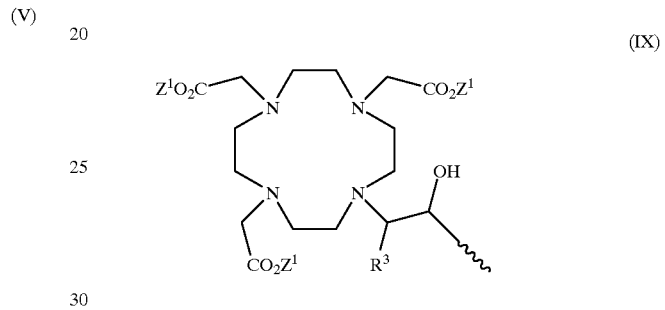
(IX)

in which $R^3$ and $Z^1$ have the above-mentioned meanings, or

A stands for a complexing agent or complex of formula X

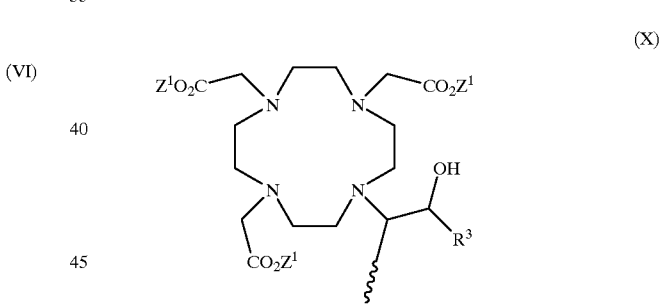
(X)

in which $R^3$ and $Z^1$ have the above-mentioned meanings, or

A stands for a complexing agent or complex of formula XI

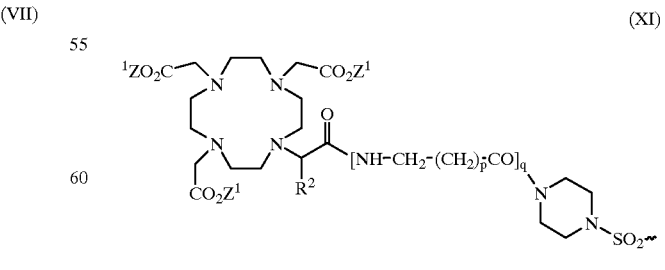
(XI)

in which $Z^1$, p and q have the above-mentioned meanings and $R^2$ has the meaning of $R^1$, or A stands for a complex of formula XII

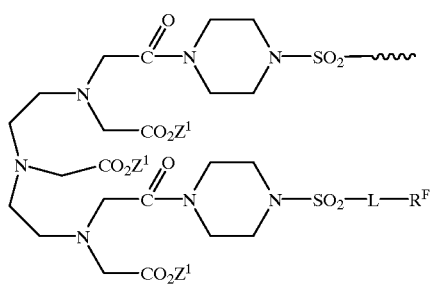

(XII)

in which L, $R^F$ and $Z^1$ have the above-mentioned meanings, or

A stands for a complex of formula XIII

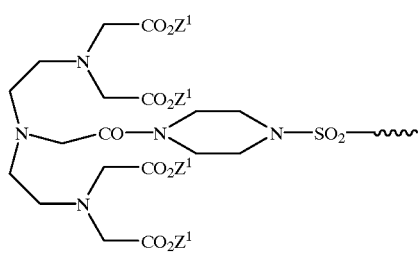

(XIII)

in which $Z^1$ has the above-mentioned meaning.

18. A method according to claim 15, wherein the pharmaceutical agent is administered in combination with at least one chemotherapy agent.

19. A method for the treatment of heptacellular carcinoma, comprising administering a pharmaceutical agent according to claim 1.

20. A method for interventional radiology, comprising administering a pharmaceutical agent according to claim 1.

21. A method for tumor therapy, comprising administering a pharmaceutical agent in combination with at least one contrast medium for NMR diagnosis or diagnostic radiology, wherein the pharmaceutical agent consists essentially of a compound of formula I', $$R^F—L—A \qquad I'$$

in which $R^F$ is a perfluorinated, straight-chain or branched carbon chain with formula $—C_nF_{2n}X$, in which X represents a terminal fluorine, chlorine, bromine, iodine or hydrogen atom, and n stands for numbers 4–30, L means a direct bond, a methylene group, an —NHCO group, a group

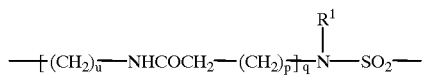

wherein p is 0 to 10, q and u, independently of one another, are 0 or 1 and $R^1$ is a hydrogen atom, a methyl group, a —CH$_2$—OH group, a —CH$_2$CO$_2$H group or a $C_2$–$C_{15}$ chain, which optionally is interrupted by 1 to 3 oxygen atoms, 1 to 2 —CO— groups or an optionally substituted aryl group and/or is substituted with 1 to 4 hydroxyl groups, 1 to 2 $C_1$–$C_4$ alkoxy groups, 1 to 2 carboxy groups, or a group —SO$_3$H, or L is a straight-chain, branched, saturated or unsaturated $C_2$–$C_{30}$ carbon chain, which optionally contains 1 to 10 oxygen atoms, 1 to 3 —NR$^1$ groups, 1 to 2 sulfur atoms, a piperazine, a —CONR$^1$ group, a —NR$^1$CO-group, an —SO$_2$— group, an —NR$^1$—CO$_2$-group, 1 to 2 —CO— groups, a group

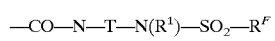

or 1 to 2 optionally substituted aryls and/or is interrupted by these groups and/or is optionally substituted with 1 to 3 —OR$^1$ groups, 1 to 2 oxo groups, 1 to 2 —NH—COR$^1$— groups, 1 to 2 —CONHR$^1$— groups, 1 to 2 —(CH$_2$)$_p$—CO$_2$H— groups, or 1 to 2 groups of —(CH$_2$)$_p$—(O)$_q$—CH$_2$CH$_2$—R$^F$, whereby $R^1$, $R^F$ and p and q have the above-identified meanings, and T means a $C_2$–$C_{10}$ chain, which optionally is interrupted by 1 to 2 oxygen atoms or 1 to 2 —NHCO— groups, A stands for a metal complex or a salt thereof with an organic an/or inorganic base or amino acid or amino acid amide of formula II

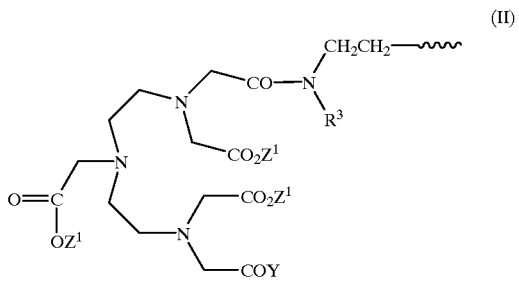

(II)

$R^3$ independently has the meaning of $R^1$ or means —(CH$_2$)$_m$—L—R$^F$, whereby m is 0, 1 or 2 L and $R^F$ independently have the above-mentioned meaning, $Z^1$ means a metal ion equivalent of atomic numbers 12, 20–30, 39, 42, 44 or 57–83, Y independently means —OZ$^1$,

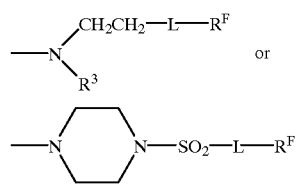

or

A stands for a complex of formula III

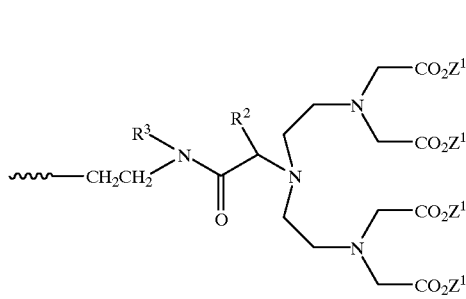
(III)

in which R³ and Z¹ have the above-mentioned meanings and R² has the meaning of R¹, or A stands for a complex of formula IV

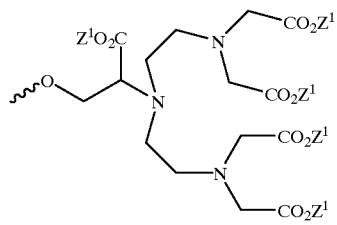
(IV)

in which Z¹ has the above-mentioned meaning, or

A stands for a complex of formula V

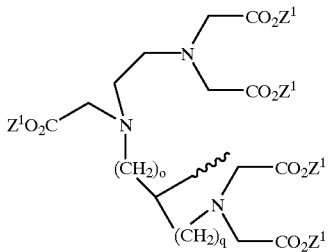
(V)

in which Z¹ has the above-mentioned meaning, and o and q stand for numbers 0 or 1 and the sum o+q=1 results, or A stands for a complex of formula VI

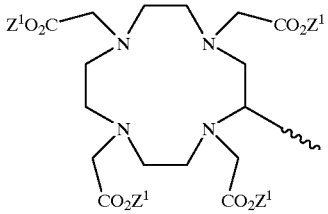
(VI)

in which Z¹ has the above-mentioned meaning or

A stands for a complex of formula VII

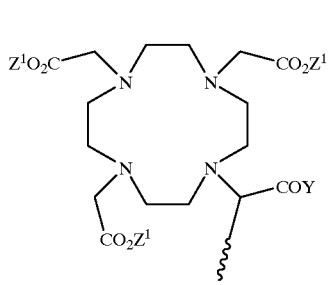
(VII)

in which Z¹ and Y have the above-mentioned meanings or

A stands for a complex of formula VIII

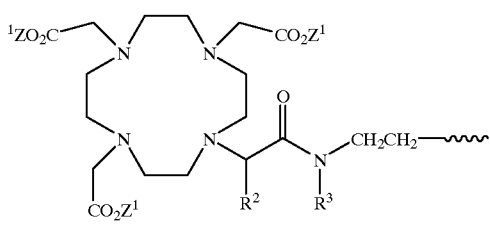
(VIII)

in which R³ and Z¹ have the above-mentioned meanings, and R² has the above-mentioned meaning of R¹, or A stands for a complex of formula IX

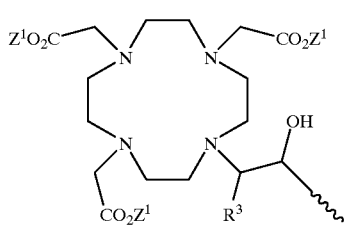
(IX)

in which R³ and Z¹ have the above-mentioned meanings, or

A stands for a complexing agent or complex of formula X

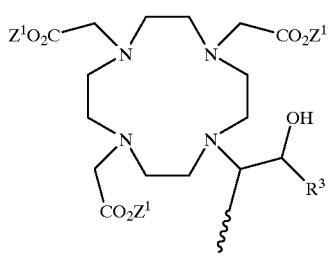
(X)

in which R³ and Z¹ have the above-mentioned meanings, or

A stands for a complexing agent or complex of formula XI

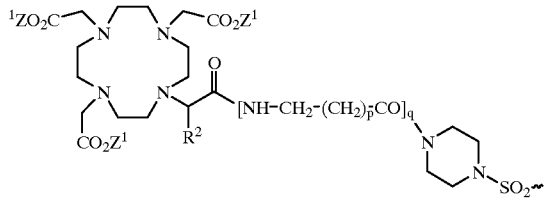

(XI)

in which $Z^1$, p and q have the above-mentioned meanings and $R^2$ has the meaning of $R^1$, or A stands for a complex of formula XII

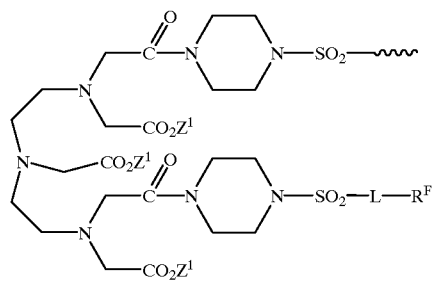

(XII)

in which L, $R^F$ and $Z^1$ have the above-mentioned meanings, or

A stands for a complex of formula XIII

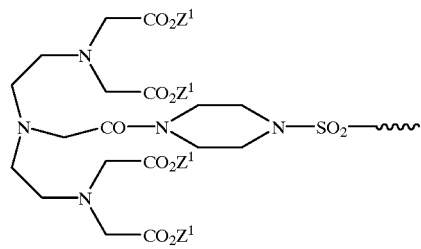

(XIII)

in which $Z^1$ has the above-mentioned meaning.

22. A method for treatment of heptacellular carcinoma (HCC) comprising administering a pharmaceutical agent in combination with at least one contrast medium for NMR diagnosis or diagnostic radiology, wherein the pharmaceutical agent consists essentially of a compound of formula I'

$$R^F-L-A \qquad I'$$

in which
- $R^F$ is a perfluorinated, straight-chain or branched carbon chain with formula $-C_nF_{2n}X$, in which
  - X represents a terminal fluorine, chlorine, bromine, iodine or hydrogen atom, and n stands for numbers 4–30,
- L means a direct bond, a methylene group, an —NHCO group, a group

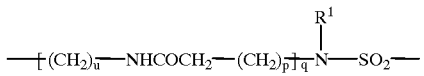

wherein p is 0 to 10, q and u, independently of one another, are 0 or 1 and
- $R^1$ is a hydrogen atom, a methyl group, a —CH$_2$—OH group, a —CH$_2$CO$_2$H group or a C$_2$–C$_{15}$ chain, which optionally is interrupted by 1 to 3 oxygen atoms, 1 to 2 —CO— groups or an optionally substituted aryl group and/or is substituted with 1 to 4 hydroxyl groups, 1 to 2 C$_1$–C$_4$ alkoxy groups, 1 to 2 carboxy groups, or a group —SO$_3$H,
- or L is a straight-chain, branched, saturated or unsaturated C$_2$–C$_{30}$ carbon chain, which optionally contains 1 to 10 oxygen atoms, 1 to 3 —NR$^1$ groups, 1 to 3 sulfur atoms, a piperazine, a —CONR$^1$ group, a —NR$^1$CO-group, an —SO$_2$— group, an —NR$^1$—CO$_2$-groups, 1 to 2 —CO— groups, a group $$-CO-N-T-N(R^1)-SO_2-R^F$$

or 1 to 2 optionally substituted aryls and/or is interrupted by these groups and/or is optionally substituted with 1 to 3 —OR$^1$ groups, 1 to 2 oxo groups, 1 to 2 —NH—COR$^1$— groups, 1 to 2 —CONHR$^1$— groups, 1 to 2 —(CH$_2$)$_p$—CO$_2$H— groups, or 1 to 2 groups of —(CH$_2$)$_p$—(O)$_q$—CH$_2$CH$_2$—R$^F$, whereby
- $R^1$, $R^F$ and p and q have the above-identified meanings, and
- T means a C$_2$–C$_{10}$ chain, which optionally is interrupted by 1 to 2 oxygen atoms or 1 to 2 —NHCO— groups, A stands for a metal complex or a salt thereof with an organic an/or inorganic base or amino acid or amino acid amide of formula II

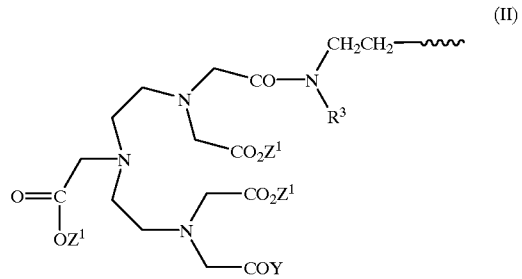

(II)

$R^3$ independently has the meaning of $R^1$ or means —(CH$_2$)$_m$—L—R$^F$, whereby m is 0, 1 or 2 L and $R^F$ independently have the above-mentioned meaning, $Z^1$ means a metal ion equivalent of atomic numbers 12, 20–30, 39, 42, 44 or 57–83, Y independently means —OZ$^1$,

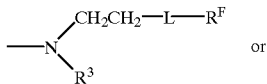

or

-continued

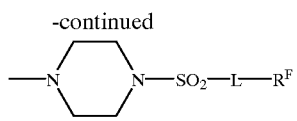

or

A stands for a complex of formula III (III)

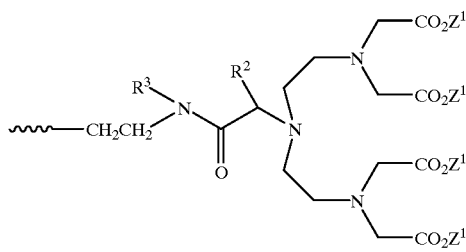

in which $R^3$ and $Z^1$ have the above-mentioned meanings and $R^2$ has the meaning of $R^1$, or A stands for a complex of formula IV (IV)

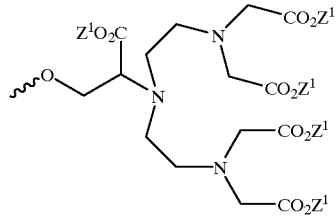

in which $Z^1$ has the above-mentioned meaning, or

A stands for a complex of formula V (V)

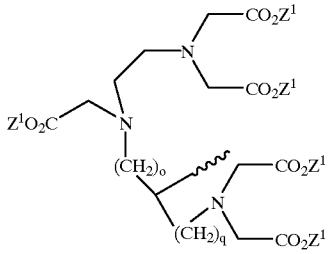

in which $Z^1$ has the above-mentioned meaning, and o and q stand for numbers 0 or 1 and the sum o+q=1 results, or A stands for a complex of formula VI (VI)

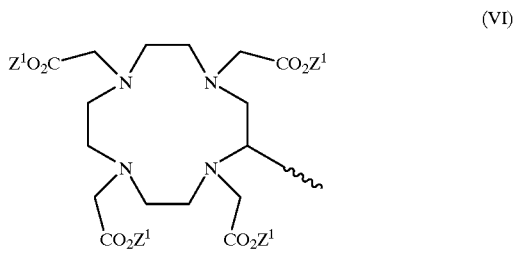

in which $Z^1$ has the above-mentioned meaning or

A stands for a complex of formula VII (VII)

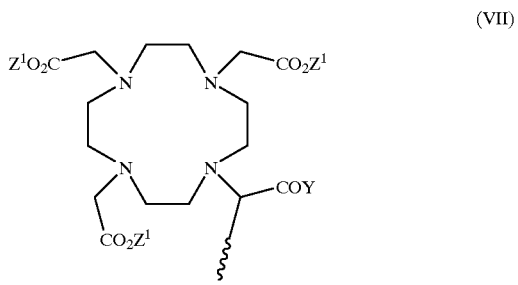

in which $Z^1$ and Y have the above-mentioned meanings or

A stands for a complex of formula VIII (VIII)

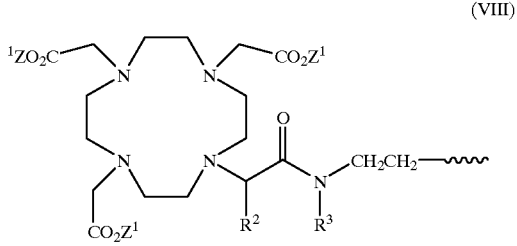

in which $R^3$ and $Z^1$ have the above-mentioned meanings, and $R^2$ has the above-mentioned meaning of $R^1$, or A stands for a complex of formula IX (IX)

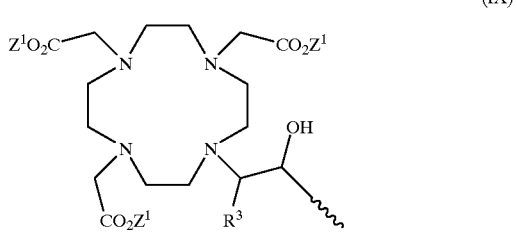

in which $R^3$ and $Z^1$ have the above-mentioned meanings, or

A stands for a complexing agent or complex of formula X

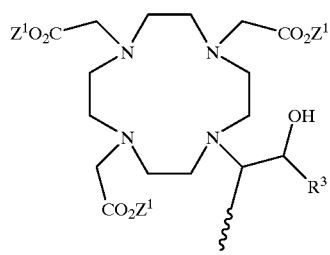
(X)

in which $R^3$ and $Z^1$ have the above-mentioned meanings, or

A stands for a complexing agent or complex of formula XI

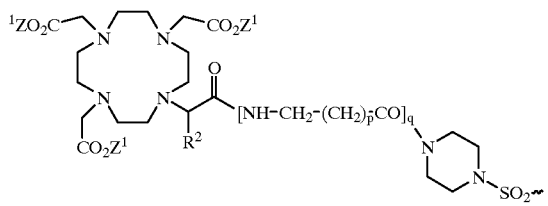
(XI)

in which $Z^1$, p and q have the above-mentioned meanings and $R^2$ has the meaning of $R^1$, or A stands for a complex of formula XII

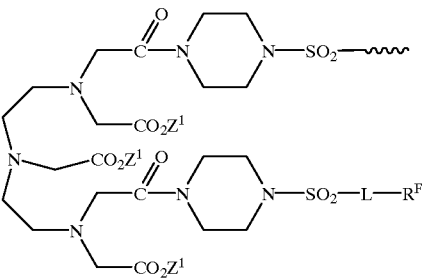
(XII)

in which L, $R^F$ and $Z^1$ have the above-mentioned meanings, or

A stands for a complex of formula XIII

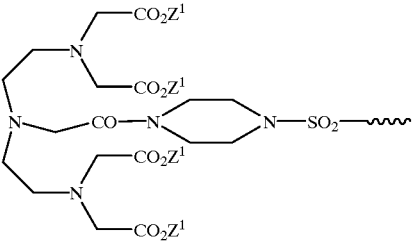
(XIII)

in which $Z^1$ has the above-mentioned meaning.

23. A method as in claim 13, which additionally comprises administering at least one chemotherapy agent.

24. A method as in claim 21, which additionally comprises administering at least one chemotherapy agent.

25. A method as in claim 22, which additionally comprises administering at least one chemotherapy agent.

* * * * *